US010080757B2

(12) United States Patent
Kiessling et al.

(10) Patent No.: US 10,080,757 B2
(45) Date of Patent: Sep. 25, 2018

(54) INHIBITORS OF UDP-GALACTOPYRANOSE MUTASE

(71) Applicant: WISCONSIN ALUMNI RESEARCH FOUNDATION, Madison, WI (US)

(72) Inventors: Laura Lee Kiessling, Madison, WI (US); Valerie Jean Winton, Madison, WI (US); Alexander Mark Justen, Madison, WI (US)

(*) Notice: Subject to any disclaimer, the term of this patent is extended or adjusted under 35 U.S.C. 154(b) by 0 days.

(21) Appl. No.: 15/456,828

(22) Filed: Mar. 13, 2017

(65) Prior Publication Data

US 2017/0258805 A1     Sep. 14, 2017

Related U.S. Application Data

(60) Provisional application No. 62/307,421, filed on Mar. 11, 2016.

(51) Int. Cl.
    *A61K 31/542* (2006.01)
    *A61K 31/426* (2006.01)

(52) U.S. Cl.
    CPC .......... *A61K 31/542* (2013.01); *A61K 31/426* (2013.01)

(58) Field of Classification Search
    CPC ........................... A61K 31/542; A61K 31/426
    See application file for complete search history.

(56) References Cited

U.S. PATENT DOCUMENTS

| | | | |
|---|---|---|---|
| 6,734,307 B2 | 5/2004 | Mehta et al. | |
| 6,956,040 B2 | 10/2005 | Mehta et al. | |
| 7,323,482 B2 | 1/2008 | Hynes et al. | |
| 8,273,778 B2 | 9/2012 | Kiessling et al. | |
| 2004/0054195 A1 | 3/2004 | Gao et al. | |
| 2005/0222408 A1 | 10/2005 | Lee et al. | |
| 2005/0261294 A1 | 11/2005 | Mjalli et al. | |
| 2006/0089371 A1 | 4/2006 | Murata et al. | |
| 2006/0160868 A1 | 7/2006 | Majka et al. | |
| 2008/0064666 A1 | 3/2008 | Verkman et al. | |
| 2015/0344501 A1 | 12/2015 | Kiessling et al. | |

FOREIGN PATENT DOCUMENTS

| | | |
|---|---|---|
| WO | WO 2004/043926 | 5/2004 |
| WO | WO 2005/007625 | 1/2005 |
| WO | WO 2005/103022 | 11/2005 |
| WO | WO 2007/129048 | 11/2007 |
| WO | WO 2009/089027 | 7/2009 |
| WO | WO 2009/132310 | 10/2009 |

OTHER PUBLICATIONS

Aytac et al. (2009) "Synthesis of 3,6-disubstituted 7H-1,2,4-triazolo[3,4-b]-1,3,4-thiadiazines as novel analgesic/anti-inflammatory compounds," European Journal of Medicinal Chemistry 44(11):4528-4538.

Ballatore et al. (Jan. 2013) "Carboxylic acid (bio)isosteres in drug design," ChemMedChem 8:385-395/.

Beis et al (2005) "Crystal Structures of Mycobacteria tuberculosis and Klebsiella pneumoniae UDP-Galactopyranose Mutase in the Oxidised State and Klebsiella pneumoniae UDP-Galactopyranose Mutase in the (Active) Reduced State," J. Mol. Biol. 348(4):971-982.

Bolognese et al. (1977) "Solvolysis in dipolar aprotic solvents. Behavior of 4-(p-substituted phenyl)-4-oxo-2-bromobutanoic acids in dimethyl sulfoxide: substituent effect," The Journal of Organic Chemistry 42(24):3867-3869.

Borrelli et al. (2010) "Antimycobacterial activity of UDP-galactopyranose mutase inhibitors," Int. J. Antimicrob. Agents 36(4):364-368.

Cannon (1995) "Analog Design," Chapter 19 in *Burger's Medicinal Chemistry and Drug Discovery*, Fifth Edition, vol. 1: Principles and Practice, John Wiley & Sons, pp. 783-802.

Caravano et al. (2003) "Synthesis and inhibition properties of conformational probes for the mutase-catalyzed UDP-galactopyranose/furanose interconversion," Chem. Eur. J. 9:5888-5898.

Caravano et al. (2004) "Efficient synthesis of a nucleoside-diphospho-exo-glycal displaying time-dependent inactivation of UDP-galactopyranose mutase," Chem. Commun. (10):1216-1217.

Caravano et al. (2006) "A new methodology for the synthesis of fluorinated exo-glycals and their time-dependent inhibition of UDP-galactopyranose mutase," Chem. Eur. J. 12:3114-3123.

Carlson et al. (2006) "Chemical probes of UDP-galactopyranose mutase," Chem. Biol. 13(8):825-837.

Castagnolo et al. (2008) "Synthesis, Biological Evaluation and SAR Study of Novel Pyrazole Analogues as Inhibitors of Mycobacterium tuberculosis," Bioorg. Med. Chem. 16:8587-8591.

Chad et al. (2007) "Site-directed mutagenesis of UDP-galactopyranose mutase reveals a critical role for the active-site, conserved arginine residues," Biochemistry 46(23):6723-6732.

Dhindsa et al. (1986) "Synthesis and mass spectral studies of some 3-alkyl-6-aryl-7-carbethoxy/carboxy-methyl-s-triazolo[3,4-b][1,3,4]thiadiazines," Indian Journal of Chemistry, Section B: Organic Chemistry Including Medicinal Chemistry 25B(3):283-287.

(Continued)

*Primary Examiner* — Kahsay Habte
(74) *Attorney, Agent, or Firm* — Leydig, Voit & Mayer, Ltd

(57) ABSTRACT

Compounds and salts thereof which are acyl-sulfonamides or certain carboxylic acids and which inhibit microbial growth or attenuate the virulence of pathogenic microorganisms and which inhibit UDP-galactopyranose mutase (UGM). Compounds of the invention include 2-aminothiazoles and triazolothiadiazines, particularly 3,6,7-substituted-7H-[1,2,4]triazolo[3,4-b][1,3,4]thiadiazines, and 2-amino and salts thereof. Methods for inhibiting growth or attenuating virulence of microbial pathogens including *mycobacterium*, for example, *M. tuberculosis* and *M. smegmatis* and *Klebsiella*, for example, *Klebsiella pneumoniae*. Methods for inhibiting eukaryotic human and animal pathogens, and fungi and nematodes in particular. Methods for treatment of infections by prokaryotic and eukaryotic pathogens employing compounds of the invention.

26 Claims, 4 Drawing Sheets

(56) References Cited

OTHER PUBLICATIONS

Dykhuizen et al. (2008) "Inhibitors of UDP-galactopyranose mutase thwart mycobacterial growth," J. Am. Chem. Soc. 130(21):6706-6707.
Dykhuizen et al. (2009) "Potent ligands for prokaryotic UDP-galactopyranose mutase that exploit an enzyme subsite," Org. Lett. 11(1):193-196.
El-Serwy et al. (2012) "Synthesis and anti-inflammatory properties of novel 1,2,4-triazole derivatives," Res. Chem. Intermed. 39:2543-2554.
Feng et al. (2005) "High-throughput assays for promiscuous inhibitors," Nat. Chem. Biol. 1(3):146-148.
Gaulton et al. (2011) "ChEMBL: A large-scale bioactivity database for drug discovery," Nucleic Acids Res. 40(Database Issue):D1100-D1107.
Gruber et al. (2009) "Ligand binding and substrate discrimination by UDP-Galactopyranose mutase," J. Mol. Biol. 391(2):327-340.
Gruber et al. (2009) "X-ray crystallography reveals a reduced substrate complex of UDP-galactopyranose mutase poised for covalent catalysis by flavin," Biochemistry 48(39):9171-9173.
Helm et al. (2003) "Identification of Active-Site Inhibitors of MurG Using a Generalizable, High-Throughput Glycosyltransferase Screen," J. Am. Chem. Soc. 125(37): 11168-11169.
Itoh et al. (2007) "Synthesis and analysis of substrate analogues for UDP-galactopyranose mutase: implication for an oxocarbenium ion intermediate in the catalytic mechanism," Org. Lett. 9(5):879-882.
Jakhar et al. (Jan. 2012) "Molecular iodine mediated one step synthesis and antibacterial properties of some 3-aryl-6-(6-substituted-4-methylcinnolin-3-yl)-7H-1,2,4-triazolo[3,4-b][1,3,4]thiadiazines," Indian Journal of Chemistry, Section B: Organic Chemistry Including Medicinal Chemistry 51B(1):313-317.
Kamel et al. (Aug. 2014) "Synthesis of novel 1,2,4-triazoles, triazolothiadiazines and triazolothiadiazoles as potential anticancer agents," European Journal of Medicinal Chemistry 86:75-80.
Kaplancikh et al. (2008) "New triazole and triazolothiadiazine derivatives as possible antimicrobial agents," European Journal of Medicinal Chemistry 43(1):155-159.
Kincaid et al. (Aug. 2015) "Virtual Screening for UDP-Galactopyranose Mutase Ligands Identifies a New Class of Antimycobacterial Agents," ACS Chem. Biol. 10(10):2209-2218.
Klemm et al. (1998) "Lysosome membrane permeability to anions," Biochim. Biophys. Acta 1373:17-26.
Lack et al. (2011) "Targeting the binding function 3 (BF3) of the human androgen receptor through virtual screening," Journal of Medicinal Chemistry 54(24):8563-8573.
Lee et al. (1997) "Inhibition of UDP-Gal Mutase and Mycobacterial Galactan Biosynthesis by Pyrrolidine Analogues of Galactofuranose," Tetrahedron Lett. 38:6733-6736.
Lee et al. (1999) "An approach to combinatorial library generation of galactofuranose mimics as potential inhibitors of mycobacterial cell wall biosynthesis: Synthesis of a peptidomimetic of uridine 5'-diphosphogalactofuranose (UDP-Galf)," Tetrahedron Lett. 40:8689-8692.
Liautard et al. (2006) "Diastereoselective synthesis of novel iminosugar-containing UDP-Galf mimics: potential inhibitors of UDP-Gal mutase and UDP-Galf transferases," J. Org. Chem. 71:7337-7345.
Liautard et al. (2006) "Stereoselective synthesis of alpha-C-Substituted 1,4-dideoxy-1,4-imino-D-galactitols" Toward original UDP-Galf mimics via cross-metathesis, Org. Lett. 8:1299-1302.
Lipinski (1986) "Bioisosterism in Drug Design," Chapter 27, Section VI—Topics in Chemistry and Drug Design, Allen, R.C. (ed.) in Annual Reports in Medicinal Chemistry 21:283-291.
Lokhov et al. (1992) "Synthesis and High Stability of Complementary Complexes of N-(2-Hydroxyethyl)phenazinium Derivatives of Oligonucleotides," Bioconjugate Chem. 3(5):414-419.
Magnet et al. (2010) "Leads for antitubercular compounds from kinase inhibitor library screens," Tuberculosis 90:354-360.
Mazzone et al. (1989) "Carboxymethyl- and carboxy-derivatives of 7H- and 5H-1,2,4-triazolo[3,4-b][1,3,4]thiadiazine: Synthesis and biological evaluation," Farmaco. 44(10):933-44.
McGovern et al. (2002) "A common mechanism underlying promiscuous inhibitors from virtual and high-throughput screening," J. Med. Chem. 45(8):1712-1722.
Meanwell (2011) Synopsis of Some Recent Tactical Application of Bioisosteres in Drug Design, J. Med. Chem. 54:2529-2591.
Owen et al. (Jun. 8, 2012) "Colloidal aggregation affects the efficacy of anticancer drugs in cell culture," ACS Chem. Biol. 7(8):1429-1435.
Pan et al. (2007) "Synthesis of acyclic galactitol- and lyxitol-aminophosphonates as inhibitors of UDP-galactopyranose mutase," Tetrahedron Lett. 48:4353-4356.
Park et al. (2001) "Metabolism of Fluorine-Containing Drugs" Annu. Rev. Pharmacol. Toxicol. 41:443-470.
Patani et al. (1996) "Bioisosterism; A Rational Approach in Drug Design," Chem Rev. 96:3147-3176.
Pedersen et al. (2003) "Galactofuranose metabolism: a potential target for antimicrobial chemotherapy," Cell. Mol. Life Sci. 60:259-266.
Ronn et al. (2006) "Exploration of acyl sulfonamides as carboxylic acid replacements in protease inhibitors of the hepatitis C virus full-length NS3," Bioorg. Med. Chem. 14:544-559.
Seidler et al. (2003) "Identification and prediction of promiscuous aggregating inhibitors among known drugs," J. Med. Chem. 46:4477-4486.
Soltero-Higgin et al. (2004) "Identification of inhibitors for UDP-galactopyranose mutase," J. Am. Chem. Soc. 126(34):10532-10533.
Somu et al. (2006) "Rationally designed nucleoside antibiotics that inhibit siderophore biosynthesis of mycobacterium tuberculosis," J. Med. Chem. 49:31-34.
Tangallapally et al. (2004) "Synthesis and evaluation of nitrofuranylamides as novel antituberculosis agents," J. Med. Chem. 47:5276-5283.
Teague et al. (1999) "The Design of Leadlike Combinatorial Libraries," Angew. Chem. Int. Ed. Engl. 38(24):3743-3748.
Thiyagarajan et al. (2011) "Functional and structural analyses of N-acylsulfonamide-linked dinucleoside inhibitors of RNase A," FEBS Journal 278:541-549.
Veerapen et al. (2004) "Synthesis of novel ammonium and selenonium ions and their evaluation as inhibitors of UDP-galactopyranose mutase," Carbohydr. Res. 339:2205-2217.
Vovk et al. (2010) "Synthesis of 1-(4-trifluoromethoxyphenyl)-2,5-dimethyl-3-(2-R-thiazol-4-yl)-1H-pyrroles via chain heterocyclization," Molecules 15:997-1006.
Wassermann et al. (2010) "Chemical Substitutions that Introduce Activity Cliffs across Different Compound Classes and Biological Targets," J. Chem. Inf. Model. 50:1248-1256.
Wesener et al. (May 2013) "UDP-galactopyranose mutase in nematodes," Biochemistry 52(25):4391-4398.
Zumla et al. (May 2013) "Advances in the development of new tuberculosis drugs and treatment regimens," Nat. Rev. Drug. Discov. 12:388-404.
Ballatore et al. (2013) "Carboxylic acid (bio)isosteres in drug design," ChemMedChem 8:385-395/.
El-Serwy et al. (Sep. 6, 2012) "Synthesis and anti-inflammatory properties of novel 1,2,4-triazole derivatives," Res. Chem. Intermed. 39:2543-2554.
Feng et al. (Aug. 2005) "High-throughput assays for promiscuous inhibitors," Nat. Chem. Biol. 1(3):146-148.
Gaulton et al. (Sep. 23, 2011) "ChEMBL: A large-scale bioactivity database for drug discovery," Nucleic Acids Res. 40(Database Issue):D1100-D1107.
Helm et al. (Web Release Aug. 22, 2003) "Identification of Active-Site Inhibitors of MurG Using a Generalizable, High-Throughput Glycosyltransferase Screen," J. Am. Chem. Soc. 125(37): 11168-11169.
Kamel et al. (2014) "Synthesis of novel 1,2,4-triazoles, triazolothiadiazines and triazolothiadiazoles as potential anticancer agents," European Journal of Medicinal Chemistry 86:75-80.

(56) References Cited

OTHER PUBLICATIONS

Kincaid et al. (Aug. 17, 2015) "Virtual Screening for UDP-Galactopyranose Mutase Ligands Identifies a New Class of Antimycobacterial Agents," ACS Chem. Biol. 10(10):2209-2218.
Lokhov et al. (Sep. 1992) "Synthesis and High Stability of Complementary Complexes of N-(2-Hydroxyethyl)phenazinium Derivatives of Oligonucleotides," Bioconjugate Chem. 3(5):414-419.
Meanwell (Mar. 2011) Synopsis of Some Recent Tactical Application of Bioisosteres in Drug Design, J. Med. Chem. 54:2529-2591.
Wesener et al. (2013) "UDP-galactopyranose mutase in nematodes," Biochemistry 52(25):4391-4398.

INHIBITORS OF UDP-GALACTOPYRANOSE MUTASE

CROSS-REFERENCE TO RELATED APPLICATIONS

This application claims the benefit of U.S. provisional application 62/307,421 filed Mar. 11, 2016, which application is incorporated by reference herein in its entirety.

STATEMENT REGARDING GOVERNMENT SUPPORT

This invention was made with government support under AI063596 awarded by the National Institutes of Health. The government has certain rights in the invention.

BACKGROUND OF THE INVENTION

Carbohydrates are the most ubiquitous class of biomolecules in nature, yet glycan diversity imparts unique sugar features that can be targeted in a species-specific manner. The monosaccharide galactofuranose (Galf) is found in cell surface glycoconjugates of many human pathogens. However, Galf is absent from the mammalian glycome [Richards, M. R. and T. L. Lowary, Chemistry and Biology of Galactofuranose-Containing Polysaccharides. Chem Bio Chem, 2009. 10(12): p. 1920-1938], making enzymes involved in metabolism of the sugar attractive targets for treatment of human disease.

Galf contributes to virulence in infectious microbes such as *Klebsiella pneumoniae* (Kp) [Richards et al. 2009], *Leishmania major*, and *Aspergillus fumigatus* [Tefsen, B., et al., Galactofuranose in eukaryotes: aspects of biosynthesis and functional impact. Glycobiology, 2012. 22(4):456-469], as well as certain multicellular eukaryotic pathogens [Wesener, D. A., et al., UDP-galactopyranose mutase in nematodes. Biochemistry, 2013. 52(25):4391-8]. *Mycobacterium tuberculosis*, the causative agent of tuberculosis, harbors an essential Galf polysaccharide known as galactan within its renown thick and hydrophobic cell wall complex [Pan, F., et al., *Cell Wall Core Galactofuran Synthesis Is Essential for Growth of Mycobacteria*. J Bacteriol, 2001. 183(13):3991-3998]. Tuberculosis causes an estimated 2 million deaths worldwide every year (WHO report 2014). With the rise of multidrug-resistant and extremely drug resistant *M. tuberculosis* (Mt), tuberculosis is becoming increasingly difficult to treat (WHO report 2014). This underscores the need for new drug candidates in the pipeline.

Cell wall biosynthetic enzymes are targets of several first-line antitubercular drugs, including isoniazid and ethambutol [Richards et al. 2009; Pan et al. 2001]. Uridine 5'-diphosphate (UDP)-galactopyranose mutase (UGM) generates the biological source of UDP-Galf, utilized by galactofuranosyl transferases for construction of the mycobacterial cell wall galactan. UGM is a flavin-dependent protein that catalyzes ring contraction of UDP-galactopyranose (UDP-Galp) to form UDP-Galf [Soltero-Higgin, M., et al., A unique catalytic mechanism for UDP-galactopyranose mutase. Nat Struct Mol Biol, 2004. 11(6): 539-543] (FIG. 1), the five-membered ring isomer of nucleotide-linked galactose. UGM has been validated as a mycobacterial drug target [Dykhuizen, E. C., et al., Inhibitors of UDP-galactopyranose mutase thwart mycobacterial growth. J Am Chem Soc, 2008. 130(21):6706-7; Borrelli, S., et al., Antimycobacterial activity of UDP-galactopyranose mutase inhibitors. Int. J Antimicrob Agents, 2010. 36(4):364-8], and thus small molecule UGM antagonists are significant current interest.

Most efforts to develop UGM inhibitors have focused on UDP-sugar substrate analogs. (Caravano, A.; Dohi, H.; Sinay, P.; Vincent, S. P. Chem.-Eur. J. 2006, 12, 3114-3123; caravanotard, V.; Christina, A. E.; Desvergnes, V.; Martin, O. R. J. Org. Chem. 2006, 71, 7337-7345; Ghavami, A.; Chen, J. J. W.; Pinto, B. M. Carbohydr. Res. 2004, 339, 401-407; Lee, R. E.; Smith, M. D.; Pickering, L.; Fleet, G. W. J. Tetrahedron Lett. 1999, 40:8689-8692; Liautard, V.; Desvergnes, V.; Martin, O. R. Org. Lett. 2006, 8, 1299-1302.) Simple sugar derivatives, including galactopyranose or galactofuranose analogs, bind weakly with affinities in the millimolar range [Lee, R. E.; Smith, M. D.; Nash, R. J.; Griffiths, R. C.; McNeil, M.; Grewal, R. K.; Yan, W. X.; Besra, G. S.; Brennan, P. J.; Fleet, G. W. J. Tetrahedron Lett. 1997, 38, 6733-6736; Veerapen, N.; Yuan, Y.; Sanders, D. A. R.; Pinto, B. M. Carbohydr. Res. 2004, 339, 2205-2217.] Inhibitors that incorporate the uridine portion of the substrate bind substantially better, with affinities that approximate that of UDP-Galp (Kd=52 µM) [Itoh, K.; Huang, Z. S.; Liu, H. W. Org. Lett. 2007, 9, 879-882; Caravano, A.; Vincent, S. P.; Sinay, P. Chem. Commun. 2004, 1216-1217; Caravano, A.; Mengin-Lecreulx, D.; Brondello, J. M.; Vincent, S. P.; Sinay, P. Chem.-Eur. J. 2003, 9, 5888-5898; Pan, W. D.; Ansiaux, C.; Vincent, S. P. Tetrahedron Lett. 2007, 48, 4353-4356; Scherman, M. S.; Winans, K. A.; Stern, R. J.; Jones, V.; Bertozzi, C. R.; McNeil, M. R. Antimicrob. Agents Chemother. 2003, 47, 378-382, El Bkassiny, S., N'Go, I., Sevrain, C. M., Tikad, A., and Vincent, S. P. (2014) Org. Lett. 16, 2462-2465.] These approaches have not yet resulted in compounds that block mycobacterial growth.

Certain non-substrate based molecules have been identified as UGM ligands. For example, certain nitrofuranylamides have been identified as inhibitors of UGM catalysis and mycobacterial growth. [Tangallapally, R. P.; Yendapally, R.; Lee, R. E.; Hevener, K.; Jones, V. C.; Lenaerts, A. J. M.; McNeil, M. R.; Wang, Y. H.; Franzblau, S.; Lee, R. E. J. Med. Chem. 2004, 47, 5276-5283.] Nevertheless, the UGM inhibition and antimycobacterial activity of these compounds were not correlated, so they do not address the utility of inhibiting UGM.

Published International application WO 2005/007625 (Lee et al.), as well as published U.S. application 20050222408, relate to certain heterocyclic amides with antituberculosis activity. More specifically, these patent documents relate to compounds of formula:

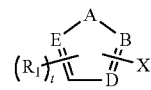

wherein A is selected from the group consisting of oxygen, sulfur, and $NR_{15}$, where $R_{15}$ is selected from the group consisting of H, alkyl, aryl, substituted alkyl, and substituted aryl; B, D, and E are each independently selected from the group consisting of CH, nitrogen, sulfur and oxygen; $R_1$ is selected from the group consisting of nitro, halo, alkyl ester, arylsulfanyl, arylsulfinyl, arylsulfonyl and sulfonic acid; t is an integer from 1 to 3; and X is a substituted amide. These patent documents are incorporated by reference herein at least in part for the definitions of structural elements of the above formula.

A fluorescence polarization (FP) based assay has been developed that allows detection of competitive UGM inhibitors [Soltero-Higgin, M., et al., Identification of inhibitors for UDP-galactopyranose mutase. J Am Chem Soc, 2004. 126(34): p. 10532-3; Dykhuizen, E. C. and L. L. Kiessling, Potent ligands for prokaryotic UDP-galactopyranose mutase that exploit an enzyme subsite. Org Lett, 2009. 11(1): p. 193-6]. Using this FP assay, several high-throughput screens (HTS) have been conducted for small molecule UGM ligands [Soltero-Higgin et al. 2004; Carlson, E. E., J. F. May, and L. L. Kiessling, Chemical probes of UDP-galactopyranose mutase. Chem Biol, 2006. 13(8): p. 825-37]. The screens culminated in fairly low hit rates, revealing the challenging nature of UGM as a target. Nonetheless, through HTS, one series of thiazolidinones (TZ) with considerable activity towards UGM was discovered [Soltero-Higgin et al. 2004]. The TZ series was optimized through scaffold hopping to a 2-aminothiazole (AT) inhibitor core [Dykhuizen, et al., 2008]. The most potent AT displays an $IC_{50}$ of 7.2 µM and 37 µM against KpUGM and MtUGM, respectively [Dykhuizen, et al. 2008; Borrelli et al. 2010].

U.S. Pat. No. 8,273,778 issued Sep. 25, 2012 relates to inhibitors of UDP-galactopyranose mutase having among others, 2-aminothiazole structures. This issued patent is incorporated by reference herein in its entirety for descriptions of the UDP-galactopyranose mutase inhibitors therein as well as methods of assessing such inhibitors and methods of application of such inhibitors.

U.S. published application 2015/0344501 published Dec. 3, 2015 relates to inhibitors of UDP-galactopyranose mutase having among others, triazolothiadiazine structures. This application is incorporated by reference herein in its entirety for descriptions of the UDP-galactopyranose mutase inhibitors therein as well as methods of assessing such inhibitors and methods of application of such inhibitors. See also: Kincaid, V. A., London, N., Wangkanont, K., Wesener, D. A., Marcus, S. A., Heroux, A., Nedyalkova, L., Talaat, A. M., Forest, K. T., Shoichet, B. K., and Kiessling, L. L. (2015) Virtual Screening for UDP-Galactopyranose Mutase Ligands Identifies a New Class of Antimycobacterial Agents, *ACS Chem. Biol.*

While a number of small molecule inhibitors of UDP-galactopyranose mutase have been identified, there remains a need in the art for additional inhibitors which exhibit effective inhibition of microorganisms having UDP-galactopyranose mutase.

SUMMARY OF THE INVENTION

The invention provides compounds which inhibit microbial growth or attenuate the virulence of pathogenic microorganisms. In certain embodiments, compounds of the invention inhibit UDP-galactopyranose mutase (UGM) and have activity as inhibitors of microbial growth of microorganisms which contain this enzyme and particularly those microorganisms in which this enzyme is responsible for the incorporation of galactofuranose residues, particularly for uridine 5'-diphosphate (UDP) galactopyranose mutase. In certain embodiments, compounds of the invention inhibit UDP-galactopyranose mutase (UGM) and have activity to attenuate virulence of pathogenic microorganisms which contain this enzyme and particularly those microorganisms in which this enzyme is responsible for the incorporation of galactofuranose residues.

More specifically, the inhibitors of UGM of this invention inhibit growth or attenuate virulence of microbial pathogens including *mycobacterium*, for example, *M. tuberculosis* and *M. smegmatis*, and/or *Klebsiella*, for example, *Klebsiella pneumoniae*. Preferred inhibitors of UGM are those that specifically inhibit the enzyme rather than those that inhibit by a non-specific mechanism, such as by aggregation. Preferred inhibitors are those that do not exhibit h such aggregation. Additionally, UGM inhibitors of this invention can also inhibit UGM of certain eukaryotic human and animal pathogens, those of fungi and nematodes in particular. Compounds of this invention are useful for treatment of infections in animals, and particularly mammals, by prokaryotic and eukaryotic pathogens. Compounds of this invention are useful in human and veterinary treatment applications. Compounds of this invention are useful for the treatment of tuberculosis. Compounds of this invention are useful in combination therapy with other antibiotics for the treatment of microbial infections, including tuberculosis. Compounds of this invention are useful for the treatment of multiple drug resistant microbial infections, including multiple drug resistant tuberculosis.

In specific embodiments, certain triazolothiadiazine carboxylic acids (carboxylates) and salts thereof of formulas herein are UGM inhibitors and inhibit growth or attenuate virulence of human and animal pathogens including prokaryotic and eukaryotic pathogens.

In specific embodiments, certain N-acylsulfonamide compounds of the invention exhibit superior mycobacterial growth inhibition in comparison to their carboxylate analogs. This enhanced growth inhibition is observed particularly for *Mycobacterium smegmatis*.

Compounds of the invention include N-acylsulfonamide variants of 2-aminothiazoles and triazolothiadiazines, particularly 3,6,7-substituted-7H-[1,2,4]triazolo[3,4-b][1,3,4]thiadiazines:

Formula I

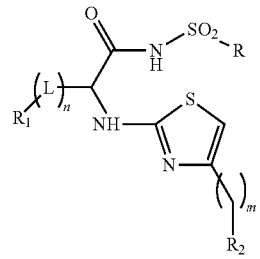

Formula II

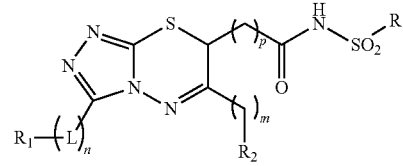

or salts thereof,
where:
n is 0 or 1 and L is L-$(CH_2)_q$— or —O—$(CH_2)_q$—, here q is 1, 2 or 3;
m and p, independently, are 0, 1, 2, or 3;
R is an optionally substituted $C_1$-$C_6$ alkyl, an optionally substituted $C_1$-$C_6$ alkenyl, an optionally substituted alkoxy, an optionally substituted thioalkyl, an optionally substituted carbocyclyl, or an optionally substituted heterocyclyl;
$R_1$ and $R_2$ are independently selected from optionally substituted carbocyclyl, and optionally substituted heterocyclyl;
In specific embodiments, $R_1$ and $R_2$ are independently selected from optionally substituted phenyl, optionally substituted biphenyl and optionally substituted naphthyl groups.

Compounds of the invention also include certain carboxylic acids, carboxylates and salts thereof of 2-aminothiazoles (formula III) and triazolothiadiazines, particularly 3,6,7-substituted-7H-[1,2,4]triazolo[3,4-b][1,3,4]thiadiazines (formula IV):

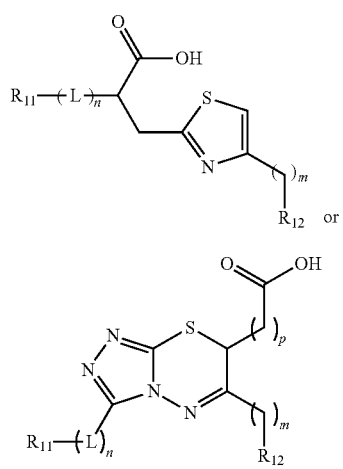

or salts thereof,
where:

n is 0 or 1 and L is L-$(CH_2)_q$— or —O—$(CH_2)_q$—, where q is 1, 2 or 3;

m and p, independently, are 0, 1, 2, or 3;

$R_{11}$ and $R_{12}$ are independently selected from optionally substituted carbocyclyl, and optionally substituted heterocyclyl, with the proviso that one of $R_{11}$ or $R_{12}$ is an optionally substituted biphenyl group or an optionally substituted naphthyl group.

In specific embodiments, $R_{11}$ and $R_{12}$ are independently selected from optionally substituted phenyl, optionally substituted biphenyl and optionally substituted naphthyl groups.

In specific embodiments, compounds of the invention exhibit low cytotoxicity with $LD_{50}$ of 200 µM or less for human or animal cells. In more specific embodiments, compounds of the invention exhibit cytotoxity of $LD_{50}$ of 100 or less for human or animal cells. Preferred compounds of the invention for treatment of a human or animal for a given microorganism (bacterial, fungus, algae or nematode) exhibit $LD_{50}$ for cells of the human or animal which is at least 4-fold or more preferably 5-fold lower than the MIC of the compound for a given microorganism.

The invention provides pharmaceutically acceptable compositions which comprise one or more compounds of formulas I-IV and a pharmaceutically acceptable excipient. In specific embodiments, the excipient is other than water. In specific embodiments, the excipient is other than a solvent.

The invention provides methods for inhibiting UGM comprising contacting UGM with an amount of one or more of the compounds of formulas I-IV which is effective for inhibiting the enzyme.

The invention provides a method for inhibiting incorporation of Galf into a microbial polysaccharide which comprises contacting the microorganism or an environment containing the microorganism with an amount of one or more compounds of formulas I-IV effective for such inhibition.

The invention also provides methods for inhibiting the growth of mycobacteria which comprises contacting the mycobacteria or an environment containing the mycobacteria with an amount of one or more compounds of formulas I-IV effective for such growth inhibition.

The invention also provides methods for treatment of a mycobacterial infection which comprises administering to a human or non-human subject in need of such treatment an amount of one or more compounds of formula I-IV effective for such treatment. In a specific embodiment, the mycobacterial infection is tuberculosis.

DETAILED DESCRIPTION OF THE INVENTION

Figure 1:
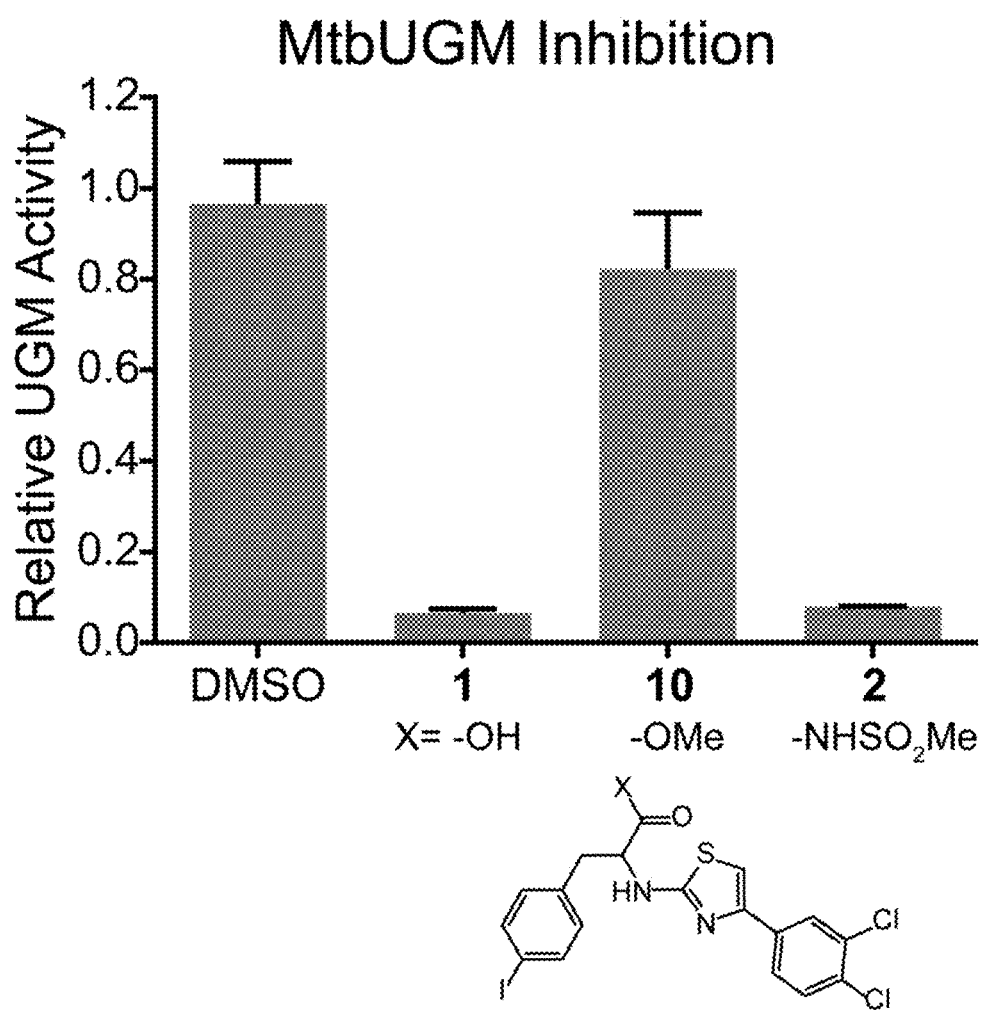
FIG. 1 is a graph comparing inhibitor potency between 2-aminothiazoles with carboxyl replacements. Relative activity of MtbUGM was evaluated with and without inhibitor (50 µM).

The N-acylsulfonamide inhibitors of this invention are useful for inhibition of growth of microorganisms, including bacteria and eukaryotic organisms, such as protozoa and nematodes and the treatment of diseases caused by such organisms. In a specific embodiment, the inhibitors of this invention are useful for inhibition of growth of mycobacteria, and for the treatment of mycobacterial disease. Further the inhibitors of this invention are useful as tools to probe the role of UGM in biological systems. The invention also provided compounds which can be employed as intermediates in the synthesis of additional UGM inhibitors having the structures of formulas I, II, IA and IIA.

Compounds of the invention include N-acylsulfonamide variants of 2-aminothiazoles and triazolothiadiazines, particularly 3,6,7-substituted-7H-[1,2,4]triazolo[3,4-b][1,3,4]thiadiazines:

Formula I

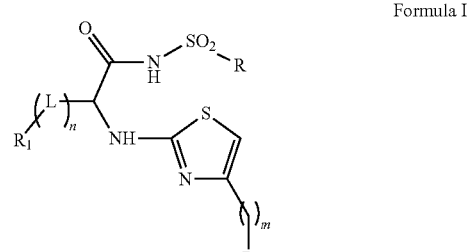

Formula II

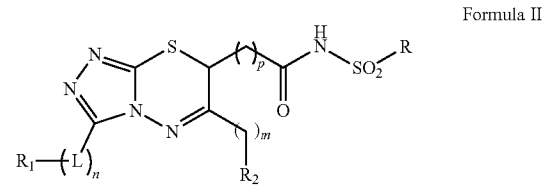

or salts thereof, where:

n is 0 or 1 and L is L-(CH$_2$)$_q$— or —O—(CH$_2$)$_q$—, here q is 1, 2 or 3;

m and p, independently, are 0, 1, 2, or 3;

R is an optionally substituted C$_1$-C$_6$ alkyl, an optionally substituted C$_1$-C$_6$ alkenyl, an optionally substituted alkoxy, an optionally substituted thioalkyl, an optionally substituted carbocyclyl, or an optionally substituted heterocyclyl;

R$_1$ and R$_2$ are independently selected from an optionally substituted carbocyclyl, an optionally substituted heterocyclyl.

More specifically, R$_1$ and R$_2$ are selected from optionally substituted aryl or optionally substituted heteroaryl.

In specific embodiments of formulas I and II, n is 1 and L is —O—(CH$_2$)$_q$—. In specific embodiments of formulas I and II, n is 1 and L is —O—(CH$_2$)$_2$—. In specific embodiments of formulas I and II, n is 1 and L is —O—(CH$_2$)—. In specific embodiments of formulas I and II, n is 1 and L is —(CH$_2$)$_q$—. In specific embodiments of formulas I and II, n is 1 and L is —(CH$_2$)—. In specific embodiments of formulas I and II, n is 1 and L is —(CH$_2$)$_2$—. In specific embodiments of formulas I and II, n is 1 and L is —(CH$_2$)$_3$—. In specific embodiments of formulas I and II, n is 0.

In specific embodiments of formula I, m is 1. In specific embodiments of formula I, m is 2. In specific embodiments of formula I, m is 3. In specific embodiments of formula I, m is 0.

In specific embodiments of formula I, n is 1, L is —O—(CH$_2$)$_2$—, and m is 0 or 1. In specific embodiments of formula I, n is 1 and L is —(CH$_2$)—, and m is 0 or 1. In specific embodiments of formula I, n is 1, L is —(CH$_2$)$_2$—, and m is 0.

In specific embodiments of formula II, n is 1 and L is —O—(CH$_2$)$_q$—. In specific embodiments of formula II, n is 1 and L is —O—(CH$_2$)$_2$—. In specific embodiments of formulas II, n is 1 and L is —O—(CH$_2$)—. In specific embodiments of formula II, n is 1 and L is —(CH$_2$)$_q$—. In specific embodiments of formula II, n is 1 and L is —(CH$_2$)$_1$—. In specific embodiments of formula II, n is 1, L is —(CH$_2$)$_2$—. In specific embodiments of formula II, n is 1 and L is —(CH$_2$)$_3$—. In specific embodiments of formula II, n is 0.

In specific embodiments of formula II, m is 1. In specific embodiments of formula II, m is 2. In specific embodiments of formula II, m is 3. In specific embodiments of formula II, m is 0.

In specific embodiments of formula II, p is 1. In specific embodiments of formula II, p is 2. In specific embodiments of formula II, p is 3. In specific embodiments of formula II, p is 0.

In specific embodiments of formula II, n is 1 and L is —O—(CH$_2$)$_2$—, m is 0 or 1 and p is 1 or 2. In specific embodiments of formula II, n is 1 and L is —(CH$_2$)—, m is 0 or 1 and p is 1 or 2. In specific embodiments of formula II, n is 1 and L is —(CH$_2$)$_2$—, m is 0 or 1 and p is 1 or 2.

In specific embodiments herein, R is an optionally substituted cycloalkyl, an optionally substituted cycloalkenyl, or an optionally substituted heteroaryl. In specific embodiments, R is an optionally substituted aryl or an optionally substituted heteroaryl having one or two rings, wherein when two rings of the group are present they are bonded through a single bond, e.g., a C—C bond, or are fused.

In specific embodiments, R$_1$ and/or R$_2$ is independently an optionally substituted aryl or optionally substituted heteroaryl group having one or two rings, wherein when two rings of the group are present they are bonded through a single bond, e.g., a C—C bond, or are fused.

In specific embodiments, R$_1$ and/or R$_2$ is independently a heterocyclyl group having one or two rings and 1-4 heteroatoms, wherein when two rings of the group are present they are bonded through a single bond, e.g., a C—C bond, or are fused.

In specific embodiments, R$_1$ and/or R$_2$ is independently a heterocyclyl group having one ring and 1-3 heteroatoms. In specific embodiments, R$_1$ and/or R$_2$ is independently a heterocyclyl group having one 5 or 6-member ring and 1-3 heteroatoms. In specific embodiments, R$_1$ and/or R$_2$ is independently a heterocyclyl group having one or two 5- or 6-member ring and 1-4 heteroatoms, wherein when two rings of the group are present they are bonded through a single bond, e.g., a C—C bond, or are fused.

In specific embodiments, R$_1$ and/or R$_2$ is independently a heteroaryl group having one or two rings, wherein when two rings of the group are present they are bonded through a single bond, e.g., a C—C bond, or are fused.

In specific embodiments, R$_1$ and/or R$_2$ is independently a heteroaryl group having one 5- or 6-member ring and 1 or 2 heteroatoms. In specific embodiments, R$_1$ and/or R$_2$ is independently a heteroaryl group having one 5- or 6-member ring and 1 or 2 heteroatoms.

In specific embodiments, R$_1$ and/or R$_2$ is independently an optionally substituted aryl group. In specific embodiments, R$_1$ and/or R$_2$ is independently an optionally substituted phenyl group. In specific embodiments, R$_1$ and/or R$_2$ is independently an optionally substituted benzyl group. In specific embodiments, R$_1$ and/or R$_2$ is independently an optionally substituted biphenyl group. In specific embodiments, R$_1$ and/or R$_2$ is independently an optionally substituted naphthyl group.

In specific embodiments, R$_1$ and R$_2$ are independently optionally substituted aryl or optionally substituted heteroaryl groups having one or two rings or are alkyl groups substituted with an optionally substituted aryl, or optionally substituted heteroaryl group having one or two rings. In specific embodiments, the optionally substituted aryl, or optionally substituted heteroaryl groups have two fused rings. In specific embodiments, the optionally substituted aryl, or optionally substituted heteroaryl groups have two rings bonded through a single bond, e.g., a C—C bond.

In specific embodiments of formula I, R$_1$ is selected from furan-2-yl, furan-3-yl, 4-F-phenyl, 4-F-benzyl, thiophen-2-yl, thiophen-3-yl, 1-methylfuran-3-yl, 4-Cl-phenoxy-CH$_2$—, 2-methoxyphenyl, 4-F-phenyl, 4-F-benzyl, 4-Br-benzyl, 4-Br-phenyl, 4-Cl-phenyl, 4-Cl-benzyl, 1,1'-biphenyl-4-yl, 1,1'-biphenyl-3-yl, 1,1'-biphenyl-4-ylmethyl, 1,1'-biphenyl-3-ylmethyl, naphthalen-1-yl, naphthalene-2-yl, naphthalen-1-ylmethyl, and naphthalene-2-ylmethyl.

In specific embodiments of formula I, R$_2$ is selected from furan-2-yl, furan-3-yl, 4-F-phenyl, 4-F-benzyl, thiophen-2-yl, thiophen-3-yl, 1-methylfuran-3-yl, 4-Cl-phenoxy-CH$_2$—, 2-methoxyphenyl, 4-F-phenyl, 4-F-benzyl, 4-Br-benzyl, 4-Br-phenyl, 4-Cl-phenyl, 4-Cl-benzyl, 1,1'-biphenyl-4-yl, 1,1'-biphenyl-3-yl, 1,1'-biphenyl-4-ylmethyl, 1,1'-biphenyl-3-ylmethyl, naphthalen-1-yl, naphthalene-2-yl, naphthalen-1-ylmethyl, and naphthalene-2-ylmethyl.

In specific embodiments, R$_1$ is a different group from R$_2$.

In specific embodiments of formula I, R$_1$ is selected from 4-F-phenyl, 4-F-benzyl, 4-F-phenyl, 4-Cl-benzyl, 4-Cl-phenyl, 4-Br-benzyl, 4-Br-phenyl, thiophen-2-yl, phenyl, or 4-methylphenyl.

In specific embodiments of formula I, R$_1$ is selected from benzyl, phenethyl, 1,1'-biphenyl-4-yl, 1,1'-biphenyl-3-yl, 1,1'-biphenyl-4-ylmethyl, 1,1'-biphenyl-3-ylmethyl, naphthalen-1-yl, naphthalene-2-yl, naphthalen-1-ylmethyl, and naphthalene-2-ylmethyl.

In specific embodiments of formula I, $R_2$ is selected from 4-F-phenyl, 4-F-benzyl, 4-F-phenyl, 4-Cl-benzyl, 4-Cl-phenyl, 4-Br-benzyl, 4-Br-phenyl, thiophen-2-yl, phenyl, or 4-methylphenyl.

In specific embodiments of formula I, $R_2$ is selected from benzyl, phenethyl, 1,1'-biphenyl-4-yl, 1,1'-biphenyl-3-yl, 1,1'-biphenyl-4-ylmethyl, 1,1'-biphenyl-3-ylmethyl, naphthalen-1-yl, naphthalene-2-yl, naphthalen-1-ylmethyl, and naphthalene-2-ylmethyl.

In specific embodiments of formula I, one of $R_1$ or $R_2$ is selected from furan-2-yl, furan-3-yl, 4-F-phenyl, 4-F-benzyl, thiophen-2-yl, thiophen-3-yl, 1-methylfuran-3-yl, 4-Cl-phenoxy-$CH_2$—, 2-methoxyphenyl, 4-F-phenyl, 4-F-benzyl, 4-Br-benzyl, 4-Br-phenyl, 4-Cl-phenyl, 4-Cl-benzyl and the other of $R_1$ or $R_2$ is an unsubstituted phenyl group or a substituted phenyl group. Note that various embodiments of substituted phenyl groups are described with respect to the compounds of formula IA below and $R_1$ or $R_2$ can be any of such substituted phenyl groups.

In specific embodiments of formula II, $R_1$ is selected from furan-2-yl, furan-3-yl, 4-F-phenyl, 4-F-benzyl, thiophen-2-yl, thiophen-3-yl, 1-methylfuran-3-yl, 4-Cl-phenoxy-$CH_2$—, 2-methoxyphenyl, 4-F-phenyl, 4-F-benzyl, 4-Br-benzyl, 4-Br-phenyl, 4-Cl-phenyl, 4-Cl-benzyl.

In specific embodiments of formula II, $R_2$ is selected from furan-2-yl, furan-3-yl, 4-F-phenyl, 4-F-benzyl, thiophen-2-yl, thiophen-3-yl, 1-methylfuran-3-yl, 4-Cl-phenoxy-$CH_2$—, 2-methoxyphenyl, 4-F-phenyl, 4-F-benzyl, 4-Br-benzyl, 4-Br-phenyl, 4-Cl-phenyl, 4-Cl-benzyl.

In specific embodiments of formula II, $R_1$ is selected from 4-F-phenyl, 4-F-benzyl, 4-F-phenyl, 4-Cl-benzyl, 4-Cl-phenyl, 4-Br-benzyl, 4-Br-phenyl, thiophen-2-yl, phenyl, or 4-methylphenyl.

In specific embodiments of formula II, $R_2$ is selected from 4-F-phenyl, 4-F-benzyl, 4-F-phenyl, 4-Cl-benzyl, 4-Cl-phenyl, 4-Br-benzyl, 4-Br-phenyl, thiophen-2-yl, phenyl, or 4-methylphenyl.

In specific embodiments of formula I, $R_1$ is 4-I-phenyl. In specific embodiments of formula II, $R_1$ is 4-I-phenyl.

In specific embodiments of formula I, $R_1$ is 4-I-benzyl. In specific embodiments of formula I, $R_1$ is 4-I-benzyl.

In specific embodiments of formula I, $R_2$ is selected from p-F-phenyl, p-F-benzyl, p-F-phenyl, p-Cl-benzyl p-Cl-phenyl, p-Br-benzyl, p-Br-phenyl, thien-2-yl, phenyl, 4-methoxyphenyl or 4-methylphenyl.

In specific embodiments of formula I or II, $R_1$ is 4-Br-phenyl-; 4-Cl-phenyl; 4-Cl-benzyl; 4-I-phenyl; 4-I-benzyl; 4-Br-phenoxy-$CH_2$—; 4-I-phenoxy-$CH_2$—; or 4-F-phenoxy-$CH_2$—.

In specific embodiments of formula I or II, $R_2$ is p-halobenzyl. In specific embodiments of formula I or II, $R_2$ is 4-Br-benzyl. In specific embodiments of formula or II, $R_2$ is 4-I-benzyl. In specific embodiments of formula I or II, $R_2$ is p-I-phenyl.

In specific embodiments of formula II, one of $R_1$ or $R_2$ is selected from furan-2-yl, furan-3-yl, 4-F-phenyl, 4-F-benzyl, thiophen-2-yl, thiophen-3-yl, 1-methylfuran-3-yl, 4-Cl-phenoxy-$CH_2$—, 2-methoxyphenyl, 4-F-phenyl, 4-F-benzyl, 4-Br-benzyl, 4-Br-phenyl, 4-Cl-phenyl, 4-Cl-benzyl and the other of $R_1$ or $R_2$ is an unsubstituted phenyl group or a substituted phenyl group. Note that various embodiments of substituted phenyl groups are described with respect to the compounds of formula IA below and $R_1$ or $R_2$ can be any of such substituted phenyl groups.

In specific embodiments of formula I or II:

$R_2$ is thiophen-2-yl and $R_1$ is p-Br-benzyl, p-Cl-benzyl, p-I-benzyl, p-halophenyl, p-methylphenyl or phenyl;

$R_2$ is p-Cl-phenyl and $R_1$ is p-F-benzyl, p-Cl-phenyl, p-Cl-benzyl, p-Cl-phenoxy-$CH_2$—, p-Br-phenyl, p-I-phenyl or p-I-benzyl;

$R_2$ is p-methylphenyl and $R_1$ is p-Br-phenyl, p-Br-benzyl, p-Cl-phenyl, p-Cl-benzyl, p-I-phenyl or p-I-benzyl;

$R_2$ is phenyl and $R_1$ is p-Br-phenyl, p-Br-benzyl, p-Cl-phenyl, p-Cl-benzyl, p-I-phenyl or p-I-benzyl;

$R_2$ is p-F-phenyl and $R_1$ is p-F-phenyl, p-F-benzyl, p-Cl-phenoxy-$CH_2$—, or thien-2-yl;

$R_2$ is o-methoxyphenyl and $R_1$ is p-F-phenyl, p-F-benzyl, p-Cl-phenoxy-$CH_2$, thien-2-yl, p-Br-phenyl, p-Br-benzyl, p-I-phenyl, p-I-benzyl or p-C-benzyl.

$R_1$ is p-F-phenyl and $R_2$ is p-F-phenyl, p-F-benzyl, p-Cl-benzyl, thien-2-yl, p-I-phenyl, p-I-benzyl, p-Br-phenyl, or p-Br-benzyl;

$R_1$ is p-F-benzyl and $R_2$ is p-Cl-phenyl, p-Cl-benzyl, p-I-phenyl, p-I-benzyl, p-Br-phenyl, or p-Br-benzyl;

$R_1$ is p-Br-benzyl and $R_2$ is thien-2-yl, p-Cl-benzyl, p-Br-phenyl, p-Br-benzyl, p-I-phenyl, or p-I-benzyl;

$R_1$ is fur-2-yl and $R_2$ is p-Br-phenyl;

$R_1$ is thien-2-yl and $R_2$ is p-F-phenyl, p-Br-phenyl, or p-I-phenyl; or $R_1$ is p-Cl-phenoxy-$CH_2$— and $R_2$ is p-F-phenyl, p-F-benzyl, p-Cl-phenyl, p-Cl-benzyl, p-Br-phenyl, p-Br-benzyl, p-I-phenyl, or p-I-benzyl.

In specific embodiments of formulas I or II, one of $R_1$ or $R_2$ is a dichloro-, difluoro- or dibromophenyl. In specific embodiments, one of $R_1$ or $R_2$ is a 3,4-dichloro-, 3,4-difluoro-, 3,4-dibromophenyl or 3,4-diiodophenyl.

In specific embodiments, the $R_1$ and/or $R_2$ groups are optionally substituted phenyl rings. In specific embodiments, both the $R_1$ and $R_2$ groups are optionally substituted phenyl rings. In specific embodiments, the $R_1$ and/or the $R_2$ groups are heteroaryl 6-member rings. In specific embodiments, the $R_1$ group or the $R_2$ group is a one or two 5- or 6-member carbocyclic or heterocyclic ring. In specific embodiments, the $R_1$ and/or $R_2$ groups are selected from pyridyl, indolyl, furanyl, purinyl, pyrazinyl, pyranyl, pyrimidinyl, thiophenyl, benzofuranyl, naphthyl or benzothiophenyl rings. In a specific embodiment, $R_1$ and $R_2$ are both phenyl rings and there is at least one non-hydrogen substituent the rings. In a specific embodiment, one of $R_1$ and $R_2$ is an optionally substituted phenyl ring and the other of $R_1$ or $R_2$ is a heterocyclyl ring.

In specific embodiments of formulas I or II, m is 0 or 1, n is 0 or 1 and p (if present) is 0 or 1, where L, if present, is —$CH_2$—. In specific embodiments of formulas I or II, m is 0 or 1, n is 0 or 1 and p (if present is 0 or 1, where L if present is —$CH_2$—, $R_1$ is unsubstituted biphenyl or unsubstituted naphthyl and $R_2$ is unsubstituted biphenyl, unsubstituted naphthyl, p-Cl-phenyl, p-Br-phenyl, p-I-phenyl or m, p-diclorophenyl. In specific embodiments of formulas I or II, m is 0 or 1, n is 0 or 1 and p (if present is 0 or 1, where L if present is —$CH_2$—, $R_2$ is unsubstituted biphenyl or unsubstituted naphthyl and $R_1$ is unsubstituted biphenyl, unsubstituted naphthyl, p-Cl-phenyl, p-Br-phenyl, p-I-phenyl or m, p-diclorophenyl.

In more specific embodiments the invention provides compounds of formula:

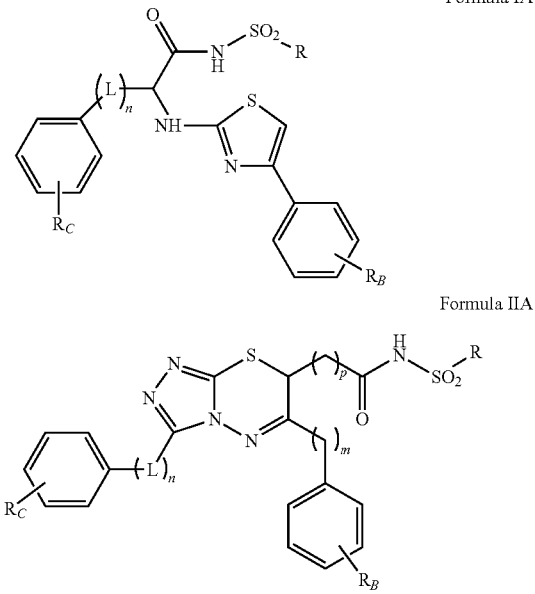

Formula IA

Formula IIA or a salt thereof,
where:
n is 0 or 1 and L is L-$(CH_2)_q$— or —O—$(CH_2)_q$, here q is 1, 2 or 3;
m and p, independently, are 0, 1, 2, or 3;
$R_C$ and $R_B$ represent no substitution on the indicated ring (i.e. 5 hydrogens); or
$R_C$ and $R_B$, independently, represent substitution on the indicated ring with one or more of the groups halogen, hydroxyl, mercapto (—SH), nitro, cyano, azide, isocyano, thiocyano, optionally substituted $C_1$-$C_6$ alkyl, optionally substituted $C_1$-$C_6$ alkenyl, optionally substituted $C_1$-$C_6$ alkoxy, optionally substituted thioalkyl, optionally substituted aryl, optionally substituted heteroaryl, optionally substituted cycloalkyl, optionally substituted heterocyclyl, —$SO_2$—$N(R_D)_2$, —$SO_2$—$R_D$, —$COOR_D$, —$COR_D$, —$CON(R_D)_2$, —$N(R_D)_2$, where $R_D$ is hydrogen or a $C_1$-$C_6$ optionally substituted alkyl group or
$R_B$ or $R_C$ substituents on two adjacent carbons of the indicated ring together with the carbons to which they are attached form a carbocyclic or heterocyclic ring having 5 to 8 ring atoms and optionally wherein one or two of the ring members are heteroatoms, particularly N, O or S, which 5- to 8-member ring may be an aromatic ring;
R is an optionally substituted $C_1$-$C_6$ alkyl, an optionally substituted $C_1$-$C_6$ alkenyl, an optionally substituted alkoxy, an optionally substituted thioalkyl, an optionally substituted aryl, an optionally substituted heteroaryl, an optionally substituted cycloalkyl, or an optionally substituted heterocyclyl,
wherein substitution for R, $R_C$ and $R_B$ groups includes substitution with one or more halogen, hydroxyl, mercapto (—SH), nitro, cyano, azide, isocyano, thiocyano, oxo (to form, for example, a —CO— moiety) optionally substituted $C_1$-$C_6$ alkyl, optionally substituted $C_1$-$C_6$-alkenyl, optionally substituted $C_1$-$C_6$ alkoxy, optionally substituted thioalkyl, optionally substituted aryl, optionally substituted heteroaryl, optionally substituted cycloalkyl, optionally substituted heterocyclyl, —$SO_2$—$N(R_S)_2$, —$SO_2$—$R_S$, —$COOR_S$, —$COR_S$, —$CON(R_S)_2$, —$N(R_S)_2$, where $R_S$ is hydrogen, $C_1$-$C_6$ alkyl, C1-C6 alkenyl, $C_1$-$C_6$ haloalkyl, $C_1$-$C_6$ haloalkoxy, phosphate, phosphonate, carboxyl, and
wherein substitution for substituent groups, if present, includes one or more halogen, halogen, hydroxyl, mercapto (—SH), nitro, cyano, azide, isocyano, thiocyano, isocyanate, isothiocyanate, unsubstituted $C_1$-$C_6$ alkyl, unsubstituted $C_1$-$C_6$-alkenyl, unsubstituted $C_1$-$C_6$ alkoxy, unsubstituted thioalkyl, unsubstituted aryl,
unsubstituted heteroaryl, unsubstituted cycloalkyl,
unsubstituted heterocyclyl, —$SO_2$—$N(R_S)_2$, —$SO_2$—$R_S$, —$COOR_S$, —$COR_S$, —$CON(R_S)_2$, —$N(R_S)_2$, where $R_S$ is hydrogen, $C_1$-$C_6$ alkyl, $C_1$-$C_6$ alkenyl, $C_1$-$C_6$haloalkyl, or $C_1$-$C_6$ haloalkoxy.

In specific embodiments, the compound of the invention is that of formula IA. In specific embodiments of formula IA, n is 0, 1 or 2. In specific embodiments of formula IA, n is 0. In specific embodiments of formula IA, n is 1. In specific embodiments of formula IA, n is 2.

In specific embodiments of formula IA, R is an optionally substituted $C_1$-$C_6$ alkyl. In specific embodiments of formula IA, R is an unsubstituted $C_1$-$C_6$ alkyl. In specific embodiments of formula IA, R is an optionally substituted $C_1$-$C_6$ alkenyl. In specific embodiments of formula IA, R is an unsubstituted $C_1$-$C_6$ alkenyl. In specific embodiments, R is a methyl, ethyl or propyl group including all isomers thereof. In specific embodiments, R is a $C_1$-$C_3$ haloalkyl group. In specific embodiments, R is a $C_1$-$C_3$ fluoroalkyl group. In specific embodiments, R is a —$CF_3$ group.

In specific embodiments of formula IA, R is an optionally substituted aryl. In specific embodiments of formula IA, R is an unsubstituted aryl. In specific embodiments of formula IA, R is a phenyl group. In specific embodiments of formula IA, R is a mono-substituted phenyl group. In specific embodiments of formula IA, R is a 4-substituted phenyl group. In specific embodiments of formula IA, R is a 2-substituted phenyl group. In specific embodiments of formula IA, R is a mono- or di-substituted phenyl group. In specific embodiments of formula IA where R is a substituted phenyl group, substituents include one or more halogen, nitro, $C_1$-$C_3$ alkyl, $C_1$-$C_3$ alkoxy, $C_1$-$C_3$-haloalkyl, or $C_1$-$C_3$-fluoralkyl.

In specific embodiments of formula IA, R is a biphenyl group. In specific embodiments of formula IA, R is a 4'-substituted biphenyl group. In specific embodiments of formula IA, R is a naphthyl group. In specific embodiments of formula IA, R is a naphth-1-yl group. In specific embodiments of formula IA, R is a naphthy-2-yl group.

In specific embodiments of formula IA, R is an optionally substituted heteroaryl. In specific embodiments of formula IA, R is an unsubstituted heteroaryl. In specific embodiments of formula IA, R is an optionally substituted cycloalkyl. In specific embodiments of formula IA, R is an unsubstituted cycloalkyl. In specific embodiments of formula IA, R is an optionally substituted heterocyclyl. In specific embodiments of formula IA, R is an unsubstituted heterocyclyl.

In specific embodiments of formula IA, R is an optionally substituted phenyl group. In specific embodiments of formula IA, R is an unsubstituted phenyl group.

In specific embodiments of formula IA, R is an optionally substituted thiophenyl group. In specific embodiments of formula IA, R is a thiophen-2-yl group. In specific embodiments of formula IA, R is a thiophen-3-yl group. In specific embodiment of formula IA, R is a chlorinated thiophenyl groups, for example a 5-chloro-thiophen-2-yl. In specific embodiments of formula IA, R is a furanyl group. In specific embodiments of formula IA, R is a furan-2-yl group. In specific embodiments of formula IA, R is a furan-3-yl group. In specific embodiments of formula IA, R is a pyrrolyl group. In specific embodiments of formula IA, R is a pyrrol-2-yl group. In specific embodiments of formula IA, R is a pyrrol-3-yl group. In specific embodiments of formula IA, R is a 2H-pyrrolyl group. In specific embodiments of formula IA, R is a 2H-pyrrol-2-yl group. In specific embodiments of formula IA, R is a 2H-pyrrol-3-yl group. In specific embodiments of formula IA, R is an imidazolyl group. In specific embodiments of formula IA, R is an imidazol-2-yl group. In specific embodiments of formula IA, R is an imidazol-3-yl group.

In specific embodiments of formula IA, R is a pyridinyl group. In specific embodiments of formula IA, R is a pyridin-2-yl group. In specific embodiments of formula IA, R is a pyridin-3-yl group. In specific embodiments of formula IA, R is a pyridin-4-yl group. In specific embodiments of formula IA, R is a pyrimidinyl group. In specific embodiments of formula IA, R is a pyrimidin-2-yl group. In specific embodiments of formula IA, R is a pyrimidin-4-yl group. In specific embodiments of formula IA, R is a pyrimidin-5-yl group. In specific embodiments of formula IA, R is a pyridazinyl group. In specific embodiments of formula IA, R is a pyridazin-3-yl group. In specific embodiments of formula IA, R is a pyridazin-4-yl group. In specific embodiments of formula IA, R is a pyridazin-5-yl group. In specific embodiments of formula IA, R is a pyrazinyl group. In specific embodiments of formula IA, R is a pyrazin-2-yl group. In specific embodiments of formula IA, R is a pyrazin-3-yl group. In specific embodiments of formula IA, R is a pyranyl group. In specific embodiments of formula IA, R is a pyran-2-yl group. In specific embodiments of formula IA, R is a pyran-3-yl group. In specific embodiments of formula IA, R is a pyran-5-yl group.

In specific embodiments of formula IA, R is a halo allyl group (—CH=CH—CH$_2$—H, where H is F, Cl, Br or I). In specific embodiments of formula IA, R is —CH=CH—CH$_2$—Cl or —CH=CH—CH$_2$—Br. In specific embodiments of formula IA, R is an optionally substituted oxiranyl group. In specific embodiments of formula IA, R is an unsubstituted oxiranyl group.

In specific embodiments of formula IA, one of $R_B$ or $R_C$ is five hydrogen (i.e., one phenyl ring is unsubstituted) and the other of $R_B$ or $R_C$ caries at least one non-hydrogen substituent. In specific embodiments of formula IA, $R_B$ is mono-substitution at the 4-position of the ring. In specific embodiments of formula IA, $R_B$ is mono-substitution at the 3-position of the ring. In specific embodiments of formula IA, $R_B$ is mono-substitution at the 3-position of the ring. In specific embodiments of formula IA, $R_B$ is di-substitution at the 2- and 4-positions of the ring. In specific embodiments of formula IA, $R_B$ is di-substitution at the 3- and 5-positions of the ring. In specific embodiments of formula IA, $R_B$ is di-substitution at the 3- and 4-positions of the ring. In specific embodiments of formula IA, $R_B$ is tri-substitution at the 2-, 3- and 4-positions of the ring. In specific embodiments of formula IA, $R_B$ is tri-substitution at the 3-, 4- and 5-positions of the ring. In specific embodiments of formula IA, $R_B$ is tetra-substitution at the 2-, 3-, 4- and 5-positions of the ring. In specific embodiments of formula IA, $R_B$ is penta-substitution of the ring. In specific embodiments of the forgoing embodiments, the substituents are all halogens. In specific embodiments of the forgoing embodiments, the substituents are all fluorines. In specific embodiments of the forgoing embodiments, the substituents are all chlorines. In specific embodiments of the forgoing embodiments, the substituents are all bromines. In specific embodiments of the forgoing embodiments, the substituents are chlorines and nitro groups.

In specific embodiments of formula IA, $R_B$ is one or two halogens, cyano groups, or nitro groups substituted on the ring. In specific embodiments of formula IA, $R_B$ is one or two nitro groups. In specific embodiments of formula IA, $R_B$ is a nitro group substituted at the 4-ring position. In specific embodiments of formula IA, $R_B$ is a nitro group substituted at the 3-ring position. In specific embodiments of formula IA, $R_B$ is a cyano group substituted at the 4-ring position. In specific embodiments of formula IA, $R_B$ is a cyano group substituted at the 3-ring position. In specific embodiments of formula IA, $R_B$ is a halogen at the 4-position of the ring. In specific embodiments of formula IA, $R_B$ is a halogen at the 3-position of the ring. In specific embodiments of formula IA, $R_B$ is a halogen at the 2-position of the ring. In specific embodiments of formula IA, $R_B$ is two halogens at the 2- and 4-positions of the ring. In specific embodiments of formula IA, $R_B$ is two halogens at the 3- and 4-positions of the ring. In specific embodiments of formula IA, $R_B$ is three halogens at the 2-, 3- and 4-positions of the ring. In specific embodiments of formula IA, $R_B$ is three halogens at the 3-, 4- and 5-positions of the ring. In embodiments of the forgoing embodiments, all halogens are fluorine. In embodiments of the forgoing embodiments, all halogens are chlorine. In embodiments of the forgoing embodiments, all halogens are bromine. In embodiments of the forgoing embodiments, at least one halogen is iodine.

In specific embodiments of formula IA, $R_B$ is an iodine at the 4-position of the ring. In specific embodiments of formula IA, $R_B$ is a fluorine at the 4-position of the ring. In specific embodiments of formula IA, $R_B$ is a bromine at the 4-position of the ring. In specific embodiments of formula IA, $R_B$ is a chlorine at the 4-position of the ring. In specific embodiments of formula IA, $R_B$ is a chlorine at the 3-position of the ring. In specific embodiments of formula IA, $R_B$ is a chlorine at the 2-position of the ring. In specific embodiments of formula IA, $R_B$ is two fluorines at the 2- and 4-positions of the ring. In specific embodiments of formula IA, $R_B$ is two fluorines at the 3- and 4-positions of the ring. In specific embodiments of formula IA, $R_B$ is two fluorines at the 3- and 5-positions of the ring. In specific embodiments of formula IA, $R_B$ is two bromines at the 2- and 4-positions of the ring. In specific embodiments of formula IA, $R_B$ is two bromines at the 3- and 4-positions of the ring. In specific embodiments of formula IA, $R_B$ is two bromines at the 3- and 5-positions of the ring. In specific embodiments of formula IA, $R_B$ is two chlorines at the 2- and 4-positions of the ring. In specific embodiments of formula IA, $R_B$ is two chlorines at the 3- and 4-positions of the ring. In specific embodiments of formula IA, $R_B$ is two chlorines at the 3- and 5-positions of the ring. In specific embodiments of formula IA, $R_B$ is a nitro group at the 3-position of the ring and a chlorine at the 4-position of the ring.

In specific embodiments of formula IA, $R_B$ a hydroxyl group at the 4-position of the ring. In specific embodiments of formula IA, $R_B$ $C_1$-$C_3$ alkyl group at the 2-position of the ring. In specific embodiments of formula IA, $R_B$ a $C_1$-$C_3$ alkyl group at the 2-position of the ring and a hydroxyl group at the 4-position of the ring. In specific embodiments of formula IA, $R_B$ a $C_1$-$C_3$ alkoxy group at the 4-position of the ring. In specific embodiments of formula IA, $R_B$ a $C_1$-$C_6$ alkyl group at the 4-position of the ring.

In specific embodiments of formula IA, $R_C$ is mono-substitution at the 4-position of the ring. In specific embodiments of formula IA, $R_C$ is mono-substitution at the 3-position of the ring. In specific embodiments of formula IA, $R_C$ is mono-substitution at the 3-position of the ring. In specific embodiments of formula IA, $R_C$ is di-substitution at the 2- and 4-positions of the ring. In specific embodiments of formula IA, $R_C$ is di-substitution at the 3- and 5-positions of the ring. In specific embodiments of formula IA, $R_C$ is di-substitution at the 3- and 4-positions of the ring. In specific embodiments of formula IA, $R_C$ is tri-substitution at the 2-, 3- and 4-positions of the ring. In specific embodiments of formula IA, $R_C$ is tri-substitution at the 3-, 4- and 5-positions of the ring. In specific embodiments of formula IA, $R_C$ is tetra-substitution at the 2-, 3-, 4- and 5-positions of the ring. In specific embodiments of formula IA, $R_C$ is penta-substitution of the ring. In specific embodiments of the forgoing embodiments, the substituents are all halogens. In specific embodiments of the forgoing embodiments, the substituents are all fluorines. In specific embodiments of the forgoing embodiments, the substituents are all chlorines. In specific embodiments of the forgoing embodiments, the substituents are all bromines. In specific embodiments of the forgoing embodiments, at least one substituent is iodine. In specific embodiments of the forgoing embodiments, the substituents are chlorines and nitro groups. In specific embodiments of the forgoing embodiments, n is 1 and L is —$CH_2$—.

In specific embodiments of formula IA, $R_C$ is one or two halogens. In specific embodiments of formula IA, $R_C$ is three halogens. In specific embodiments of formula IA, $R_C$ is four halogens. In specific embodiments of formula IA, $R_C$ is five halogens. In specific embodiments of formula IA, $R_C$ is a halogen substituted at the 4-position on the ring. In specific embodiments of formula IA, $R_C$ is a halogen substituted at the 2-position on the ring. In specific embodiments of formula IA, $R_C$ is a halogen substituted at the 3-position on the ring. In specific embodiments of formula IA, $R_C$ is two halogens substituted at the 2- and 4-positions on the ring. In specific embodiments of formula IA, $R_C$ is two halogens substituted at the 3- and 5-positions on the ring. In specific embodiments of formula IA, $R_C$ is two halogens substituted at the 3- and 4-positions on the ring. In specific embodiments of formula IA, $R_C$ is three halogens substituted at the 3-, 4- and 5-positions on the ring. In specific embodiments of formula IA, $R_C$ is three halogens substituted at the 2-, 3- and 4-positions on the ring. In more specific embodiments of the forgoing embodiments, the substituent halogen(s) are all fluorines. In more specific embodiments of the forgoing embodiments, the substituent halogen(s) are all chlorines. In specific embodiments of the forgoing embodiments, n is 1.

In more specific embodiments of formula IA, $R_C$ is a 4-iodo group. In more specific embodiments of formula IA, $R_C$ is a 4-bromo group. In more specific embodiments of formula IA, $R_C$ is a 4-chloro group. In more specific embodiments of formula IA, $R_C$ is a 4-fluoro group. In more specific embodiments of formula IA, $R_C$ is a chlorine at the 2-ring position. In more specific embodiments of formula IA, $R_C$ is a chlorine at the 3-ring position. In more specific embodiments of formula IA, $R_C$ is two chlorines at the 3- and 4-ring positions. In more specific embodiments of formula IA, $R_C$ is two fluorines at the 3- and 4-ring positions. In more specific embodiments of formula IA, $R_C$ is three chlorines at the 3-, 4- and 5-ring positions. In more specific embodiments of formula IA, $R_C$ is three fluorines at the 3-, 4- and 5-ring positions. In more specific embodiments of formula IA, $R_C$ is five fluorines. In specific embodiments of the forgoing embodiments, n is 1.

In specific embodiments of formula IA, $R_B$ or $R_C$, independently is an optionally substituted cycloalkyl group. In specific embodiments of formula IA, $R_B$ or $R_C$, independently is an optionally substituted $C_3$-$C_{10}$ cycloalkyl. In specific embodiments of formula IA, $R_B$ or $R_C$, independently is an optionally substituted $C_5$-$C_6$ cycloalkyl. In specific embodiments of formula IA, $R_B$ or $R_C$, independently is an optionally substituted cyclohexyl group. In specific embodiments of formula IA, $R_B$ or $R_C$, independently is a halogen-substituted cyclohexyl group. In specific embodiments of formula IA, $R_B$ or $R_C$, independently is an oxo-substituted cyclohexyl group. In specific embodiments of formula IA, $R_B$ or $R_C$, independently is a 4-oxo-substituted cyclohexyl group.

In specific embodiments of formula IA, $R_B$ or $R_C$, independently, is an optionally substituted aryl group. In specific embodiments of formula IA, $R_B$ or $R_C$, independently, is an optionally substituted phenyl group. In specific embodiments of formula IA, $R_B$ or $R_C$, independently, is an unsubstituted phenyl group. In specific embodiments of formula IA, $R_B$ or $R_C$, independently, is a phenyl group substituted with one or more halogens, nitro groups, cyano groups, hydroxyl groups, sulfhydryl groups, $C_1$-$C_3$ alkyl groups, $C_1$-$C_3$ alkoxy groups, $C_1$-$C_3$ thioalkyl groups. In specific embodiments of formula IA, $R_B$ or $R_C$, independently, is a phenyl group substituted with one to five halogens. In specific embodiments of formula IA, $R_B$ or $R_C$, independently, is a phenyl group substituted with one or two nitro groups or cyano group. In specific embodiments of formula IA, $R_B$ or $R_C$, independently, is a phenyl group substituted with one or two hydroxyl groups, sulfhydryl groups, $C_1$-$C_3$ alkyl groups, $C_1$-$C_3$ alkoxy groups, or $C_1$-$C_3$ thioalkyl groups. In specific embodiments of formula IA, $R_B$ or $R_C$, independently, is an benzyl group. In specific embodiments of formula IA, $R_B$ or $R_C$, independently, is an optionally substituted benzyl group. In specific embodiments of formula IA, $R_B$ or $R_C$, independently, is a benzyl group substituted with one or more halogens, nitro groups, cyano groups, hydroxyl groups, sulfhydryl groups, $C_1$-$C_3$ alkyl groups, $C_1$-$C_3$ alkoxy groups, $C_1$-$C_3$ thioalkyl groups. In specific embodiments of formula IA, $R_B$ or $R_C$, independently, is a benzyl group substituted with one to five halogens. In specific embodiments of formula IA, $R_B$ or $R_C$, independently, is a benzyl group substituted with one or two nitro groups or cyano group. In specific embodiments of formula IA, $R_B$ or $R_C$, independently, is a benzyl group substituted with one or two hydroxyl groups, sulfhydryl groups, $C_1$-$C_3$ alkyl groups, $C_1$-$C_3$ alkoxy groups, or $C_1$-$C_3$ thioalkyl groups. In specific embodiments of formula IA, $R_B$ or $R_C$, independently, is a biphenyl group.

In specific embodiments of formula IA, $R_B$, but not $R_C$ is an optionally substituted aryl group. In specific embodiments of formula IA, $R_C$, but not $R_B$ is an optionally substituted aryl group.

In specific embodiments of formula IA, $R_B$ or $R_C$, independently, is an optionally substituted heterocycyl group. In specific embodiments of formula IA, $R_B$ or $R_C$, independently, is an optionally substituted heterocycyl group having one or two 5- or 6-member rings which may be fused and having one or two heteroatoms selected from S, O or NR', where R' is hydrogen or a $C_1$-$C_6$ alkyl group. In specific embodiments of formula IA, the heterocycyl group of $R_B$ or $R_C$ is selected from:

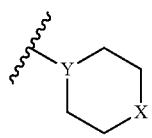

where Y is CH or N and X is S, O or NR'. In specific embodiments of formula IA, the heterocycyl group is at the 4-position of the ring.

In specific embodiments of formula IA, $R_B$, but not $R_C$ is an optionally substituted heterocycyl group. In specific embodiments of formula IA, $R_C$, but not $R_B$ is an optionally substituted heterocycyl group.

In specific embodiments of formula IA, $R_C$ is a halo group at the 4 ring position and $R_B$ is di-halo substitution. More specifically, $R_C$ is a 4-iodo group. More specifically, $R_B$ is 3-, 4-dihalo substitution on the ring. More specifically, $R_B$ is 3-, 4-dichloro-substitution on the ring.

In specific embodiments of formula IA, $R_B$ substituents on two adjacent carbons of the indicated ring together with the carbon s to which the substituents are attached form a carbocyclic or heterocyclic ring having 5 to 8 ring atoms thereby forming a fused ring. In specific embodiments of formula IA, $R_B$ substituents on two adjacent carbons of the indicated ring together with the carbon s to which the substituents are attached form a heterocyclic ring having 5 to 8 ring atoms thereby forming a fused ring. In these embodiments, the heteroatoms of the ring are particularly N, O or S. In an embodiment, the 5- to 8-member ring is an aromatic ring.

In specific embodiments of formula IA, $R_C$ substituents on two adjacent carbons of the indicated ring together with the carbon s to which the substituents are attached form a carbocyclic or heterocyclic ring having 5 to 8 ring atoms thereby forming a fused ring. In specific embodiments of formula IA, $R_C$ substituents on two adjacent carbons of the indicated ring together with the carbon s to which the substituents are attached form a heterocyclic ring having 5 to 8 ring atoms thereby forming a fused ring. In these embodiments, the heteroatoms of the ring are particularly N, O or S. In an embodiment, the 5- to 8-member ring is an aromatic ring.

In specific embodiments, the compound of the invention is that of formula IIA. In specific embodiments of formula IIA, n is 0, 1 or 2. In specific embodiments of formula IIA, n is 0. In specific embodiments of formula IIA, n is 1. In specific embodiments of formula IIA, n is 2.

In specific embodiments of formula IIA, R is an optionally substituted $C_1$-$C_6$ alkyl. In specific embodiments of formula IIA, R is an unsubstituted $C_1$-$C_6$ alkyl. In specific embodiments of formula IIA, R is an optionally substituted $C_1$-$C_6$ alkenyl. In specific embodiments of formula IIA, R is an unsubstituted $C_1$-$C_6$ alkenyl. In specific embodiments, R is a methyl, ethyl or propyl group including all isomers thereof. In specific embodiments, R is a $C_1$-$C_3$ haloalkyl group. In specific embodiments, R is a $C_1$-$C_3$ fluoroalkyl group. In specific embodiments, R is a —$CF_3$ group.

In specific embodiments of formula IIA, R is an optionally substituted aryl. In specific embodiments of formula IIA, R is an unsubstituted aryl. In specific embodiments of formula IIA, R is a phenyl group. In specific embodiments of formula IIA, R is a mono-substituted phenyl group. In specific embodiments of formula IIA, R is a 4-substituted phenyl group. In specific embodiments of formula IIA, R is a 2-substituted phenyl group. In specific embodiments of formula IIA, R is a mono- or di-substituted phenyl group. In specific embodiments of formula IIA where R is a substituted phenyl group, substituents include one or more halogen, nitro, $C_1$-$C_3$ alkyl, $C_1$-$C_3$ alkoxy, $C_1$-$C_3$-haloalkyl, or $C_1$-$C_3$-fluoralkyl.

In specific embodiments of formula IIA, R is a biphenyl group. In specific embodiments of formula IIA, R is a 4'-substituted biphenyl group. In specific embodiments of formula IIA, R is a naphthyl group. In specific embodiments of formula IIA, R is a naphth-1-yl group. In specific embodiments of formula IIA, R is a naphthyl-2-yl group.

In specific embodiments of formula IIA, R is an optionally substituted heteroaryl. In specific embodiments of formula IIA, R is an unsubstituted heteroaryl. In specific embodiments of formula IIA, R is an optionally substituted cycloalkyl. In specific embodiments of formula IIA, R is an unsubstituted cycloalkyl. In specific embodiments of formula IIA, R is an optionally substituted heterocycyl. In specific embodiments of formula IIA, R is an unsubstituted heterocycyl.

In specific embodiments of formula IIA, R is a phenyl group. In specific embodiments of formula IIA, R is a phenyl group.

In specific embodiments of formula IIA, R is a thiophenyl group. In specific embodiments of formula IIA, R is a thiophen-2-yl group. In specific embodiments of formula IIA, R is a thiophen-3-yl group. In specific embodiments of formula IIA, R is a furanyl group. In specific embodiments of formula IIA, R is a furan-2-yl group. In specific embodiments of formula IIA, R is a furan-3-yl group. In specific embodiments of formula IIA, R is a pyrrolyl group. In specific embodiments of formula IIA, R is a pyrrol-2-yl group. In specific embodiments of formula IIA, R is a pyrrol-3-yl group. In specific embodiments of formula IIA, R is a 2H-pyrrolyl group. In specific embodiments of formula IIA, R is a 2H-pyrrol-2-yl group. In specific embodiments of formula IIA, R is a 2H-pyrrol-3-yl group. In specific embodiments of formula IIA, R is an imidazolyl group. In specific embodiments of formula IIA, R is an imidazol-2-yl group. In specific embodiments of formula IIA, R is an imidazol-3-yl group.

In specific embodiments of formula IIA, R is a pyridinyl group. In specific embodiments of formula IIA, R is a pyridin-2-yl group. In specific embodiments of formula IIA, R is a pyridin-3-yl group. In specific embodiments of formula IIA, R is a pyridin-4-yl group. In specific embodiments of formula IIA, R is a pyrimidinyl group. In specific embodiments of formula IIA, R is a pyrimidin-2-yl group. In specific embodiments of formula IIA, R is a pyrimidin-4-yl group. In specific embodiments of formula IIA, R is a pyrimidin-5-yl group. In specific embodiments of formula IIA, R is a pyridazinyl group. In specific embodiments of formula IIA, R is a pyridazin-3-yl group. In specific embodiments of formula IIA, R is a pyridazin-4-yl group. In specific embodiments of formula IIA, R is a pyridazin-5-yl group. In specific embodiments of formula IIA, R is a pyrazinyl group. In specific embodiments of formula IIA, R is a pyrazin-2-yl group. In specific embodiments of formula IIA, R is a pyrazin-3-yl group. In specific embodiments of formula IIA, R is a pyranyl group. In specific embodiments of formula IIA, R is a pyran-2-yl group. In specific embodiments of formula IIA, R is a pyran-3-yl group. In specific embodiments of formula IIA, R is a pyran-5-yl group.

In specific embodiments of formula IIA, R is a haloallyl group (—CH═CH—$CH_2$—H, where H is F, Cl, Br or I). In specific embodiments of formula IIA, R is —CH═CH—$CH_2$—Cl or —CH═CH—$CH_2$—Br. In specific embodiments of formula IIA, R is an optionally substituted oxiranyl group. In specific embodiments of formula IIA, R is an unsubstituted oxiranyl group.

In specific embodiments of formula IIA, one of $R_B$ or $R_C$ is five hydrogen (i.e., one phenyl ring is unsubstituted) and the other of $R_B$ or $R_C$ caries at least one non-hydrogen substituent. In specific embodiments of formula IIA, $R_B$ is mono-substitution at the 4-position of the ring. In specific embodiments of formula IIA, $R_B$ is mono-substitution at the 3-position of the ring. In specific embodiments of formula IIA, $R_B$ is mono-substitution at the 3-position of the ring. In specific embodiments of formula IIA, $R_B$ is di-substitution at the 2- and 4-positions of the ring. In specific embodiments of formula IIA, $R_B$ is di-substitution at the 3- and 5-positions of the ring. In specific embodiments of formula IIA, $R_B$ is di-substitution at the 3- and 4-positions of the ring. In specific embodiments of formula IIA, $R_B$ is tri-substitution at the 2-, 3- and 4-positions of the ring. In specific embodiments of formula IIA, $R_B$ is tri-substitution at the 3-, 4- and 5-positions of the ring. In specific embodiments of formula IIA, $R_B$ is tetra-substitution at the 2-, 3-, 4- and 5-positions of the ring. In specific embodiments of formula IIA, $R_B$ is penta-substitution of the ring. In specific embodiments of the forgoing embodiments, the substituents are all halogens. In specific embodiments of the forgoing embodiments, the substituents are all fluorines. In specific embodiments of the forgoing embodiments, the substituents are all chlorines. In specific embodiments of the forgoing embodiments, the substituents are all bromines. In specific embodiments of the forgoing embodiments, the substituents are chlorines and nitro groups.

In specific embodiments of formula IIA, $R_B$ is one or two halogens, cyano groups, or nitro groups substituted on the ring. In specific embodiments of formula IIA, $R_B$ is one or two nitro groups. In specific embodiments of formula IIA, $R_B$ is a nitro group substituted at the 4-ring position. In specific embodiments of formula IIA, $R_B$ is a nitro group substituted at the 3-ring position. In specific embodiments of formula IIA, $R_B$ is a cyano group substituted at the 4-ring position. In specific embodiments of formula IIA, $R_B$ is a cyano group substituted at the 3-ring position. In specific embodiments of formula IIA, $R_B$ is a halogen at the 4-position of the ring. In specific embodiments of formula IIA, $R_B$ is a halogen at the 3-position of the ring. In specific embodiments of formula IIA, $R_B$ is a halogen at the 2-position of the ring. In specific embodiments of formula IIA, $R_B$ is two halogens at the 2- and 4-positions of the ring. In specific embodiments of formula IIA, $R_B$ is two halogens at the 3- and 4-positions of the ring. In specific embodiments of formula IIA, $R_B$ is three halogens at the 2-, 3- and 4-positions of the ring. In specific embodiments of formula IIA, $R_B$ is three halogens at the 3-, 4- and 5-positions of the ring. In embodiments of the forgoing embodiments, all halogens are fluorine. In embodiments of the forgoing embodiments, all halogens are chlorine. In embodiments of the forgoing embodiments, all halogens are bromine. In embodiments of the forgoing embodiments, at least one halogen is iodine.

In specific embodiments of formula IIA, $R_B$ is an iodine at the 4-position of the ring. In specific embodiments of formula IIA, $R_B$ is a fluorine at the 4-position of the ring. In specific embodiments of formula IIA, $R_B$ is a bromine at the 4-position of the ring. In specific embodiments of formula IIA, $R_B$ is a chlorine at the 4-position of the ring. In specific embodiments of formula IIA, $R_B$ is a chlorine at the 3-position of the ring. In specific embodiments of formula IIA, $R_B$ is a chlorine at the 2-position of the ring.

In specific embodiments of formula IIA, $R_B$ is two fluorines at the 2- and 4-positions of the ring. In specific embodiments of formula IIA, $R_B$ is two fluorines at the 3- and 4-positions of the ring. In specific embodiments of formula IIA, $R_B$ is two fluorines at the 3- and 5-positions of the ring. In specific embodiments of formula IIA, $R_B$ is two bromines at the 2- and 4-positions of the ring. In specific embodiments of formula IIA, $R_B$ is two bromines at the 3- and 4-positions of the ring. In specific embodiments of formula IIA, $R_B$ is two bromines at the 3- and 5-positions of the ring. In specific embodiments of formula IIA, $R_B$ is two chlorines at the 2- and 4-positions of the ring. In specific embodiments of formula IIA, $R_B$ is two chlorines at the 3- and 4-positions of the ring. In specific embodiments of formula IIA, $R_B$ is two chlorines at the 3- and 5-positions of the ring. In specific embodiments of formula IIA, $R_B$ is a nitro group at the 3-position of the ring and a chlorine at the 4-position of the ring.

In specific embodiments of formula IIA, $R_B$ a hydroxyl group at the 4-position of the ring. In specific embodiments of formula IIA, $R_B$ $C_1$-$C_3$ alkyl group at the 2-position of the ring. In specific embodiments of formula IIA, $R_B$ a $C_1$-$C_3$ alkyl group at the 2-position of the ring and a hydroxyl group at the 4-position of the ring. In specific embodiments of formula IIA, $R_B$ a $C_1$-$C_3$ alkoxy group at the 4-position of the ring. In specific embodiments of formula IIA, $R_B$ a $C_1$-$C_6$ alkyl group at the 4-position of the ring.

In specific embodiments of formula IIA, $R_C$ is mono-substitution at the 4-position of the ring. In specific embodiments of formula IIA, $R_C$ is mono-substitution at the 3-position of the ring. In specific embodiments of formula IIA, $R_C$ is mono-substitution at the 3-position of the ring. In specific embodiments of formula IIA, $R_C$ is di-substitution at the 2- and 4-positions of the ring. In specific embodiments of formula IIA, $R_C$ is di-substitution at the 3- and 5-positions of the ring. In specific embodiments of formula IIA, $R_C$ is di-substitution at the 3- and 4-positions of the ring. In specific embodiments of formula IIA, $R_C$ is tri-substitution at the 2-, 3- and 4-positions of the ring. In specific embodiments of formula IIA, $R_C$ is tri-substitution at the 3-, 4- and 5-positions of the ring. In specific embodiments of formula IIA, $R_C$ is tetra-substitution at the 2-, 3-, 4- and 5-positions of the ring. In specific embodiments of formula IIA, $R_C$ is penta-substitution of the ring. In specific embodiments of the forgoing embodiments, the substituents are all halogens. In specific embodiments of the forgoing embodiments, the substituents are all fluorines. In specific embodiments of the forgoing embodiments, the substituents are all chlorines. In specific embodiments of the forgoing embodiments, the substituents are all bromines. In specific embodiments of the forgoing embodiments, at least one substituent is iodine. In specific embodiments of the forgoing embodiments, the substituents are chlorines and nitro groups. In specific embodiments of the forgoing embodiments, n is 1 and L is —$CH_2$—.

In specific embodiments of formula IIA, $R_C$ is one or two halogens. In specific embodiments of formula IIA, $R_C$ is three halogens. In specific embodiments of formula IIA, $R_C$ is four halogens. In specific embodiments of formula IIA, $R_C$ is five halogens. In specific embodiments of formula IIA, $R_C$ is a halogen substituted at the 4-position on the ring. In specific embodiments of formula IIA, $R_C$ is a halogen substituted at the 2-position on the ring. In specific embodiments of formula IIA, $R_C$ is a halogen substituted at the 3-position on the ring. In specific embodiments of formula IIA, $R_C$ is two halogens substituted at the 2- and 4-positions on the ring. In specific embodiments of formula IIA, $R_C$ is two halogens substituted at the 3- and 5-positions on the ring. In specific embodiments of formula IIA, $R_C$ is two halogens substituted at the 3- and 4-positions on the ring. In specific embodiments of formula IIA, $R_C$ is three halogens substituted at the 3-, 4- and 5-positions on the ring. In specific embodiments of formula IIA, $R_C$ is three halogens substituted at the 2-, 3- and 4-positions on the ring. In more specific embodiments of the forgoing embodiments, the substituent halogen(s) are all fluorines. In more specific embodiments of the forgoing embodiments, the substituent halogen(s) are all chlorines. In specific embodiments of the forgoing embodiments, n is 1 and L is —$CH_2$—.

In more specific embodiments of formula IIA, $R_C$ is a 4-iodo group. In more specific embodiments of formula IIA, $R_C$ is a 4-bromo group. In more specific embodiments of formula IIA, $R_C$ is a 4-chloro group. In more specific embodiments of formula IIA, $R_C$ is a 4-fluoro group. In more specific embodiments of formula IIA, $R_C$ is a chlorine at the 2-ring position. In more specific embodiments of formula IIA, $R_C$ is a chlorine at the 3-ring position. In more specific embodiments of formula IIA, $R_C$ is two chlorines at the 3- and 4-ring positions. In more specific embodiments of formula IIA, $R_C$ is two fluorines at the 3- and 4-ring positions. In more specific embodiments of formula IIA, $R_C$ is three chlorines at the 3-, 4- and 5-ring positions. In more specific embodiments of formula IIA, $R_C$ is three fluorines at the 3-, 4- and 5-ring positions. In more specific embodiments of formula IIA, $R_C$ is five fluorines. In specific embodiments of the forgoing embodiments, n is 1 and L is —$CH_2$—.

In specific embodiments of formula IIA, $R_B$ or $R_C$, independently is an optionally substituted cycloalkyl group. In specific embodiments of formula IIA, $R_B$ or $R_C$, independently is an optionally substituted $C_3$-$C_{10}$ cycloalkyl. In specific embodiments of formula IIA, $R_B$ or $R_C$, independently is an optionally substituted $C_5$-$C_6$ cycloalkyl. In specific embodiments of formula IIA, $R_B$ or $R_C$, independently is an optionally substituted cyclohexyl group. In specific embodiments of formula IIA, $R_B$ or $R_C$, independently is a halogen-substituted cyclohexyl group. In specific embodiments of formula IIA, $R_B$ or $R_C$, independently is an oxo-substituted cyclohexyl group. In specific embodiments of formula IIA, $R_B$ or $R_C$, independently is a 4-oxo-substituted cyclohexyl group.

In specific embodiments of formula IIA, $R_B$ or $R_C$, independently, is an optionally substituted aryl group. In specific embodiments of formula IIA, $R_B$ or $R_C$, independently, is an optionally substituted phenyl group. In specific embodiments of formula IIA, $R_B$ or $R_C$, independently, is an unsubstituted phenyl group. In specific embodiments of formula IIA, $R_B$ or $R_C$, independently, is a phenyl group substituted with one or more halogens, nitro groups, cyano groups, hydroxyl groups, sulfhydryl groups, $C_1$-$C_3$ alkyl groups, $C_1$-$C_3$ alkoxy groups, $C_1$-$C_3$ thioalkyl groups. In specific embodiments of formula IIA, $R_B$ or $R_C$, independently, is a phenyl group substituted with one to five halogens. In specific embodiments of formula IIA, $R_B$ or $R_C$, independently, is a phenyl group substituted with one or two nitro groups or cyano group. In specific embodiments of formula IIA, $R_B$ or $R_C$, independently, is a phenyl group substituted with one or two hydroxyl groups, sulfhydryl groups, $C_1$-$C_3$ alkyl groups, $C_1$-$C_3$ alkoxy groups, or $C_1$-$C_3$ thioalkyl groups.

In specific embodiments of formula IIA, $R_B$ or $R_C$, independently, is a benzyl group. In specific embodiments of formula IIA, $R_B$ or $R_C$, independently, is an optionally substituted benzyl group. In specific embodiments of formula IIA, $R_B$ or $R_C$, independently, is a benzyl group substituted with one or more halogens, nitro groups, cyano groups, hydroxyl groups, sulfhydryl groups, $C_1$-$C_3$ alkyl groups, $C_1$-$C_3$ alkoxy groups, $C_1$-$C_3$ thioalkyl groups. In specific embodiments of formula IIA, $R_B$ or $R_C$, independently, is a benzyl group substituted with one to five halogens. In specific embodiments of formula IIA, $R_B$ or $R_C$, independently, is a benzyl group substituted with one or two nitro groups or cyano group. In specific embodiments of formula IIA, $R_B$ or $R_C$, independently, is a benzyl group substituted with one or two hydroxyl groups, sulfhydryl groups, $C_1$-$C_3$ alkyl groups, $C_1$-$C_3$ alkoxy groups, or $C_1$-$C_3$ thioalkyl groups. In specific embodiments of formula IIA, $R_B$ or $R_C$, independently, is a biphenyl group.

In specific embodiments of formula IIA, $R_B$, but not $R_C$ is an optionally substituted aryl group. In specific embodiments of formula IIA, $R_C$, but not $R_B$ is an optionally substituted aryl group.

In specific embodiments of formula IIA, $R_B$ or $R_C$, independently, is an optionally substituted heterocycyl group. In specific embodiments of formula IIA, $R_B$ or $R_C$, independently, is an optionally substituted heterocycyl group having one or two 5- or 6-member rings which may be fused and having one or two heteroatoms selected from S, O or NR', where R' is hydrogen or a $C_1$-$C_6$ alkyl group. In specific embodiments of formula IIA, the heterocycyl group of $R_B$ or $R_C$ is selected from:

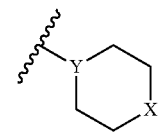

where Y is CH or N and X is S, O or NR'. In specific embodiments of formula IIA, the heterocycyl group is at the 4-position of the ring.

In specific embodiments of formula IIA, $R_B$, but not $R_C$ is an optionally substituted heterocycyl group. In specific embodiments of formula IIA, $R_C$, but not $R_B$ is an optionally substituted heterocycyl group.

In specific embodiments of formula IIA, $R_C$ is a halo group at the 4 ring position and $R_B$ is di-halo substitution. More specifically, $R_C$ is a 4-iodo group. More specifically, $R_B$ is 3-, 4-dihalo substitution on the ring. More specifically, $R_B$ is 3-, 4-dichloro-substitution on the ring.

In specific embodiments of formula IIA, $R_B$ substituents on two adjacent carbons of the indicated ring together with the carbon s to which the substituents are attached form a carbocyclic or heterocyclic ring having 5 to 8 ring atoms thereby forming a fused ring. In specific embodiments of formula IA, $R_B$ substituents on two adjacent carbons of the indicated ring together with the carbon s to which the substituents are attached form a heterocyclic ring having 5 to 8 ring atoms thereby forming a fused ring. In these embodiments, the heteroatoms of the ring are particularly N, O or S. In an embodiment, the 5- to 8-member ring is an aromatic ring.

In specific embodiments of formula IIA, $R_C$ substituents on two adjacent carbons of the indicated ring together with the carbon s to which the substituents are attached form a carbocyclic or heterocyclic ring having 5 to 8 ring atoms thereby forming a fused ring. In specific embodiments of formula IA, $R_C$ substituents on two adjacent carbons of the indicated ring together with the carbon s to which the substituents are attached form a heterocyclic ring having 5 to 8 ring atoms thereby forming a fused ring. In these embodiments, the heteroatoms of the ring are particularly N, O or S. In an embodiment, the 5- to 8-member ring is an aromatic ring.

Compounds of the invention include certain carboxylic acids, carboxylates and salts there of 2-aminothiazoles (formula III) and triazolothiadiazines, particularly 3,6,7-substituted-7H-[1,2,4]triazolo[3,4-b][1,3,4]thiadiazines (formula IV):

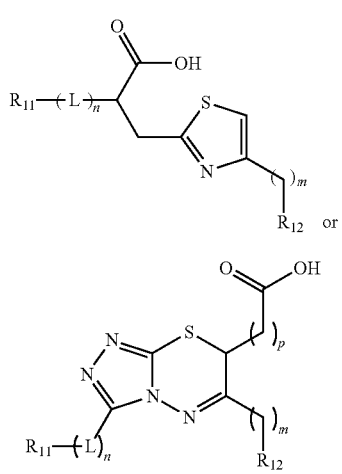

or salts thereof,
where:
n is 0 or 1 and L is L-$(CH_2)_q$— or —O—$(CH_2)_q$—, where q is 1, 2 or 3;
m and p, independently, are 0, 1, 2, or 3;
$R_{11}$ and $R_{12}$ are independently selected from an optionally substituted carbocyclyl, or an optionally substituted heterocyclyl with the proviso that one of $R_{11}$ or $R_{12}$ is an optionally substituted biphenyl group or an optionally substituted naphthyl group.

Optionally substitution is substitution as described herein. In specific embodiments optional substitution of biphenyl and napthyl groups includes substitution with one or more $C_1$-$C_3$ alkyl groups, $C_1$-$C_3$ alkoxy groups, halogens, amino (—$NH_2$), alkyl amino (—NHalkyl or —N(alkyl)$_2$), —COR', where R' is C1-C3 alkyl, $C_1$-$C_3$ haloalkyl (e.g., —$CF_3$), —CN or —$NO_2$. In more specific embodiments, substitution of biphenyl and naphthyl groups includes substitution with one or more methyl, methoxy, Cl, Br, I, —$COCH_3$, —$CF_3$, —CN or —$NO_2$. In specific embodiments, substitution of a biphenyl or naphthy group is substitution with one of the listed groups. In specific embodiments, substitution of a biphenyl or naphthy group is substitution with two of the listed groups. In specific embodiments, substitution of a biphenyl or naphthy group is substitution with three of the listed groups. In specific embodiments, substitution of a biphenyl or naphthy group is substitution with one, two or three halogens, particularly Cl. In specific embodiments, biphenyl substitution is substitution at the 4' or at both the 3' and 4' ring positions. Specific substituted biphenyl are 4'-halo biphenyl, 3',4'-dihalo biphenyl, 4'-Cl biphenyl, 3',4'-diCl biphenyl, 4'-Br-biphenyl, and 4'-I biphenyl. In specific embodiments, substituted naphthyl is substitution at any one, two or three of the 5, 6 or 7 ring positions. In specific embodiments, substituted naphthyl is substitution at the 5 and 6 ring positions. In specific embodiments, substituted naphthyl is substitution at the 6 ring position. Specific substituted naphthyl are 6-halo naphthyl, 6-Cl naphthyl, 6-Br naphthyl, 6-I naphthyl, 5,6-dihalo naphthyl, and 5,6-dichloro naphthyl.

In specific embodiments, optional substitution of phenyl and benzyl groups includes substitution with one or more $C_1$-$C_3$ alkyl groups, $C_1$-$C_3$ alkoxy groups, halogens, amino (—$NH_2$), alkyl amino (—NHalkyl or —N(alkyl)$_2$), —COR', where R' is $C_1$-$C_3$ alkyl, $C_1$-$C_3$ haloalkyl (e.g., —$CF_3$), —CN or —$NO_2$. In more specific embodiments, substitution of phenyl and benzyl groups includes substitution with one or more methyl, methoxy, Cl, Br, I, —$COCH_3$, —$CF_3$, —CN or —$NO_2$. In specific embodiments, substitution of a phenyl or benzyl group is substitution with one of the listed groups. In specific embodiments, substitution of a phenyl or benzyl group is substitution with two of the listed groups. In specific embodiments, substitution of a phenyl or benzyl group is substitution with three of the listed groups. In specific embodiments, substitution of a phenyl or benzyl group is substitution with one, two or three halogens, particularly Cl. In specific embodiments, phenyl or benzyl substitution is substitution at the 4' or at both the 3' and 4' ring positions. Specific substituted phenyl and benzyl are 4'-halo phenyl, 3',4'-dihalo phenyl, 4'-Cl phenyl, 3',4'-diCl phenyl, 4'-Br-phenyl, and 4'-I phenyl and 4'-halo benzyl, 3',4'-dihalo benzyl, 4'-Cl benzyl, 3',4'-diCl benzyll, 4'-Br benzyl, and 4'-I benzyl.

In specific embodiments of formulas III and IV, n is 1 and L is —$(CH_2)_q$—. In specific embodiments of formulas III and IV, n is 1 and L is —$(CH_2)$—. In specific embodiments of formulas III and IV, n is 1 and L is —$(CH_2)_2$—. In specific embodiments of formulas III and IV, n is 1 and L is —$(CH_2)_3$—. In specific embodiments of formulas III and IV, n is 1 and L is —O—$(CH_2)_q$—. In specific embodiments of formulas III and IV, n is 1 and L is —O—$(CH_2)_2$—. In specific embodiments of formulas III and IV, n is 1 and L is —O—$(CH_2)$—. In specific embodiments of formulas III and IV, n is 0.

In specific embodiments of formula III, m is 1. In specific embodiments of formula III, m is 2. In specific embodiments of formula III, m is 3. In specific embodiments of formula III, m is 0.

In specific embodiments of formula III, n is 1 and L is —O—$(CH_2)_2$—, m is 0 or 1 and p is 1 or 2. In specific embodiments of formula III, n is 1 and L is —$(CH_2)$—, and m is 0 or 1. In specific embodiments of formula III, n is 1, L is —$(CH_2)_2$—, and m is 0 or 1.

In specific embodiments of formula IV, n is 1 and L is —O—$(CH_2)_q$—. In specific embodiments of formula IV, n is 1 and L is —O—$(CH_2)_2$—. In specific embodiments of formulas IV, n is 1 and L is —O—$(CH_2)$—. In specific embodiments of formulas IV, n is 1 and L is —$(CH_2)_q$—. In specific embodiments of formula IV, n is 1 and L is —$(CH_2)$—. In specific embodiments of formula IV, n is 1 and L is —$(CH_2)_2$—. In specific embodiments of formula IV, n is 1 and L is —$(CH_2)_3$—. In specific embodiments of formula IV, n is 0.

In specific embodiments of formula IV, m is 1. In specific embodiments of formula IV, m is 2. In specific embodiments of formula IV, m is 3. In specific embodiments of formula IV, m is 0.

In specific embodiments of formula IV, p is 1. In specific embodiments of formula IV, p is 2. In specific embodiments of formula IV, p is 3. In specific embodiments of formula IV, p is 0.

In specific embodiments of formula IV, n is 1 and L is —O—(CH$_2$)$_2$—, m is 0 or 1 and p is 1 or 2. In specific embodiments of formula IV, n is 1 and L is —(CH$_2$)—, m is 0 or 1 and p is 1 or 2. In specific embodiments of formula IV, n is 1 and L is —(CH$_2$)$_2$—, m is 0 or 1 and p is 1 or 2.

In specific embodiments of formulas III or IV, R$_{11}$ or R$_{12}$ is an optionally substituted aryl or optionally substituted heteroaryl group having one or two rings, wherein when two rings of the group are present they are bonded through a single bond, e.g., a C—C bond, or are fused.

In specific embodiments of formulas III or IV, R$_{11}$ or R$_{12}$ is a heterocyclyl group having one or two rings and 1-4 heteroatoms, wherein when two rings of the group are present they are bonded through a single bond, e.g., a C—C bond, or are fused.

In specific embodiments of formulas III or IV, R$_{11}$ or R$_{12}$ is a heterocyclyl group having one ring and 1-3 heteroatoms. In specific embodiments of formulas III or IV, R$_{11}$ or R$_{12}$ is a heterocyclyl group having one 5 or 6-member ring and 1-3 heteroatoms. In specific embodiments of formulas III or IV, R$_{11}$ or R$_{12}$ is a heterocyclyl group having one or two 5- or 6-member ring and 1-4 heteroatoms, wherein when two rings of the group are present they are bonded through a single bond, e.g., a C—C bond, or are fused.

In specific embodiments of formulas III or IV, R$_{11}$ or R$_{12}$ is a heteroaryl group having one or two rings, wherein when two rings of the group are present they are bonded through a single bond, e.g., a C—C bond, or are fused.

In specific embodiments of formulas III or IV, R$_{11}$ or R$_{12}$ is a heteroaryl group having one 5- or 6-member ring and 1 or 2 heteroatoms. In specific embodiments, R$_{11}$ or R$_{12}$ is independently a heteroaryl group having one 5- or 6-member ring and 1 or 2 heteroatoms.

In specific embodiments of formulas III or IV, R$_{11}$ or R$_{12}$ is an optionally substituted aryl group. In specific embodiments, R$_{11}$ or R$_{12}$ is an optionally substituted phenyl group. In specific embodiments, R$_1$ or R$_2$ is an optionally substituted benzyl group. In specific embodiments, R$_{11}$ and/or R$_{12}$ is independently an optionally substituted biphenyl group. In specific embodiments, R$_{11}$ and/or R$_{12}$ is independently an optionally substituted naphthyl group In specific embodiments of formulas III or IV, R$_{11}$ and R$_{12}$ are optionally substituted aryl or heteroaryl groups having one or two rings or are alkyl groups substituted with an optionally substituted aryl, or heteroaryl group having one or two rings. In specific embodiments, the optionally substituted aryl, or heteroaryl groups have two fused rings. In specific embodiments, the optionally substituted aryl, or heteroaryl groups have two rings bonded through a single bond, e.g., a C—C bond.

In specific embodiments of formula III, R$_{11}$ is selected from furan-2-yl, furan-3-yl, 4-F-phenyl, 4-F-benzyl, thiophen-2-yl, thiophen-3-yl, 1-methylfuran-3-yl, 4-Cl-phenoxy-CH$_2$—, 2-methoxyphenyl, 4-F-phenyl, 4-F-benzyl, 4-Br-benzyl, 4-Br-phenyl, 4-Cl-phenyl, 4-Cl-benzyl, 1,1'-biphenyl-4-yl, 1,1'-biphenyl-3-yl, 1, l'-biphenyl-4-ylmethyl, 1,1'-biphenyl-3-ylmethyl, naphthalen-1-yl, naphthalene-2-yl, naphthalen-1-ylmethyl, and naphthalene-2-ylmethyl, with the proviso that one of R$_{11}$ or R$_{12}$ is an optionally substituted biphenyl group or an optionally substituted naphthyl group In specific embodiments of formula III, R$_{12}$ is selected from furan-2-yl, furan-3-yl, 4-F-phenyl, 4-F-benzyl, thiophen-2-yl, thiophen-3-yl, 1-methylfuran-3-yl, 4-Cl-phenoxy-CH$_2$—, 2-methoxyphenyl, 4-F-phenyl, 4-F-benzyl, 4-Br-benzyl, 4-Br-phenyl, 4-Cl-phenyl, 4-Cl-benzyl, 1,1'-biphenyl-4-yl, 1,1'-biphenyl-3-yl, 1,1'-biphenyl-4-ylmethyl, 1,1'-biphenyl-3-ylmethyl, naphthalen-1-yl, naphthalene-2-yl, naphthalen-1-ylmethyl, and naphthalene-2-ylmethyl with the proviso that one of R$_{11}$ or R$_{12}$ is an optionally substituted biphenyl group or an optionally substituted naphthyl group.

In specific embodiments of formula III, one of R$_{11}$ or R$_{12}$ is an unsubstituted biphenyl group. In specific embodiments of formula III, one of R$_{11}$ or R$_{12}$ is an unsubstituted naphthyl group. In specific embodiments of formula III, one of R$_{11}$ or R$_{12}$ is 1,1'-biphenyl-4-yl, 1,1'-biphenyl-3-yl, naphthalen-1-yl, or naphthalene-2-yl.

In specific embodiments of formula III or IV, R$_{11}$ is a different group from R$_{12}$.

In specific embodiments of formula III, R$_1$ is selected from 4-F-phenyl, 4-F-benzyl, 4-F-phenyl, 4-Cl-benzyl, 4-Cl-phenyl, 4-Br-benzyl, 4-Br-phenyl, thiophen-2-yl, phenyl, or 4-methylphenyl.

In specific embodiments of formula III, R$_{12}$ is selected from benzyl, phenethyl, 1,1'-biphenyl-4-yl, 1,1'-biphenyl-3-yl, 1,1'-biphenyl-4-ylmethyl, 1,1'-biphenyl-3-ylmethyl, naphthalen-1-yl, naphthalene-2-yl, naphthalen-1-ylmethyl, and naphthalene-2-ylmethyl.

In specific embodiments of formula III, R$_{12}$ is selected from 4-F-phenyl, 4-F-benzyl, 4-F-phenyl, 4-Cl-benzyl, 4-Cl-phenyl, 4-Br-benzyl, 4-Br-phenyl, thiophen-2-yl, phenyl, or 4-methylphenyl.

In specific embodiments of formula III, R$_{12}$ is selected from benzyl, phenethyl, 1,1'-biphenyl-4-yl, 1,1'-biphenyl-3-yl, 1,1'-biphenyl-4-ylmethyl, 1,1'-biphenyl-3-ylmethyl, naphthalen-1-yl, naphthalene-2-yl, naphthalen-1-ylmethyl, and naphthalene-2-ylmethyl.

In specific embodiments of formula III, one of R$_{11}$ or R$_{12}$ is selected from furan-2-yl, furan-3-yl, 4-F-phenyl, 4-F-benzyl, thiophen-2-yl, thiophen-3-yl, 1-methylfuran-3-yl, 4-Cl-phenoxy-CH$_2$—, 2-methoxyphenyl, 4-F-phenyl, 4-F-benzyl, 4-Br-benzyl, 4-Br-phenyl, 4-Cl-phenyl, and 4-Cl-benzyl and the other of R$_{11}$ or R$_{12}$ is an optionally substituted or unsubstituted biphenyl group or an optionally substituted or unsubstituted naphthyl group. In specific embodiments of formula III, the other one of R$_{11}$ or R$_{12}$ is 1,1'-biphenyl-4-yl, 1,1'-biphenyl-3-yl, naphthalen-1-yl, or naphthalene-2-yl each of which is optionally substituted.

Note that various embodiments of substituted phenyl groups are described with respect to the compounds of formula IA below and R$_{11}$ or R$_{12}$ can be any of such substituted phenyl groups, and particularly are halogen substituted phenyl groups.

In specific embodiments of formula IV, R$_{11}$ is selected from furan-2-yl, furan-3-yl, 4-F-phenyl, 4-F-benzyl, thiophen-2-yl, thiophen-3-yl, 1-methylfuran-3-yl, 4-Cl-phenoxy-CH$_2$—, 2-methoxyphenyl, 4-F-phenyl, 4-F-benzyl, 4-Br-benzyl, 4-Br-phenyl, 4-Cl-phenyl, 4-Cl-benzyl.

In specific embodiments of formula IV, R$_{12}$ is selected from furan-2-yl, furan-3-yl, 4-F-phenyl, 4-F-benzyl, thiophen-2-yl, thiophen-3-yl, 1-methylfuran-3-yl, 4-Cl-phenoxy-CH$_2$—, 2-methoxyphenyl, 4-F-phenyl, 4-F-benzyl, 4-Br-benzyl, 4-Br-phenyl, 4-Cl-phenyl, 4-Cl-benzyl.

In specific embodiments of formula IV, R$_{11}$ is selected from 4-F-phenyl, 4-F-benzyl, 4-F-phenyl, 4-Cl-benzyl, 4-Cl-phenyl, 4-Br-benzyl, 4-Br-phenyl, thiophen-2-yl, phenyl, or 4-methylphenyl.

In specific embodiments of formula IV, R$_{12}$ is selected from 4-F-phenyl, 4-F-benzyl, 4-F-phenyl, 4-Cl-benzyl, 4-Cl-phenyl, 4-Br-benzyl, 4-Br-phenyl, thiophen-2-yl, phenyl, or 4-methylphenyl.

In specific embodiments of formulas III or IV, R$_{11}$ is 4-I-phenyl. In specific embodiments of formula II, R$_1$ is 4-I-phenyl.

In specific embodiments of formulas III or IV, $R_{11}$ is 4-I-benzyl. In specific embodiments of formula I, $R_1$ is 4-I-benzyl.

In specific embodiments of formulas III or IV, $R_{11}$ is selected from p-F-phenyl, p-F-benzyl, p-F-phenyl, p-Cl-benzyl p-Cl-phenyl, p-Br-benzyl, p-Br-phenyl, thien-2-yl, phenyl, or p-methylphenyl.

In specific embodiments of formula III or IV, $R_{11}$ is 4-Br-phenyl-; 4-Cl-phenyl; 4-Cl-benzyl; 4-I-phenyl; 4-I-benzyl; 4-Br-phenoxy-$CH_2$—; 4-I-phenoxy-$CH_2$—; or 4-F-phenoxy-$CH_2$—.

In specific embodiments of formula III or IV, $R_{12}$ is p-halo-benzyl. In specific embodiments of formula III or IV, $R_{12}$ is 4-Br-benzyl. In specific embodiments of formula III or IV, $R_2$ is 4-I-benzyl. In specific embodiments of formula III or IV, $R_2$ is p-I-phenyl.

In specific embodiments of formula IV, one of $R_{11}$ or $R_{12}$ is selected from furan-2-yl, furan-3-yl, 4-F-phenyl, 4-F-benzyl, thiophen-2-yl, thiophen-3-yl, 1-methylfuran-3-yl, 4-Cl-phenoxy-$CH_2$—, 2-methoxyphenyl, 4-F-phenyl, 4-F-benzyl, 4-Br-benzyl, 4-Br-phenyl, 4-Cl-phenyl, 4-Cl-benzyl and the other of $R_{11}$ or $R_{12}$ is an optionally substituted or unsubstituted biphenyl group or an optionally substituted or unsubstituted naphthyl group. In specific embodiments of formula IV, the other of $R_{11}$ or $R_{12}$ is 1,1'-biphenyl-4-yl, 1,1'-biphenyl-3-yl, naphthalen-1-yl, or naphthalene-2-yl, each of which is optionally substituted.

Note that various embodiments of substituted phenyl groups are described with respect to the compounds of formula IA below and $R_1$ or $R_2$ can be any of such substituted phenyl groups.

In specific embodiments of formulas III or IV:

$R_{11}$ is optionally substituted biphenyl and $R_{12}$ is p-Br-benzyl, p-Cl-benzyl, p-I-benzyl, or p-halophenyl;

$R_{11}$ is optionally substituted biphenyl and $R_{12}$ is m, p-diclorophenyl;

$R_{11}$ is optionally substituted biphenyl and $R_{12}$ is p-F-benzyl, p-Cl-phenyl, p-Cl-benzyl, or p-Cl-phenoxy-;

$R_{11}$ is optionally substituted biphenyl and $R_{12}$ is p-Br-phenyl, p-Br-benzyl, p-Cl-phenyl, p-Cl-benzyl, p-I-phenyl or p-I-benzyl;

$R_{11}$ is optionally substituted biphenyl and $R_{12}$ is p-F-phenyl, p-F-benzyl, p-Cl-phenoxy-$CH_2$—, or thien-2-yl;

$R_{11}$ is optionally substituted biphenyl and $R_{11}$ is p-F-phenyl, p-F-benzyl, p-Cl-phenoxy-$CH_2$, thien-2-yl, p-Br-phenyl, p-Br-benzyl, p-I-phenyl, p-I-benzyl or p-Cl-benzyl.

$R_{11}$ is optionally substituted biphenyl and $R_{12}$ is fur-2-yl or thien-2-yl;

$R_{11}$ is optionally substituted biphenyl and $R_{12}$ is optionally substituted biphenyl or optionally substituted naphthyl;

$R_{12}$ is optionally substituted biphenyl and $R_{11}$ is p-Br-benzyl, p-Cl-benzyl, p-I-benzyl, or p-halophenyl;

$R_{12}$ is optionally substituted biphenyl and $R_{11}$ is m, p-diclorophenyl;

$R_{12}$ is optionally substituted biphenyl and $R_{11}$ is p-F-benzyl, p-Cl-phenyl, p-Cl-benzyl, or p-Cl-phenoxy-;

$R_{12}$ is optionally substituted biphenyl and $R_{11}$ is p-Br-phenyl, p-Br-benzyl, p-Cl-phenyl, p-Cl-benzyl, p-I-phenyl or p-I-benzyl;

$R_{12}$ is optionally substituted biphenyl and $R_{11}$ is p-F-phenyl, p-F-benzyl, p-Cl-phenoxy-$CH_2$—, or thien-2-yl;

$R_{12}$ is optionally substituted biphenyl and $R_{11}$ is p-F-phenyl, p-F-benzyl, p-Cl-phenoxy-$CH_2$, thien-2-yl, p-Br-phenyl, p-Br-benzyl, p-I-phenyl, p-I-benzyl or p-Cl-benzyl.

$R_{12}$ is optionally substituted biphenyl and $R_{11}$ is fur-2-yl or thien-2-yl; or $R_{12}$ is optionally substituted biphenyl and $R_{11}$ is optionally substituted biphenyl or optionally substituted naphthyl;

In specific embodiments of formulas III or IV, one of $R_1$ or $R_2$ is a dichloro-, difluoro- or dibromophenyl. In specific embodiments of formulas III or IV, one of $R_1$ or $R_2$ is a 2,4-dichloro-, 2,4-difluoro- or 2,4-dibromophenyl. In specific embodiments of formulas III or IV, one of $R_1$ or $R_2$ is a 3,3-dichloro-, 3,3-difluoro- or 3,3-dibromophenyl.

In specific embodiments, the $R_{11}$ or $R_{12}$ groups are optionally substituted phenyl rings. In specific embodiments, the $R_{11}$ or the $R_{12}$ groups are heteroaryl 6-member rings. In specific embodiments, the $R_{11}$ group or the $R_{12}$ group is a one or two 5- or 6-member carbocyclic or heterocyclic ring. In specific embodiments, the $R_{11}$ or $R_{12}$ groups are selected from pyridyl, indolyl, furanyl, purinyl, pyrazinyl, pyranyl, pyrimidinyl, thiophenyl, benzofuranyl, naphthyl or benzothiophenyl rings. In a specific embodiment, one of $R_{11}$ or $R_{12}$ is a phenyl rings and there is at least one non-hydrogen substituent the phenyl ring. In a specific embodiment, one of $R_{11}$ or $R_{12}$ is a heterocyclyl ring.

In specific embodiments of formulas III or IV, m is 0 or 1, n is 0 or 1 and p (if present is 1 or 2, where L if present is —$CH_2$—. In specific embodiments of formulas III or IV, m is 0 or 1, n is 0 or 1 and p (if present is 0 or 1, where L if present is —$CH_2$—, $R_{11}$ is unsubstituted biphenyl or unsubstituted naphthyl and $R_{12}$ is unsubstituted biphenyl, unsubstituted naphthyl, p-Cl-phenyl, p-Br-phenyl, p-I-phenyl or m, p-diclorophenyl. In specific embodiments of formulas III or IV, m is 0 or 1, n is 0 or 1 and p (if present is 1 or 2, where L if present is —$CH_2$—, $R_{12}$ is unsubstituted biphenyl or unsubstituted naphthyl and $R_{11}$ is unsubstituted biphenyl, unsubstituted naphthyl, p-Cl-phenyl, p-Br-phenyl, p-I-phenyl or m, p-diclorophenyl.

In specific embodiments of formula III, n is 0 or 1 and m is 0 or 1 and $R_{11}$ is unsubstituted biphenyl or substituted biphenyl and $R_{12}$ is a halo-substituted phenyl. More specifically $R_{12}$ is a 4-halo or a 3,4-dihalo substituted phenyl. More specifically $R_{12}$ is a 4-chloro phenyl, a 3,4-dichloro phenyl, a 4-Br phenyl or a 4-I phenyl. More specifically, $R_{11}$ is a 4'-halo or a 3'-4'-dihalo biphenyl, a 4'-Cl biphenyl, a 3',4'-dichloro biphenyl, a 4'-Br biphenyl or a 4'-I biphenyl.

In specific embodiments of formula III, n is 0 or 1 and m is 0 or 1 and $R_{11}$ is unsubstituted naphthyl or substituted naphthyl and $R_{12}$ is a halo-substituted phenyl. More specifically $R_{12}$ is a 4-halo or a 3,4-dihalo substituted phenyl. More specifically $R_{12}$ is a 4-chloro phenyl, a 3,4-dichloro phenyl, a 4-Br phenyl or a 4-I phenyl. More specifically, $R_{11}$ is a 6-halo naphthyl or a 5,6-dihalo naphthyl, a 6-Cl naphthyl, a 5,6-dichloro naphthyl, a 6-Br naphthyl or a 6-I naphthyl.

In specific embodiments of formula IV, p is 1, n is 0 or 1 and m is 0 or 1 and $R_{11}$ is unsubstituted biphenyl or substituted biphenyl and $R_{12}$ is a halo-substituted phenyl. More specifically $R_{12}$ is a 4-halo or a 3,4-dihalo substituted phenyl. More specifically $R_{12}$ is a 4-chloro phenyl, a 3,4-dichloro phenyl, a 4-Br phenyl or a 4-I phenyl. More specifically, $R_{11}$ is a 4'-halo or a 3'-4'-dihalo biphenyl, a 4'-Cl biphenyl, a 3',4'-dichloro biphenyl, a 4'-Br biphenyl or a 4'-I biphenyl.

In specific embodiments of formula IV, p is 1, n is 0 or 1 and m is 0 or 1 and $R_{11}$ is unsubstituted naphthyl or substituted naphthyl and $R_{12}$ is a halo-substituted phenyl. More specifically $R_{12}$ is a 4-halo or a 3,4-dihalo substituted phenyl. More specifically $R_{12}$ is a 4-chloro phenyl, a 3,4-dichloro phenyl, a 4-Br phenyl or a 4-I phenyl. More specifically, $R_{11}$ is a 6-halo naphthyl or a 5,6-dihalo naphthyl, a 6-Cl naphthyl, a 5,6-dichloro naphthyl, a 6-Br naphthyl or a 6-I naphthyl.

In embodiments, compounds include those of formula IIIA:

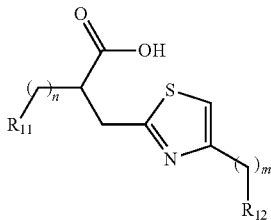

IIIA and salts thereof where n and m are independently 0 or 1 and $R_{11}$ and $R_{12}$ are as defined for formula III and one of $R_{11}$ or $R_{12}$ is an optionally substituted biphenyl or an optionally substituted naphthyl. In specific embodiments, one of $R_{11}$ or $R_{12}$ is an optionally substituted biphenyl. In specific embodiments, one of $R_{11}$ or $R_{12}$ is an unsubstituted biphenyl. In specific embodiments, n is 1 and $R_{11}$ is an unsubstituted biphenyl. In specific embodiments, n is 1, $R_{11}$ is an unsubstituted biphenyl, m is 0 or 1 and $R_{12}$ is a halogen substituted phenyl.

In embodiments, compounds include those of formula IVA:

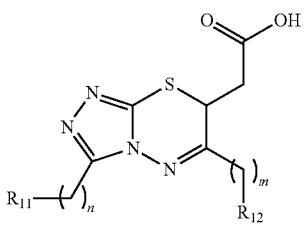

and salts thereof where n and m are independently 0 or 1 and $R_{11}$ and $R_{12}$ are as defined for formula III and one of $R_{11}$ or $R_{12}$ is an optionally substituted biphenyl or an optionally substituted naphthyl. In specific embodiments, one of $R_{11}$ or $R_{12}$ is an optionally substituted biphenyl. In specific embodiments, one of $R_{11}$ or $R_{12}$ is an unsubstituted biphenyl. In specific embodiments, n is 1 and $R_{11}$ is an unsubstituted biphenyl. In specific embodiments, n is 1, $R_{11}$ is an unsubstituted biphenyl, m is 0 or 1 and $R_{12}$ is a halogen substituted phenyl.

In embodiments, compounds include those of formula VA:

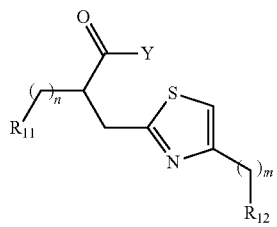

VA and salts thereof where Y is OH, or —NHSO$_2$R, n and m are independently 0 or 1 and $R_{11}$ and $R_{12}$ are as defined for formula III, R is an optionally substituted $C_1$-$C_6$ alkyl, an optionally substituted $C_1$-$C_6$ alkenyl, an optionally substituted alkoxy, an optionally substituted thioalkyl, an optionally substituted carbocyclyl, an optionally substituted heterocyclyl or an optionally substituted heteroaryl, and one of $R_{11}$ or $R_{12}$ is an optionally substituted biphenyl or an optionally substituted naphthyl. In specific embodiments, one of $R_{11}$ or $R_{12}$ is an optionally substituted biphenyl. In specific embodiments, one of $R_{11}$ or $R_{12}$ is an unsubstituted biphenyl. In specific embodiments, n is 1 and $R_{11}$ is an unsubstituted biphenyl. In specific embodiments, n is 1, $R_{11}$ is an unsubstituted biphenyl, m is 0 or 1 and $R_{12}$ is a halogen substituted phenyl.

In embodiments, compounds include those of formula VB:

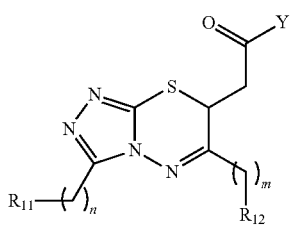

and salts thereof where Y is OH, or —NHSO$_2$R, n and m are independently 0 or 1 and $R_{11}$ and $R_{12}$ are as defined for formula IV, R is an optionally substituted $C_1$-$C_6$ alkyl, an optionally substituted $C_1$-$C_6$ alkenyl, an optionally substituted alkoxy, an optionally substituted thioalkyl, an optionally substituted carbocyclyl, an optionally substituted heterocyclyl or an optionally substituted heteroaryl, and one of $R_{11}$ or $R_{12}$ is an optionally substituted biphenyl or an optionally substituted naphthyl. In specific embodiments, one of $R_{11}$ or $R_{12}$ is an optionally substituted biphenyl. In specific embodiments, one of $R_{11}$ or $R_{12}$ is an unsubstituted biphenyl. In specific embodiments, n is 1 and $R_{11}$ is an unsubstituted biphenyl. In specific embodiments, n is 1, $R_{11}$ is an unsubstituted biphenyl, m is 0 or 1 and $R_{12}$ is a halogen substituted phenyl.

In specific embodiments of formula VA and VB, one of $R_{11}$ or $R_{12}$ is selected optionally substituted biphenyl or optionally substituted naphthyl and the other of $R_{11}$ or $R_{12}$ is selected from furan-2-yl, furan-3-yl, 4-F-phenyl, 4-F-benzyl, thiophen-2-yl, thiophen-3-yl, 1-methylfuran-3-yl, 4-Cl-phenoxy-CH$_2$—, 2-methoxyphenyl, 4-F-phenyl, 4-F-benzyl, 4-Br-benzyl, 4-Br-phenyl, 4-Cl-phenyl, 4-Cl-benzyl, 4-I phenyl, or 4-I-benzyl In specific embodiments, R of any formulas herein include among others, optionally substituted phenyl, unsubstituted phenyl, optionally substituted benzyl, unsubstituted benzyl, unsubstituted alkyl, unsubstituted $C_1$-$C_3$ alkyl, methyl, ethyl, optionally substituted thiophenyl, halogenated thiophenyl, chlorinated thiophenyl, optionally substituted imidazolyl, or alkyl substituted imidazolyl. Specific optional substitution includes substitution with a halogen, particularly a chlorine, or $C_1$-$C_3$ alkyl groups, particularly a methyl group. More specific R groups include unsubstituted phenyl, unsubstituted benzyl, 4-halo phenyl, 4-nitrophenyl, 4-halo benzyl, 4-nitrobenzyl, 3,4-dihalophenyl, 3,4-dihalo benzyl, 3,4-dichlorophenyl, 3,4-dichloro benzyl, thien-2-yl, 5-halogenated thien-2-yl, 5-Cl-thien-2-yl, thien-3-yl, imidazol-4-yl, imidazol-3-yl, imidazol-2-yl, 1-alkyl imidazol-4-yl, and 1-methylimidazol-4-yl.

In more specific embodiments, the invention provides compounds of formulas I or II or salts thereof,
wherein
n is 0 or 1 and L is —$(CH_2)_q$— or —O—$(CH_2)_q$—, where q is 1, 2 or 3;
m and p, independently, are 0, 1, 2, or 3;
R is an optionally substituted $C_1$-$C_6$ alkyl, an optionally substituted $C_1$-$C_6$ alkenyl, an optionally substituted alkoxy, an optionally substituted thioalkyl, an optionally substituted carbocyclyl, or an optionally substituted heterocyclyl;
$R_1$ and $R_2$ are independently selected from optionally substituted carbocyclyl, and optionally substituted heterocyclyl; and
wherein optional substitution is substitution by one or more non-hydrogen substituents selected from halogen, hydroxyl, mercapto, nitro, cyano, azide, isocyano, thiocyano, oxo, optionally substituted $C_1$-$C_3$ alkyl, optionally substituted $C_1$-$C_3$-alkenyl, optionally substituted $C_1$-$C_3$ alkoxy, acyl, halogenated phenyl, nitrophenyl, alkoxyphenyl, thioalkyl, optionally substituted heteroaryl, optionally substituted cycloalkyl, optionally substituted heterocyclyl, —$SO_2$—N$(R_S)_2$, —$SO_2$—$R_S$, —$COOR_S$, —$COR_S$, —$CON(R_S)_2$, —$N(R_S)_2$, where $R_S$ is hydrogen, $C_1$-$C_3$ alkyl, $C_1$-$C_3$ alkenyl, $C_1$-$C_3$ haloalkyl, $C_1$-$C_3$ haloalkoxy, phosphate, phosphonate, or carboxyl.

In specific embodiments, of formula I, n is 0 or 1 and m is 0 or 1. More specifically, n is 1 and m is 0 or n is 1 and m is 1, or n is 0 and m is 0 or n is 1 and m is 1.

In specific embodiments, of formulas I and II, $R_1$ and $R_2$ are independently selected from phenyl, biphenyl, naphthyl or heteroaryl, wherein each of these groups are optionally substituted with one or more halogen, nitro, cyano, $C_1$-$C_3$ alkyl, $C_1$-$C_3$ alkoxy, acyl, or $C_1$-$C_3$ haloalkyl; or $R_1$ and $R_2$ are independently selected from phenyl, biphenyl, or heteroaryl, wherein each of these groups are optionally substituted with one or more halogen, nitro, methyl, methoxy, acetyl or trifluormethyl.

In specific embodiments, of formulas I and II, $R_1$ and $R_2$ are different groups.

In specific embodiments, of formulas I and II, one of $R_1$ and $R_2$ are selected from optional optionally substituted biphenyl, or optionally substituted naphthyl and the other of R1 or R2 is selected from optionally substituted phenyl or optionally substituted heteroaryl, wherein optionally substituted is substitution with one or more halogen, nitro, methyl, methoxy, acetyl or trifluormethyl groups.

In specific embodiments of formula II p is 1, n is 0 or 1 and m is 0 or 1.

In specific embodiments of formulas I or II, $R_1$ is 4-bromo phenyl, 4-iodo phenyl, napthyl, or biphenyl and $R_2$ is 4-bromophenyl, 4-iodo phenyl, 4-chlorophenyl, 3,4-dichlorophenyl or biphenyl.

The invention provides a method for inhibiting UGM which comprises contacting UGM with an amount of one or more compounds or salts of formula I or II as in preceding embodiments effective for inhibiting the enzyme. More specifically, the UGM is that of a *mycobacterium* or a nematode.

The invention provides a method for inhibiting the growth of a microorganism which comprises contacting the microorgnism or an environment containing the microorganism with an effective amount of one or more compounds or salts formulas I or II in the preceding embodiments. More specifically the microorganism is a bacterium, a fungus, an algae or a nematode.

The invention provides a method of treating an infection by a microorganism having UGM in an individual in need of such treatment by administering to the individual an effective amount of one or more compounds formulas I or II as in preceding embodiments. More specifically is an infection of a bacterium, a fungus, an algae or a nematode. More specifically the infection is tuberculosis.

In more specific embodiments, the invention provides compounds of formula VA or VB:
and salts thereof,
where Y is OH, or —$NHSO_2R$;
n and m are independently 0 or 1;
R is an optionally substituted $C_1$-$C_6$ alkyl, an optionally substituted $C_1$-$C_6$ alkenyl, an optionally substituted alkoxy, an optionally substituted thioalkyl, an optionally substituted carbocyclyl, or an optionally substituted heterocyclyl; and
$R_{11}$ and $R_{12}$ are selected from an optionally substituted carbocyclyl, or an optionally substituted heterocyclyl, wherein one of $R_{11}$ or $R_{12}$ is an optionally substituted biphenyl or an optionally substituted naphthyl; and
wherein optional substitution is substitution with one or more halogen, $C_1$-$C_3$ alkyl, $C_1$-$C_3$ alkoxy, nitro, cyano, acyl, or halogenated $C_1$-$C_3$ alkyl.

In more specific embodiments, the invention provides compounds of formula VA or VB and salts thereof as in the preceding embodiment,
wherein one of $R_{11}$ or $R_{12}$ is an substituted biphenyl or an unsubstituted naphthyl; or
wherein $R_{11}$ and $R_{12}$ are selected from optionally substituted phenyl, optionally substituted biphenyl, optionally substituted naphthyl or optionally substituted heteroaryl; or
wherein one of $R_{11}$ or $R_{12}$ is an optionally substituted biphenyl and the other of $R_{11}$ or $R_{12}$ is selected from furan-2-yl, furan-3-yl, thiophen-2-yl, thiophen-3-yl, 1-methylfuran-3-yl, 4-methylphenyl, 4-methoxyphenyl, 4-fluorophenyl, 4-bromophenyl, 4-chlorophenyl, or 4-iodophenyl.

In specific embodiments, of formulas VA or VB, $R_1$ and $R_2$ are different groups.

In more specific embodiments, the invention provides compounds of formula VA or VB and salts thereof as in the preceding embodiments:
where R is selected from unsubstituted $C_1$-$C_3$ alkyl, $C_1$-$C_3$ haloalkyl, unsubstituted phenyl, phenyl substituted with one or more halogen, nitro substituted phenyl, thien-2-yl, halogenated thien-2-yl, thien-3-yl, halogenated thien-3-yl, imidazol-4-yl, imidazol-3-yl, imidazol-2-yl, and 1-alkyl imidazol-4-yl.

The invention provides a pharmaceutically acceptable composition which comprises one or more compounds or salts of compounds of formulas Va or VB as in preceding embodiments and a pharmaceutically acceptable carrier.

The invention provides a method for inhibiting UGM which comprises contacting UGM with an amount of one or more compounds or salts of formula VA or Vb as in the preceding embodiments effective for inhibiting the enzyme. Contacting the microorgnism includes contacting an environment containing the microorganism with an effective amount of the one or more compounds. More specifically, the UGM is that of a *mycobacterium* or a nematode.

The invention provides a method for inhibiting the growth of a microorganism which comprises contacting the microorgnism or an environment containing the microorganism with an effective amount of one or more compounds or salts formulas VA or VB as in the preceding embodiments. More specifically the microorganism is a bacterium, a fungus, an algae or a nematode.

The invention provides a method of treating an infection by a microorganism having UGM in an individual in need of such treatment by administering to the individual an effective amount of one or more compounds formulas VA or VB as in preceding embodiments. More specifically is an infection of a bacterium, a fungus, an algae or a nematode. More specifically the infection is tuberculosis.

Novel compounds of the invention can be prepared by one of ordinary skill in the art employing synthetic methods that are well-known in the art or by routine adaptation of such methods from starting material and reagents that are available commercially or readily prepared by well-known methods. Methods useful in the preparation of compounds of the invention of formulas I and II can be found in the following references each of which is incorporated by reference herein in its entirety for the synthetic methods therein:

U.S. Pat. No. 8,273,778, U.S. published application 2015/0344501, Dhindsa, G. S.; Vaid, R. K. (1986) Synthesis and mass spectral studies of some 3-alkyl-6-aryl-7-carbethoxy/carboxy-methyl-s-triazolo[3,4-b][1,3,4]thiadiazines Indian Journal of Chemistry, Section B: Organic Chemistry Including Medicinal Chemistry 25B(3), 283-7; Mazzone, G.; Bonina, F et al. (1989) Carboxymethyl- and carboxy-derivatives of 7H- and 5H-1,2,4-triazolo[3,4-b][1,3,4]thiadiazine: synthesis and biological evaluation Farmaco 44(10), 933-44; Jakhar, A., Makrandi, J. K. (2012) Molecular iodine mediated one step synthesis and antibacterial properties of some 3-aryl-6-(6-substituted-4-methylcinnolin-3-yl)-7H-1,2,4-triazolo[3,4-b][1,3,4]thiadiazines Indian Journal of Chemistry, Section B: Organic Chemistry Including Medicinal Chemistry 51B(1), 313-317; Aytac, S. P; Tozkoparan, B, Kaynak, et al. (2009) Synthesis of 3,6-disubstituted 7H-1,2,4-triazolo[3,4-b]-1,3,4-thiadiazines as novel analgesic/anti-inflammatory compounds European Journal of Medicinal Chemistry 44(11), 4528-4538; WO 2009089027 A1 20090716; El-Serwy W. S. et al. (2013) Res. Chem. Intermed. 39:2543-2554; and Vovk, M. et al. (2010) Molecules 15:997-1006.

The invention provides a method for inhibiting UGM in vitro or in vivo by contacting a biological composition comprising an active UGM with an amount of one or more of the compounds of any of the formulas herein effective for inhibiting UGM. In a specific embodiment, the inhibition of UGM is in vivo in a prokaryote. In a specific embodiment, the inhibition of UGM is in vivo in a eukaryote. In a specific embodiment, the inhibition of UGM is in vivo in a nematode.

The invention also provides a method for inhibiting the growth of a microorganism containing UGM by contacting the microorganism with an amount of one or more of the compounds of any of the formulas herein effective for inhibiting the growth of the microorganism. In a specific embodiment, the microorganism is a human or veterinary pathogen. In a specific embodiment, the microorganism is a bacterium. In another embodiment, the microorganism is of the genus *Mycobacterium*. In more specific embodiments, the microorganism is *Mycobacterium tuberculosis* or *Mycobacterium smegmatis*. In another embodiment, the microorganism is of the genus *Klebsiella*, including *Klebsiella pneumoniae*. In other embodiments, the microorganism is a prokaryote or a eukaryote.

The invention also provides a method for attenuating the virulence of a microorganism containing UGM by contacting the microorganism with an amount of one or more of the compounds of any of the formulas herein effective for attenuating virulence of the microorganism. In a specific embodiment, the microorganism is a human or veterinary pathogen. In a specific embodiment, the microorganism is a bacterium. In another embodiment, the microorganism is of the genus *Mycobacterium*. In more specific embodiments, the microorganism is *Mycobacterium tuberculosis* or *Mycobacterium smegmatis*. In another embodiment, the microorganism is of the genus *Klebsiella*, including *Klebsiella pneumoniae*. In other embodiments, the microorganism is a prokaryote or a eukaryote.

The invention also provides a method for inhibiting the growth of a microorganism containing UGM by contacting the microorganism with an amount of one or more of the compounds of any of the formulas herein effective for inhibiting UGM. In a specific embodiment, the microorganism is a human or veterinary pathogen. In a specific embodiment, the microorganism is a bacterium. In another embodiment, the microorganism is of the genus *Mycobacterium*. In more specific embodiments, the microorganism is *Mycobacterium tuberculosis* or *Mycobacterium smegmatis*. In another embodiment, the microorganism is of the genus *Klebsiella*, including *Klebsiella pneumoniae*. In other embodiments, the microorganism is a prokaryote or a eukaryote.

The invention further provides a method of treating a human, a non-human mammal or a non-human animal individual having or believed to have an infection of a microorganism containing UGM by administering to the individual an amount of one or more compounds of any of the formulas herein effective for inhibiting the growth of the microorganism. In specific embodiments, the microorganism is a bacterium or a *mycobacterium*. In specific embodiments, the mycobacterial infection is tuberculosis. In specific embodiments, the microorganism is of the genus *Mycobacterium* or *Klebsiella*. In additional embodiments, the microorganism is *Mycobacterium tuberculosis, Mycobacterium smegmatis* or *Klebsiella pneumoniae*. The pathogenic microorganism can be a prokaryote or a eukaryote.

The invention additionally provides a method for treating a human, a non-human mammal or a non-human animal individual having or believed to have an infection of a microorganism containing UGM by administering an effective amount of a compound of this invention of any of the formulas herein, in combination with an antibiotic or antiparasitic agent appropriate for treatment of the infection. Compounds of this invention can enhance the effectiveness of art-known antibiotics and are useful in combination therapy in addition to such antibiotics. The compounds of the present invention can, for example, be employed in combination therapy with antibiotics, such as ethambutol, isoniazid, rifampicin, and pyrazinamide. Such combination therapy is particularly useful in the treatment of mycobacterial infections.

The invention further provides a method of treating a human, a non-human mammal or a non-human animal individual having or believed to have an infection of a parasitic pathogen containing UGM by administering to the individual an amount of one or more compounds of any of the formulas herein effective for inhibiting the growth of the parasitic pathogen. In specific embodiments, the parasitic pathogen is a protozoan or a nematode. In a related embodiment, the treatment method includes administering an effective amount of a compound of this invention of any of the formulas herein, in combination with antiparasitic agent appropriate for treatment of the infection. The compounds of the present invention can, for example, be employed in combination therapy with antiparasitic agent, particularly anthelminthic agents, such as diethylcarbamazine, teracyclies, rifampicin, chloramphenicol, alendazole, mebendazole, levamisole, pyrantel and ivermectic or combinations of two or more thereof. Such combination therapy is particularly useful in the treatment of nematode infections.

The invention additional provides a medicament comprising one or more compounds of the formulas herein effective for inhibiting the growth of a microorganism, including a eukaryotic parasite, or effective for attenuating the virulence of a microorganism, including a eukaryotic parasite, which contains UGM. The invention additional provides a medicament comprising one or more compounds of any of the formulas herein effective for inhibiting UGM. In specific embodiments, the microorganism is a bacterium or a *mycobacterium*. In specific embodiments, the microorganism is of the genus *Mycobacterium* or *Klebsiella*. In additional embodiments, the microorganism is *Mycobacterium tuberculosis*, *Mycobacterium smegmatis* or *Klebsiella pneumoniae*. In additional embodiments, the invention provides a medicament comprising one or more compounds of the formulas herein effective for inhibiting the growth of a protozoan or effective for attenuating the virulence of a protozoan which contains UGM. The invention additional provides a medicament comprising one or more compounds of any of the formulas herein effective for inhibiting UGM of a protzoan. In specific embodiments, the protozoan are among others. *Plasmodium*, Trypanosomes and *Leishmania*. In additional embodiments, the invention provides a medicament comprising one or more compounds of the formulas herein effective for inhibiting the growth of a nematode or effective for attenuating the virulence of a nematode which contains UGM. The invention additional provides a medicament comprising one or more compounds of any of the formulas herein effective for inhibiting UGM of a nematode. Nematode include among others, *Ancylostoma, Necator, Ascaris, Strongyloides, Trichinella, Capillaria, Toxocara, Toxascaris, Trichuris, Enterobius, Onchocerca, Brugia, Wuchereria*, or *Dracunculus*.

The invention also provides a method of making a medicament for treating an individual (human, mammal or animal) having a bacterial or mycobacterial infection. In specific embodiments, the mycobacterial infection is tuberculosis. In specific embodiments, the microorganism is of the genus *Mycobacterium* or *Klebsiella*. In additional embodiments, the microorganism is *Mycobacterium tuberculosis*, *Mycobacterium smegmatis* or *Klebsiella pneumoniae*. In a specific embodiment, the method of making a medicament includes the step of combining an amount of a compound of any of the formulas herein with a pharmaceutically effective carrier. In a specific embodiment, the medicament is in a dosage form appropriate for oral administration, topical administration or administration by injection.

In specific embodiments, the invention also provides compounds of any of the formulas herein which inhibit the growth of a microorganism having UGM which exhibit a dissociation constant K for the UGM enzyme of 100 μM or less. In another embodiment, the compound exhibits a dissociation constant K for the UGM enzyme of 50 μM or less. In another embodiment, the compound exhibits a dissociation constant K for the UGM enzyme of 25 μM or less. In another embodiment, the compound exhibits a dissociation constant K for the UGM enzyme of 10 μM or less. In further embodiments, the microorganism is a *Mycobacterium*, particularly *Mycobacterium tuberculosis*. In additional embodiments the microorganism is of the genus *Klebsiella*.

In specific embodiments, the invention provides compound of any formulas herein which exhibit Kd (μM) on $UGM_{myco}$ of 100 or less. In other embodiments, the invention provides compound of any formulas herein which exhibit Kd (μM) on $UGM_{myco}$ of 80 or less. In other embodiments, the invention provides compound of any formulas herein which exhibit Kd (μM) on $UGM_{myco}$ of 60 or less. In other embodiments, the invention provides compounds of any formulas herein which exhibits exhibit Kd (μM) as measured by the fluorescence polarization assay on the UGM isoform from *M. tuberculosis* of 25 or less.

In specific embodiments, the invention provides compounds of any formulas herein which exhibit Kd (μM) as measured by the fluorescence polarization assay on the UGM isoform from *K. pneumoniae* of 80 or less. In other embodiments, the invention provides compounds of any formulas herein which exhibit Kd (μM) as measured by the fluorescence polarization assay on the UGM isoform from *K. pneumoniae* of 60 or less. In other embodiments, the invention provides compounds of any formulas herein which exhibit Kd (μM) as measured by the fluorescence polarization assay on the UGM isoform from *K. pneumoniae* of 25 or less.

The invention further provides a method for inhibiting UGM in vitro or in vivo by contacting a biological composition comprising an active UGM with an amount of one or more of the compounds of any of the formulas herein effective for inhibiting UGM. In a specific embodiment, the inhibition of UGM is in vivo in a prokaryote. In a specific embodiment, the inhibition of UGM is in vivo in a eukaryote.

In specific embodiments, the invention provides pharmaceutically acceptable compositions which comprise one or more compounds of formulas IA, IIA, IIIA or IVA and a pharmaceutically acceptable excipient. In specific embodiments, the excipient is other than water. In specific embodiments, the excipient is other than a solvent.

The invention provides methods for inhibiting UGM comprising contacting UGM with an amount of one or more of the compounds of formulas IA, IIA, IIIA or IVA which is effective for inhibiting the enzyme.

The invention provides a method for inhibiting incorporation of Galf into a microbial polysaccharide which comprises contacting the microorganism or an environment containing the microorganism with an amount one or more compounds of formulas IA, IIA, IIIA or IVA effective for such inhibition.

The invention also provides methods for inhibiting the growth of mycobacteria which comprises contacting the mycobacteria or an environment containing the mycobacteria with an amount of one or more compounds of formulas IA, IIA, IIIA or IVA effective for such growth inhibition.

The invention also provides methods for treatment of a mycobacterial infection which comprises administering to a human or non-human subject in need of such treatment an amount of one or more compounds of formulas IA, IIA, IIIA or IVA effective for such treatment. In a specific embodiment, the mycobacterial infection is tuberculosis.

In specific embodiments, the invention provides pharmaceutically acceptable compositions which comprise one or more compounds of formulas VA or VB and a pharmaceutically acceptable excipient. In specific embodiments, the excipient is other than water. In specific embodiments, the excipient is other than a solvent.

The invention provides methods for inhibiting UGM comprising contacting UGM with an amount of one or more of the compounds of formulas VA or VB which is effective for inhibiting the enzyme.

The invention provides a method for inhibiting incorporation of Galf into a microbial polysaccharide which comprises contacting the microorganism or an environment containing the microorganism with an amount one or more compounds of formulas VA or VB effective for such inhibition.

The invention also provides methods for inhibiting the growth of mycobacteria which comprises contacting the mycobacteria or an environment containing the mycobacteria with an amount of one or more compounds of formulas VA or VB effective for such growth inhibition.

The invention also provides methods for treatment of a mycobacterial infection which comprises administering to a human or non-human subject in need of such treatment an amount of one or more compounds of formulas VA or VB effective for such treatment. In a specific embodiment, the mycobacterial infection is tuberculosis.

Compounds of the invention are useful for inhibiting the growth of a microorganism containing UGM which is the enzyme responsible for the conversion of UDP-galactopyranose to UDP-galactofuranose. UGM is expected to be present in microorganisms in which galactofuranose (Galf) residues are present, for example in cell walls. Galactofuranose (Galf) residues are present in many pathogenic microorganisms (Pedersen, L. L.; Turco, S. J. Cell. Mol. Life Sci. 2003, 60, 259-266.) The gene encoding UGM is essential for mycobacterial viability (Pan, F.; Jackson, M.; Ma, Y. F.; McNeil, M. J. Bacteriol. 2001, 183, 3991-3998) suggesting that Galf-containing glycoconjugates are necessary components of the mycobacterial cell wall. Compounds of the invention are useful for inhibiting the growth of microorganisms containing galactofuranose residues, particularly those having such residues in the cell wall and more particularly pathogenic microorganisms containing galactofuranose residues.

Compounds of the invention are useful for inhibition of growth of microorganisms of the genus *Mycobacterium*, particularly including *M. tuberculosis* and *M. smegmatis*. Compounds of the invention can also be employed to inhibit the growth of *Mycobacterium leprae, Mycobacterium bovis, Mycobacterium africanum, Mycobacterium canetti,* and *Mycobacterium microti*.

Compounds of the invention are useful for inhibition of the growth of Gram-negative bacteria and particularly those of the genus *Klebsiella* and particularly *K. pneumoniae*. The compounds of the invention can also be employed to inhibit the growth of *Klebsiella ozaenae, Klebsiella rhinoscleromatis, Klebsiella oxytoca, Klebsiella planticola, Klebsiella terrigena,* and *Klebsiella ornithinolytica*. Klebsiellae are important pathogens in nosocomial infections. The compounds of the invention are useful for the treatment of nosocomial infections.

Compounds of the invention are useful for inhibition of the growth of or for attenuation of the virulence of eukaryotic pathogens, including yeast, fungi, protozoa and nematodes. The compounds of the invention are useful for inhibiting the growth or attenuating the virulence of, for example, pathogenic *Aspergillus*, in particular *Aspergillus fumagatus*.

The term "microorganism" is used broadly herein to refer to organisms too small to be seen with the naked human eye and includes prokaryotes (e.g., bacteria and mycobacteria), single cell and multiple cell eukaryotes, yeast, fungi and protozoa. More specifically microorganisms upon which the compounds of this invention act are human or non-human mammal pathogens. Pathogenic protozoa include, among others, *Plasmodium*, Trypanosomes and *Leishmania* (e.g., *Leishmania major, Trypanosoma cruizii*.) Fungi include *Cryptococcus* (e.g., *Cryptococcus neoformans*). Microorganism also includes nematodes and more specifically parasitic nematodes.

Animals (including fish and birds) and humans are subject to infection by nematodes which can result in debilitation long term disease. Infection by nematodes can result in significant economic loss in domestic animals and poultry. Infection may be in the gastrointestinal tract, the lymphatic system or in other tissue or organs. Nematode parasites include, among others, Ancylo stoma, Necator, *Ascaris, Strongyloides, Trichinella, Capillaria, Toxocara, Toxascaris, Trichuris, Enterobius, Onchocerca, Brugia, Wuchereria,* or *Dracunculus*. More specifically, nematode parasites include among others *Ancylostoma duodenale, Necator americanus, Trichuris trichiura, Ascaris lumbricoides, Strongyloides stercoralis, Trichinella spiralis, Toxocara canis, Toxocara cati, Enterobius vermicularis, Onchocerca volvulus, Brugia malayi, Brugia timori, Wuchereria bancrofti,* and *Drancunculus medinenis*.

Diseases associated with nematode infection include filariasis (lymphatic filariasis, subcutaneous filariasis and serous cavity filariasis), various GI tract infections (hookworm, roundworm, pinworm, whipworm, thread worm), Toxocariasis, Trichinosis, Onchocerciasis (River Blindness).

In a specific embodiment, compounds of this invention of any of the formulas herein can block incorporation of Galf into polysaccharides essential for viability or virulence of pathogenic microorganisms.

In specific embodiments, the invention provides compounds of any formulas herein which are cell permeable.

The term "alkyl" refers to a monoradical of a branched or unbranched (straight-chain or linear) saturated hydrocarbon. Alkyl groups include those having 1 to 22 carbon atoms ($C_1$-$C_{22}$ alkyl). Alkyl groups include those having 1-12 carbon atoms ($C_1$-$C_{12}$ alkyl). Alkyl groups include those having 1 to 6 carbon atoms ($C_1$-$C_6$ alkyl) including methyl, ethyl, propyl, butyl, pentyl and hexyl groups, including all isomers thereof. In specific embodiments, alkyl groups include those having 1-3 carbons ($C_1$-$C_3$ alkyl groups). Alkyl groups of substituent groups are preferably $C_1$-$C_3$ alkyl and more preferably methyl groups.

The term "cycloalkyl" refers to cyclic alkyl groups having 3 to 22, preferably 3-10 ring carbon atoms, more preferably 5-8 ring carbon atoms and yet more preferably 5 or 6 ring carbons. Cycloalkyl groups can have a single ring, may be bicyclic, tricyclic or the like. Cycloalkyl groups include, by way of example, single ring structures such as cyclopropyl, cyclobutyl, cyclopentyl, cyclohexyl, cyclooctyl, and the like, or multiple ring structures such as adamantanyl, and the like.

Unless otherwise indicated alkyl groups including cycloalkyl groups are optionally substituted as defined herein.

A specific substituted alkyl group is an aryl-substituted alkyl group where the terms aryl and alkyl are as defined herein. In specific embodiments, the substituted alkyl group is a $C_1$-$C_3$ alkyl group, and in particular is a methyl group. In specific examples the aryl group is an optionally substituted phenyl group. In specific examples, these groups include optionally substituted benzyl groups and optionally substituted phenethyl groups. Particular substituted aryl-substituted alkyl group is one that is substituted on the aryl ring with one or more halogens or one or more alkyl groups.

Another specific substituted alkyl group is a halo substituted alkyl group where alkyl is as defined above. This group includes alkyl groups having 1-3 carbon atoms and having 1 to 7 halogens. This group particularly includes alkyl groups with fluorine substitution, chlorine substitution and bromine substitution. A specific haloalkyl group is —$CF_3$.

The term "alkylene" refers to a diradical of a branched or unbranched saturated hydrocarbon chain, which unless otherwise indicated can have 1 to 10 carbon atoms, 1 to 6 carbon atoms, or 2-4 carbon atoms. This term is exemplified by groups such as methylene (—$CH_2$—), ethylene (—$CH_2CH_2$—), and more generally —$(CH_2)_s$—, where s is an integer ranging from 1-10 or more preferably 1-6 or s is 1, 2, 3 or 4. Alkylene groups may be branched, e.g., by substitution with alkyl group substituents. Alkylene groups may be optionally substituted as described herein.

The term "alkoxy" refers to the group —OR' where R' is an alkyl group as defined above. The term "cyclalkoxy" refers to the group —OR' where R' is a cycloalkyl group as defined above. Alkoxy and cycloalkoxy group may be optionally substituted as described herein. A particular substituted alkoxy group is a halo-substituted alkoxy group, such as —O—$CF_3$.

The term "alkenyl" refers to a monoradical of a branched or unbranched (straight-chain or linear) hydrocarbon having one or more C=C double bonds (C=C). Double bonds in an alkenyl group may be conjugated. Alkenyl groups include those having 2 to 22 carbon atoms ($C_2$-$C_{22}$ alkenyl). Alkenyl groups include those having 1-12 carbon atoms ($C_2$-$C_{12}$ alkenyl). Alkenyl groups include those having 2 to 6 carbon atoms ($C_2$-$C_6$ alkenyl) including vinyl (ethenyl), propenyl, allyl, butenyl, pentenyl, hexenyl, including all isomers thereof. In specific embodiments, alkenyl groups include those having 2, 3 or 4 carbons ($C_2$-$C_4$ alkenyl groups). Alkenyl groups which are substituent groups are preferably $C_2$-$C_4$ alkenyl. Alkenyl groups specifically include those with one double bond or those with two double bonds.

The term "cycloalkenyl" refers to cyclic alkenyl groups having 3 to 22, preferably 5-10 carbon atoms and more preferably 5 or 6 carbon atoms and one or more C=C double bonds. Cycloalkenyl groups can have a single ring, may be bicyclic, tricyclic or the like. Cycloalkenyl groups include, by way of example, single ring structures such as cyclopropenyl, cyclobutenyl, cyclopentenyl, cyclohexenyl, cyclooctenyl, and the like, or multiple ring structures such as adamantanenyl, and the like. Cycloalkenyl groups include those having one double bond or those having two double Unless otherwise indicated alkenyl groups including cycloalkenyl groups are optionally substituted as defined herein. In preferred embodiments, alkenyl or cycloalkenyl groups have one or two C=C double bonds which may be conjugated. In specific embodiments, alkenyl groups and cycloalkenyl groups have a single C=C double bond. A specific substituted alkenyl group is a halo-alkenyl group and a more specific halo-alkenyl group is a haloallyl group, e.g., —CH=CH—$CH_2Z$, where Z is a halogen, including fluorine, chlorine, bromine or iodine.

The term "carbocyclic" is used generically herein to refer to groups which contain a carbon ring which may be a saturated, partially unsaturated or aromatic ring. Carbocyclic groups may contain one or more than one carbon ring which ring may be a cycloakyl, unsaturated cycloalkyl or aryl ring. Typically carbocyclic rings include those having 3-12 carbon atoms in the ring. Carbocyclic rings include those having two or more fused rings, bicyclic rings, tricyclic ring etc. Carbocyclic groups include those having from 3 to 22 carbon atoms. Carbocyclic groups include those having from 3-10 carbon atoms. Preferred carbocyclic rings have 6 to 12 carbon atoms. Unless otherwise indicated carbocyclic groups are optionally substituted as defined herein.

The term "carbocyclyoxy" refers to the group —OR', where R' is a carbocyclic group as defined above.

The term "heterocyclyl" is also used generically herein to refer to carbocyclic rings in which one or more ring carbons are replaced with a heteroatom. Alternatively, the group is described as a monovalent group formed by removing a hydrogen atom from any ring atom of a heterocylic compound. The heterocyclyl group may contain one or more heteroatom containing ring. The heterocyclyl group may contain a single heteroatom containing ring. The heterocyclyl group may contain one heteroatom containing ring having a 3 to 10 member ring with 1-3 heteroatoms. The heterocyclyl group may contain two heteroatom containing rings, which may be fused rings, having 3 to 10 member rings with 1-6 heteroatoms. The heterocyclyl group may contain a carbon ring in combination with a heteroatom containing ring. Heterocyclyl groups can contain from 1-6 heteroatoms, 1-4 heteroatoms, 2 heteroatoms or 1 heteroatom. Preferred heteroatoms are N, O or S (or NR' where R' is a hydrogen, alkyl or an optional substituent). Heterocyclyl groups can contain one or more double bonds. Heterocyclyl groups can contain one double bond. Heterocyclyl groups can contain two double bonds. Heterocyclyl groups can have one or more aromatic rings. Heterocyclyl groups can be or contain heteroaryl groups. Unless otherwise indicated heterocyclyl groups are optionally substituted as defined herein. Heterocyclyl groups include those having 5-12 ring atoms, with 1, 2 or 3 heteroatoms and 1, 2 or 3 double bonds. Heterocyclyl groups include those having 5- and 6-member rings with one or two nitrogens and one or two double bonds. Heterocyclyl groups include those having 5- and 6-member rings with an oxygen or a sulfur and one or two double bonds. Heterocyclyl groups include those having 5- or 6-member rings and two different heteroatoms, e.g., N and O, O and S or N and S. Specific heterocyclyl groups include among others among others, pyrrolidinyl, piperidyl, piperazinyl, pyrrolinyl, morpholinyl, oxazolyl, oxazolinyl, oxazolidinyl, indolyl, triazoly, and triazinyl groups.

The term "heterocyclyoxy" refers to the group —OR', where R' is an heterocyclyl group as defined above.

The term "aryl" refers to a monoradical containing at least one aromatic ring. The radical is formally derived by removing a H from an aryl ring carbon. Aryl groups contain one or more rings at least one of which is aromatic. Rings of aryl groups may be linked by a single bond or a linker group or may be fused. Exemplary aryl groups include phenyl, biphenyl and naphthyl groups. Aryl groups include those having from 6 to 30 carbon atoms. Preferred aryl groups are those containing 6-12 carbon atoms. Unless otherwise noted aryl groups are optionally substituted as described herein.

The term aryoxy refers to the group —OR', where R' is an aryl group as defined

The term "heteroaryl" refers to a group that contains at least one aromatic ring in which one or more of the ring carbons is replaced with a heteroatom (non-carbon atom). Heteroaryl groups are a class of heterocyclyl groups derived from heteroaromatic compounds by removal of a hydrogen atom form any ring atom. To satisfy valence the heteroatom may be bonded to H or a substituent groups. Ring carbons may be replaced with —O—, —S—, —NR—, —N=, —PR—, or —POR— among others, where R is an alkyl, aryl, heterocyclyl or heteroaryl group. Heteroaryl groups may include one or more aryl groups (carbon aromatic rings). Heteroaromatic and aryl rings of the heteroaryl group may be linked by a single bond or a linker group or may be fused. Heteroaryl groups include those having aromatic rings with 5 or 6 ring atoms of which 1-3 ring atoms are heteroatoms. Preferred heteroatoms are —O—, —S—, —NR— and —N=. Heteroaryl groups include those containing 5-12 ring atoms as well as those having 5 and 6 ring atoms. Unless otherwise noted heteroaryl groups are optionally substituted as described herein. Heteroaryl groups include groups having one or more aromatic rings in which at least one ring contains a heteroatom (a non-carbon ring atom). Heteroaryl groups include those having one or two heteroaromatic rings carrying 1, 2 or 3 heteroatoms and optionally have one 6-member aromatic ring. Heteroaryl groups can contain 5-20, 5-12 or 5-10 ring atoms. Heteroaryl groups include those having one aromatic ring contains a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include furyl, thiophenyl, pyrrolyl, imidazolyl, pyrazolyl, pyridinyl, pyrazinyl, pyrimidinyl, quinolinyl, and purinyl groups.

The term heteroaryoxy refers to the group —OR', where R' is a heteroaryl group as defined herein.

Optional substitution is substitution by one or more non-hydrogen substituents selected from halogen, hydroxyl, mercapto (—SH, also sometimes called a thiol group), nitro, cyano, azide, isocyano, thiocyano, oxo (to form, for example, a >C=O moiety) optionally substituted $C_1$-$C_6$ alkyl, optionally substituted $C_1$-$C_6$-alkenyl, optionally substituted $C_1$-$C_6$ alkoxy, acyl (—COR', where R' is optionally substituted alkyl or optionally substituted aryl and in particular is unsubstituted $C_1$-$C_6$ alkyl, unsubstituted phenyl, unsubstituted benzyl or halogenated phenyl or halogenated benzyl), nitrophenyl, alkoxyphenyl, optionally substituted thioalkyl (—S-alkyl), optionally substituted aryl, optionally substituted heteroaryl, optionally substituted cycloalkyl, optionally substituted heterocyclyl,
—$SO_2$—$N(R_S)_2$, —$SO_2$—$R_S$, —$COOR_S$, —$COR_S$, —CON $(R_S)_2$, —$N(R_S)_2$, where $R_S$ is hydrogen, $C_1$-$C_6$ alkyl, $C_1$-$C_6$ alkenyl, $C_1$-$C_6$ haloalkyl, $C_1$-$C_6$ haloalkoxy, phosphate, phosphonate, carboxyl, and wherein substitution for substituent groups, if present, includes one or more halogen, hydroxyl, mercapto (—SH), nitro, cyano, azide, isocyano, thiocyano, isocyanate, isothiocyanate, unsubstituted $C_1$-$C_6$ alkyl, unsubstituted $C_1$-$C_6$-alkenyl, unsubstituted $C_1$-$C_6$ alkoxy, unsubstituted thioalkyl, unsubstituted aryl, unsubstituted heteroaryl, unsubstituted cycloalkyl, unsubstituted heterocyclyl,
—$SO_2$—$N(R_S)_2$, —$SO_2$—$R_S$, —$COOR_S$, —$COR_S$, —CON $(R_S)_2$, —$N(R_S)_2$, where $R_S$ is hydrogen, unsubstituted $C_1$-$C_6$ alkyl, unsubstituted $C_1$-$C_6$ alkenyl, $C_1$-$C_6$ haloalkyl, or $C_1$-$C_6$ haloalkoxy. Preferred alky, alkoxy, and haloalkyl groups have one to three carbon atoms. A preferred alkyl group is methyl. A preferred haloalkyl group is trifluoromethyl. Preferred alkenyl groups have 2-4 carbon atoms. Substituent alkyl groups include methyl, ethyl, n-propyl and iso-propyl groups. Substituent alkenyl groups include vinyl (—CH=$CH_2$) and allyl (—$CH_2$—CH=$CH_2$).

All alkyl, cycloalkyl, alkenyl, cycoalkenyl, aryl, heteroaryl, heterocyclyl, and carbocyclic groups herein are optionally substituted with one or more non-hydrogen substituents unless otherwise specified. Substitution may be on one or more carbons or, if feasible, on one or more heteroatoms, e.g., a nitrogen. The number of substituents on such groups depends generally upon the nature of the group, but includes substitution with one, two, three, four, five or six substituents.

It will be understood that unsubstituted and substituted carbocyclyl, unsubstituted and substituted heterocyclyl, unsubstituted and substituted aryl and unsubstituted and substituted heteroaryl monovalent groups can be bonded to another chemical moiety at different ring positions. For example, a monosubstituted phenyl group may be bonded via three different ring carbons to give a 2-substituted, 3-substituted or 4-substituted mono-substituted phenyl group. For example, an unsubstituted napthyl group may be a napth-1-yl or a napth-2-yl group dependent upon the carbon through which it is bonded. Standard naming conventions are employed in designating the ring site of bonding which is well-known in the art. When a specific ring position through which the cyclic group is to be attached is not given, all possible ring attachment sites of the group are to be included.

As to any of the groups herein which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The compounds of this invention may contain one or more chiral centers. Accordingly, this invention is intended to include racemic mixtures, diasteromers, enantiomers and mixture enriched in one or more stereoisomer. The scope of the invention as described and claimed encompasses the racemic forms of the compounds as well as the individual enantiomers and non-racemic mixtures thereof.

Treatment methods of this invention comprise the step of administering an effective amount of one or more compounds of this invention, or a salt thereof to an individual (human and/or non-human animal) to treat or prevent infection. The term "effective amount," as used herein, refers to the amount of the compound, that, when administered to the individual is effective to at least partially treat or prevent infection, or to at least partially ameliorate a symptom of infection. Infection herein refers to infection by a microorganism which contains the enzyme UGM. Infection herein refers to infection by a fungus, algae, bacterium or nematode. Infection herein refers to infection by a *mycobacterium*. As is understood in the art, the effective amount of a given compound will depend at least in part upon, the type of infectious organism, the mode of administration, any carrier or vehicle (e.g., solution, emulsion, etc.) employed, the extent of damage and the specific individual to whom the compound is to be administered (age, weight, condition, sex, etc.). The dosage requirements needed to achieve the "effective amount" vary with the particular compositions employed, the route of administration, the severity of the symptoms presented and the particular subject being treated. Based on the results obtained in standard pharmacological test procedures, projected daily dosages of active compound can be determined as is understood in the art.

Compounds of this invention can be employed in unit dosage form, e.g. as tablets or capsules. In such form, the active compound or more typically a pharmaceutical composition containing the active compound is sub-divided in unit dose containing appropriate quantities of the active compound; the unit dosage forms can be packaged compositions, for example, packaged powders, vials, ampoules, pre-filled syringes or sachets containing liquids. The unit dosage form can be, for example, a capsule or tablet itself, or it can be the appropriate number of any such compositions in package form.

Any suitable form of administration can be employed in the method herein. The compounds of this invention can, for example, be administered in oral dosage forms including tablets, capsules, pills, powders, granules, elixirs, tinctures, suspensions, syrups and emulsions. Oral dosage forms may include sustained release or timed release formulations. The compounds of this invention may also be administered topically, intravenously, intraperitoneally, subcutaneously, or intramuscularly, all using dosage forms well known to those of ordinary skill in the pharmaceutical arts.

Pharmaceutical and veterinary compositions of the invention may also be in the form of oil-in-water or water-in-oil emulsions, where the oily phase is any suitable oil, including vegetable or mineral oil. Emulsifying agents and/or surfactants may be included in such emulsions. In an embodiment, the compositions of the invention are formed as microemulsions. Methods and materials for formation of emulsions and microemulsions for pharmaceutical and veterinary compositions are well known in the art.

Pharmaceutical and veterinary compositions of the invention may be in the form of aqueous solution or aqueous suspensions where the active ingredient is dissolved or dispersed, typically in the form of a powder, in an aqueous pharmaceutically acceptable solvent. Alternatively, active ingredients can be dispersed in an oily phase.

In another embodiment, the pharmaceutical and veterinary compositions of the can be in the form of pastes, gels and creams, wherein the active ingredient is dissolved in a component of the paste, gel or cream or is dispersed therein.

The therapeutically active compounds of the invention can be administered alone, but generally will be administered with a pharmaceutical carrier selected upon the basis of the chosen route of administration and standard pharmaceutical practice.

Pharmaceutical compositions and medicaments of this invention comprise one or more compounds in combination with a pharmaceutically acceptable carrier, excipient, or diluent. Such compositions and medicaments are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety.

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Compositions for oral administration can be in either liquid or solid form.

The compounds of the present inventions may form salts which are also within the scope of this invention. Reference to a compound of the formulas herein is understood to include reference to salts thereof, unless otherwise indicated. The term "salt(s)", as employed herein, denotes acidic and/or basic salts formed with inorganic and/or organic acids and bases. In addition, when a compound of a formula herein contains both a basic moiety, such as, but not limited to an amine or a pyridine ring, and an acidic moiety, such as, but not limited to, a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

Well-known methods for assessment of drugability can be used to further assess active compounds of the invention for application to given therapeutic application. The term "drugability" relates to pharmaceutical properties of a prospective drug for administration, distribution, metabolism and excretion. Drugability is assessed in various ways in the art. For example, the "Lipinski Rule of 5" for determining drug-like characteristics in a molecule related to in vivo absorption and permeability can be applied (C. A. Lipinski, F. Lombardo, B. W. Dominy, P. J. Feeney, Experimental and computational approaches to estimate solubility and permeability in drug discovery and development settings, Adv. Drug Del. Rev., 2001, 46, 3-26 and Arup K. Ghose, Vellarkad N. Viswanadhan, and John J. Wendoloski, A Knowledge-Based Approach in Designing Combinatorial or Medicinal Chemistry Libraries for Drug Discovery, J. Combin. Chem., 1999, 1, 55-68.)

In general a preferred drug for oral administration exhibits no more than one violation of the following rules:

(1) Not more than 5 hydrogen bond donors (e.g., nitrogen or oxygen atoms with one or more hydrogens);

(2) Not more than 10 hydrogen bond acceptors (e.g., nitrogen or oxygen atoms);

(3) Molecular weight under 500 g/mol and more preferably between 160 and 480; or (4) log P less than 5 and more preferably between −0.4 to +5.6 and yet more preferably −1<log P<2. Methods for calculating or experimentally determining log P are well-known in the art. Compounds of this invention preferred for therapeutic application include those that do not violate one or more of 1-4 above.

Compounds of this invention preferred for therapeutic application include those having log P less than 5 and more preferably between −0.4 to +5.6 and yet more preferably −1<log P<2.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure.

Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomers and enantiomer (e.g., cis/trans isomers, R/S enantiomers) of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art.

Specific names of compounds are intended to be exemplary, as it is known that one of ordinary skill in the art can name the same compounds differently.

Molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated. The invention illustratively described herein suitably may be practiced in the absence of any element or elements, limitation or limitations which is not specifically disclosed herein.

It is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

THE EXAMPLES

Example 1: Synthetic Methods

A. General Procedures and Materials

All experiments were carried out in flame-dried glassware under nitrogen unless otherwise noted. Reagents were obtained via commercial sources without further purification, except for solvents. Dichloromethane (DCM) and diisopropylethylamine (DIEA) were distilled from calcium hydride. Tetrahydrofuran (THF) and toluene were distilled from sodium/benzophenone. Methanol (MeOH) was distilled from magnesium. Anhydrous dimethylformamide (DMF) was obtained from Sigma-Aldrich and used without further purification.

Analytical thin layer chromatography (TLC) was carried out on TLC silica gel 60 F254. Visualization of the TLC plates was performed with UV-visualization and p-anisaldehyde stain. Flash chromatography was performed on Silacycle Silaflash P60 silica gel.

Compound identity and purity were determined using NMR analysis. All bioactive compounds were determined to have ≥90% purity. NMR spectra were obtained on a Bruker Avance-400 (400 MHz), or Bruker Avance-500DCH (500 MHz) instrument. Chemical shifts are reported relative to residual solvent signals (CDCl$_3$): $^1$H: 7.27, $^{13}$C: 77.23; (CD$_3$OD):H: 3.31, $^{13}$C: 49.15.

B. Abbreviations

Galf, D-galactofuranose; *M. tuberculosis*, Mtb; UDP-Galp, UDP-galactopyranose; UGM, UDP-galactopyranose mutase; DLS, dynamic light scattering; MIC, minimum inhibitory concentration.

C. Synthetic Methods

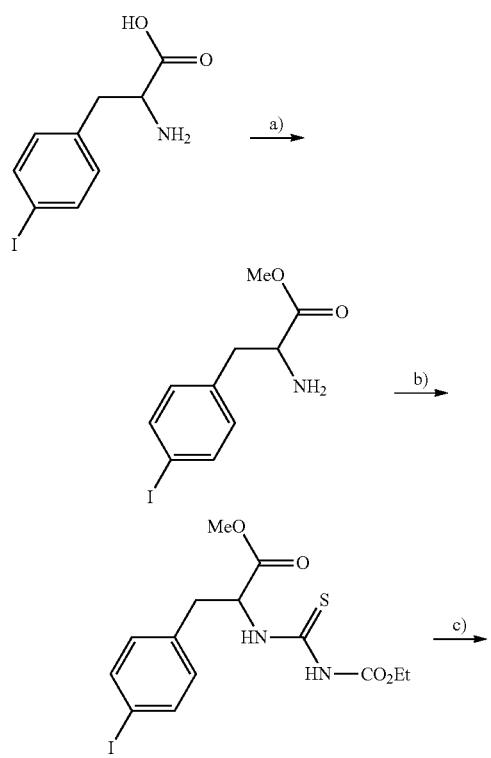

Scheme 1: Syntheseis of exemplary inhibitor compounds 1-9

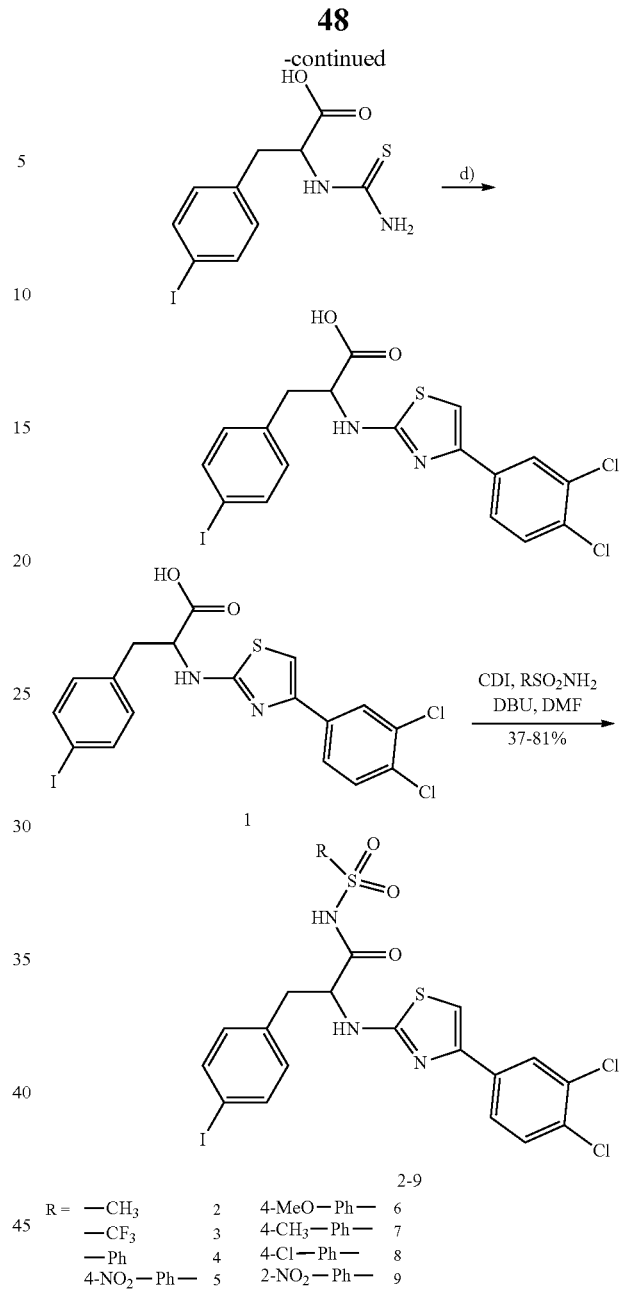

Scheme 1 illustrates exemplary synthesis of exemplary inhibitors of the invention of formula I. Reagents and conditions for Scheme 1 are as follows: (a) thionyl chloride, methanol; (b) ethyl carboxyisothiocyanate; (c) 1M sodium hydroxide, methanol; (d) 2-bromo-3',4'-dichloroacetophenone, dimethylformamide. The carboxylate 2-aminothiazole was synthesized according to previously published protocols. [Dykhuizen et al. (2008)] Synthetic procedures for carboxylate modification to either N-acylsulfonamide or ester derivatives are described below.

Methyl 2-amino-3-(4-iodophenyl)propanoate

A solution of 4-iodo-DL-phenylalanine (150 mg, 0.515 mmol) in methanol (3 mL) was cooled to 0° C. and thionyl chloride (300 µL, 4.12 mmol) was added dropwise. The mixture was heated at reflux for 4 hours, then cooled and concentrated in vacuo to yield the hydrochloride salt in quantitative yield (176 mg, 0.515 mmol). $^1$H NMR (500 MHz, Methanol-d4) δ 7.73 (d, J=7.8 Hz, 2H), 7.11 (d, J=7.9 Hz, 2H), 4.36 (dd, 1H), 3.82 (s, 3H), 3.25 (dd, J=15.7, 7.4 Hz, 2H), 3.20 (dd, J=15.7, 7.4 Hz, 1H). $^{13}$C NMR (126 MHz, MeOD) δ 168.83, 137.92, 133.87, 131.32, 92.81, 53.62, 52.45, 35.45. MS (ESI+m/z): (M-Cl) 305.9978 (M+H calc'd 305.9986).

Methyl 2-(3-(ethoxycarbonyl)thioureido)-3-(4-iodophenyl)propanoate

Methyl 2-amino-3-(4-iodophenyl)propanoate (176 mg, 0.515 mmol) was dissolved in dichloromethane (1.3 mL) and diisopropylethylamine (270 μL). The solution was cooled to 0° C. and ethoxycarbonyl isothiocyanate (67 μL, 0.566 mmol) was added dropwise. After warming to room temperature, the mixture was stirred for 45 minutes. Dichloromethane (7 mL) was added, and the organic layer was washed with water (7 mL), 10% aqueous HCl (7 mL), and saturated brine (7 mL) then dried over Na$_2$SO$_4$ and concentrated in vacuo to afford the product as a yellow oil (236 mg, 0.515 mmol) in quantitative yield. $^1$H NMR (500 MHz, Chloroform-d) δ 10.12 (s, 1H), 7.61 (d, J=8.2 Hz, 2H), 6.92 (d, J=8.2 Hz, 2H), 5.27 (dd, J=6.1 Hz, 1H), 4.22 (q, J=7.1 Hz, 2H), 3.73 (s, 3H), 3.29 (dd, J=14.0, 5.9 Hz, 1H), 3.17 (dd, J=14.0, 6.0 Hz, 1H), 1.30 (t, J=7.1 Hz, 3H). $^{13}$C NMR (126 MHz, CDCl$_3$) δ 179.23, 170.55, 152.56, 137.65, 135.19, 131.22, 92.89, 77.46, 77.21 (CDCl$_3$), 76.95, 62.92, 58.82, 52.60, 36.72, 14.18. MS (ESI+m/z): (M+H) 437.0025 (M+H calc'd 437.0027).

3-(4-Iodophenyl)-2-thioureidopropanoic Acid

Methyl 2-(3-(ethoxycarbonyl)thioureido)-3-(4-iodophenyl)propanoate (236 mg, 0.515 mmol) was dissolved in a 1:1 solution of 1 M NaOH and MeOH (3 mL). The solution was heated to reflux for 30 min, then cooled and acidified to a pH of 3 with 10% HCl. The solution was extracted with EtOAc (3×15 mL), and the combined organic layers were dried with Na$_2$SO$_4$. The solvent was removed in vacuo to yield the thiourea as a white solid in quantitative yield (191 mg, 0.515 mmol). $^1$H NMR (500 MHz, Methanol-d4) δ 7.51 (d, J=8.2 Hz, 2H), 6.90 (d, J=8.1 Hz, 2H), 5.09 (dd, J=5.3 Hz, 1H), 3.17 (dd, J=13.9, 5.5 Hz, 1H), 2.94 (dd, J=13.9, 6.5 Hz, 1H). $^{13}$C NMR (126 MHz, MeOD) δ 183.30, 173.18, 137.20, 136.41, 91.59, 57.97, 36.84. MS (ESI-m/z): (M−H) 348.9521 (M−H calc'd 348.9513).

2-((4-(3,4-Dichlorophenyl)thiazol-2-yl)amino)-3-(4-iodophenyl)propanoic acid (1)

3-(4-Iodophenyl)-2-thioureidopropanoic acid (500 mg, 1.43 mmol) and 2-bromo-3',4'-dichloroacetophenone (458 mg, 1.71 mmol) were combined and dissolved in DMF (2.9 mL). The reaction was stirred for 1.5 hrs and concentrated in vacuo. The reaction mixture was purified with flash chromatography over SiO$_2$ (33% EtOAc/hexanes→50% EtOAc/hexanes+1% AcOH) to afford 1 in 85% yield (632 mg, 1.22 mmol). $^1$H NMR (500 MHz, Methanol-d4) δ 7.95 (d, J=2.0 Hz, 1H), 7.70 (dd, J=8.4, 2.0 Hz, 1H), 7.61 (d, J=8.3 Hz, 2H), 7.47 (d, J=8.4 Hz, 1H), 7.07 (d, J=8.3 Hz, 2H), 6.97 (s, 1H), 4.73 (dd, J=8.0, 5.4 Hz, 1H), 3.28 (dd, J=13.8, 5.2 Hz, 1H), 3.06 (dd, J=13.9, 8.1 Hz, 1H). $^{13}$C NMR (126 MHz, Methanol-d4) δ 175.47, 169.58, 149.43, 138.68, 136.92, 133.51, 132.75, 131.85, 131.65, 128.98, 126.63, 104.51, 92.79, 59.90, 38.45. MS (ESI+m/z): (M+H) 518.9183 (M+H calc'd 518.9193).

General Procedure for N-Acylsulfonamide Coupling (Used to Generate Compounds 2-9):

A solution of carbonyldiimidazole (31.3 mg, 0.193 mmol) and 1 (50 mg, 0.0963 mmol) was prepared in DMF (200 μL) and stirred for 1 hr at room temperature. To this was added a solution of sulfonamide RSO$_2$NH$_2$ (0.963 mmol) in DMF (500 μL), followed by a solution of DBU (144 μL, 0.963 mmol) in DMF (500 μL). The reaction mixture was stirred at room temperature overnight, then diluted with EtOAc (2 mL) and quenched with 10% HCl (2 mL). The organic fraction was washed with 5% NaHCO$_3$ (2 mL), dried over Na$_2$SO$_4$ and concentrated in vacuo. Initial purification of the crude product was carried out with a Waters Sep-Pak Plus PSA cartridge (eluted with 1% triethylamine in acetonitrile) to yield the resultant N-acylsulfonamide as a triethylammonium salt. Excess triethylamine was removed by dissolving the product in dichloromethane and washing with a 10% HCl solution. As necessary, further purification was performed by flash chromatography over SiO$_2$ (20% EtOAc/hexanes→20% EtOAc/hexanes+1% AcOH).

2-((4-(3,4-dichlorophenyl)thiazol-2-yl)amino)-3-(4-iodophenyl)-N-(methylsulfonyl)propanamide (2)

Using the general procedure for sulfonamide coupling, where RSO$_2$NH$_2$ is methanesulfonamide, 2 was isolated in 58% yield. $^1$H NMR (500 MHz, Methanol-d4) δ 8.01 (d, J=2.0 Hz, 1H), 7.73 (dd, J=8.4, 2.1 Hz, 1H), 7.65 (d, J=8.3 Hz, 2H), 7.47 (d, J=8.4 Hz, 1H), 7.10 (d, J=8.3 Hz, 2H), 7.03 (s, 1H), 4.61 (dd, J=8.3, 6.2 Hz, 1H), 3.16 (dd, J=13.8, 6.2 Hz, 1H), 3.09 (s, 3H), 3.03 (dd, J=13.9, 8.3 Hz, 1H). $^{13}$C NMR (126 MHz, MeOD) δ 169.11, 149.32, 138.84, 137.90, 136.78, 133.61, 132.83, 131.95, 131.72, 129.01, 126.59, 105.16, 93.05, 61.19, 41.42, 38.33. MS (ESI+m/z): (M+H) 595.9110 (M+H calc'd 595.9128).

2-((4-(3,4-dichlorophenyl)thiazol-2-yl)amino)-3-(4-iodophenyl)-N-(((trifluoromethyl)sulfonyl)propanamide (3)

Using the general procedure for sulfonamide coupling, where RSO$_2$NH$_2$ is trifluoromethanesulfonamide, 3 was isolated in 73% yield. $^1$H NMR (500 MHz, Methanol-d4) δ 7.75 (d, J=1.9 Hz, 1H), 7.53 (d, J=8.3 Hz, 2H), 7.48 (dd, J=8.4, 2.0 Hz, 1H), 7.45 (d, J=8.4 Hz, 1H), 7.00 (d, J=8.3 Hz, 2H), 6.96 (s, 1H), 4.47 (dd, J=8.8, 4.9 Hz, 1H), 3.23 (dd, J=14.0, 4.9 Hz, 1H), 2.92 (dd, J=14.0, 8.8 Hz, 1H). $^{13}$C NMR (126 MHz, MeOD) δ 175.45, 170.46, 138.95, 138.80, 137.98, 134.01, 133.70, 132.83, 132.66, 132.07, 129.39, 127.08, 122.85, 120.29, 105.40, 93.22, 63.83, 38.74. 19F NMR (377 MHz, MeOD) δ −79.19. MS (ESI+m/z): (M+H) 649.8871 (M+H calc'd 649.8846).

2-((4-(3,4-dichlorophenyl)thiazol-2-yl)amino)-3-(4-iodophenyl)-N-(phenylsulfonyl)propanamide (4)

Using the general procedure for sulfonamide coupling, where RSO$_2$NH$_2$ is benzenesulfonamide, 4 was isolated in 81% yield. $^1$H NMR (500 MHz, Chloroform-d) δ 7.98 (d, J=7.7 Hz, 2H), 7.79 (d, J=1.7 Hz, 1H), 7.63-7.51 (m, 4H), 7.46 (t, J=9.1 Hz, 3H), 6.87 (d, J=7.7 Hz, 2H), 6.79 (s, 1H), 4.50 (t, J=8.1, 5.7 Hz, 1H), 3.21 (dd, J=14.5, 5.7 Hz, 1H), 3.09 (dd, J=14.4, 8.1 Hz, 1H). $^{13}$C NMR (126 MHz, CDCl$_3$) δ 169.14, 167.19, 148.82, 138.33, 135.10, 134.16, 133.94, 133.09, 132.17, 131.30, 130.87, 129.40, 129.26, 129.11, 128.45, 128.07, 126.66, 125.36, 104.75, 93.21, 60.33, 35.81. MS (ESI+m/z): (M+H) 657.9292 (M+H calc'd 657.9285).

2-((4-(3,4-dichlorophenyl)thiazol-2-yl)amino)-3-(4-iodophenyl)-N-((4-nitrophenyl)sulfonyl)propanamide (5).

Using the general procedure for sulfonamide coupling, where RSO$_2$NH$_2$ is 4-nitrobenzenesulfonamide, 5 was isolated in 76% yield. $^1$H NMR (500 MHz, Methanol-d4) δ 8.04 (s, 4H), 7.76 (d, J=2.0 Hz, 1H), 7.58 (d, J=8.3 Hz, 2H), 7.52 (dd, J=8.4, 2.0 Hz, 1H), 7.39 (d, J=8.4 Hz, 1H), 7.02 (d, J=8.3 Hz, 2H), 6.96 (s, 1H), 4.49 (dd, J=8.1, 7.0 Hz, 1H), 3.06 (dd, J=14.0, 7.1 Hz, 1H), 3.02 (dd, J=14.0, 8.3 Hz, 1H). $^{13}$C NMR (126 MHz, Methanol-d4) δ 175.34, 168.69, 151.69, 149.07, 146.38, 138.84, 137.63, 136.44, 133.57, 132.66, 132.06, 131.67, 130.37, 128.98, 126.26, 124.95, 105.27, 93.08, 61.40, 37.83. MS (ESI+m/z): (M+H) 702.9169 (M+H calc'd 702.9135).

2-((4-(3,4-dichlorophenyl)thiazol-2-yl)amino)-3-(4-iodophenyl)-N-((4-methoxyphenyl)sulfonyl)propanamide (6)

Using the general procedure for sulfonamide coupling, where RSO$_2$NH$_2$ is 4-methoxybenzenesulfonamide, 6 was isolated in 42% yield. $^1$H NMR (500 MHz, Methanol-d4) δ 7.87 (d, J=2.0 Hz, 1H), 7.79 (d, J=9.0 Hz, 2H), 7.60 (dd, J=8.4, 2.0 Hz, 1H), 7.54 (d, J=8.3 Hz, 2H), 7.44 (d, J=8.4 Hz, 1H), 6.97 (s, 1H), 6.96 (d, J=8.4 Hz, 2H), 6.81 (d, J=9.0 Hz, 2H), 4.50 (dd, J=8.0, 6.7 Hz, 1H), 3.76 (s, 3H), 3.05 (dd, J=13.8, 6.7 Hz, 1H), 2.96 (dd, J=13.8, 8.1 Hz, 1H). $^{13}$C NMR (126 MHz, Methanol-d4) δ 173.39, 168.76, 165.18, 149.30, 138.77, 137.70, 136.68, 133.49, 132.65, 132.29, 131.83, 131.60, 131.34, 129.07, 126.57, 114.99, 105.05, 92.97, 61.17, 56.31, 38.05. MS (ESI+m/z): (M+H) 687.9413 (M+H calc'd 687.9390).

2-((4-(3,4-dichlorophenyl)thiazol-2-yl)amino)-3-(4-iodophenyl)-N-tosylpropanamide (7)

Using the general procedure for sulfonamide coupling, where RSO$_2$NH$_2$ is 4-toluenesulfonamide, 7 was isolated in 50% yield. $^1$H NMR (500 MHz, Methanol-d4) δ 7.86 (d, J=2.0 Hz, 1H), 7.73 (d, J=8.3 Hz, 2H), 7.60 (dd, J=8.4, 2.1 Hz, 1H), 7.53 (d, J=8.3 Hz, 2H), 7.44 (d, J=8.4 Hz, 1H), 7.13 (d, J=8.0 Hz, 2H), 6.96 (s, 1H), 6.95 (d, J=8.4 Hz, 2H), 4.51 (dd, J=8.0, 6.8 Hz, 1H), 3.04 (dd, J=13.8, 6.7 Hz, 1H), 2.96 (dd, J=13.8, 8.1 Hz, 1H), 2.28 (s, 3H). $^{13}$C NMR (126 MHz, Methanol-d4) δ 173.39, 168.76, 149.29, 145.95, 138.76, 138.00, 137.63, 136.70, 133.49, 132.63, 131.81, 131.58, 130.46, 129.12, 129.06, 126.59, 105.06, 92.99, 61.14, 38.05, 21.69. MS (ESI+m/z): (M+H) 671.9437 (M+H calc'd 671.9441).

N-((4-chlorophenyl)sulfonyl)-2-((4-(3,4-dichlorophenyl)thiazol-2-yl)amino)-3-(4-iodophenyl)propanamide (8)

Using the general procedure for sulfonamide coupling, where RSO$_2$NH$_2$ is 4-chlorobenzenesulfonamide, 8 was isolated in 49% yield. $^1$H NMR (500 MHz, Methanol-d4) δ 7.84 (d, J=2.0 Hz, 1H), 7.81 (d, J=8.7 Hz, 2H), 7.58 (dd, J=8.4, 2.0 Hz, 1H), 7.54 (d, J=8.3 Hz, 2H), 7.43 (d, J=8.4 Hz, 1H), 7.28 (d, J=8.7 Hz, 2H), 6.96 (d, J=8.3 Hz, 2H), 6.95 (s, 1H), 4.50 (dd, J=8.1, 6.8 Hz, 1H), 3.04 (dd, J=13.8, 6.9 Hz, 1H), 2.98 (dd, J=13.8, 8.0 Hz, 1H). $^{13}$C NMR (126 MHz, Methanol-d4) δ 173.52, 168.69, 149.23, 141.06, 139.47, 138.77, 137.53, 136.55, 133.53, 132.62, 131.96, 131.66, 130.69, 130.12, 129.02, 126.48, 105.14, 93.06, 61.16, 37.96. MS (ESI+m/z): (M+H) 691.8908 (M+H calc'd 691.8895).

2-((4-(3,4-dichlorophenyl)thiazol-2-yl)amino)-3-(4-iodophenyl)-N-((2-nitrophenyl)sulfonyl)propanamide (9)

Using the general procedure for sulfonamide coupling, where RSO$_2$NH$_2$ is 2-nitrobenzenesulfonamide, 9 was isolated in 37% yield. $^1$H NMR (500 MHz, Methanol-d4) δ 8.27-8.21 (m, 1H), 7.82 (d, J=2.0 Hz, 1H), 7.72-7.64 (m, 3H), 7.61 (dd, J=8.4, 2.0 Hz, 1H), 7.52 (d, J=8.3 Hz, 2H), 7.42 (d, J=8.4 Hz, 1H), 6.98 (d, J=8.3 Hz, 2H), 6.96 (s, 1H), 4.62 (dd, J=8.6, 6.0 Hz, 1H), 3.15 (dd, J=13.9, 5.9 Hz, 1H), 3.00 (dd, J=13.9, 8.6 Hz, 1H). $^{13}$C NMR (126 MHz, MeOD) δ 175.34, 168.86, 149.52, 149.21, 138.73, 137.75, 136.63, 136.02, 134.19, 133.54, 133.18, 132.66, 131.87, 131.61, 128.98, 126.59, 125.81, 105.20, 92.98, 61.28, 37.72. MS (ESI+m/z): (M+H) 702.9134 (M+H calc'd 702.9135).

Scheme 2: Synthesis of carboxylic ester compound 10

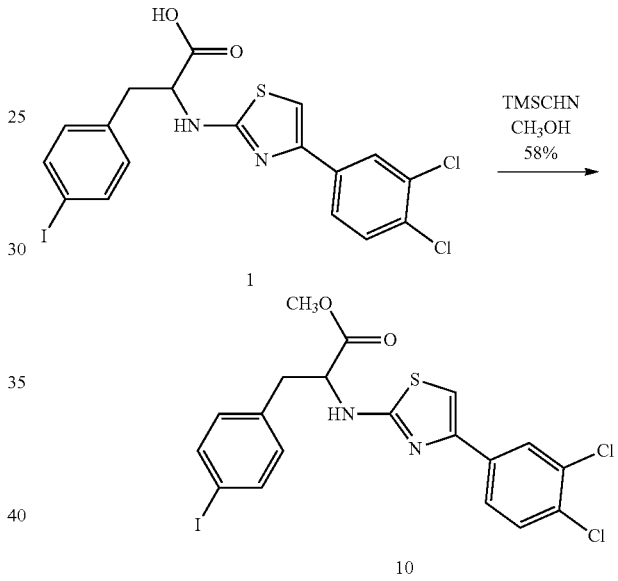

where TMSCHN is trimethylsilyldiazomethane

Scheme 2 illustrates exemplary synthesis of carboxylic esters of 2-aminothiazole derivatives of this invention.

Methyl 2-((4-(3,4-dichlorophenyl)thiazol-2-yl)amino)-3-(4-iodophenyl)propanoate (10)

A solution of 1 (19 mg, 0.024 mmol) in MeOH (200 μL) was cooled to 0° C., then trimethylsilyl diazomethane (72 μL, 0.144 mmol) was added dropwise. The mixture was allowed to warm to room temperature, then stirred overnight. The reaction mixture was concentrated in vacuo and purified with flash chromatography over SiO$_2$ (5% EtOAc/hexanes→10% EtOAc/hexanes) to afford 10 in 58% yield (7.7 mg, 0.014 mmol). $^1$H NMR (500 MHz, Chloroform-d) δ 7.90 (d, J=1.9 Hz, 1H), 7.62 (d, J=8.1 Hz, 2H), 7.59 (dd, J=8.4, 2.0 Hz, 1H), 7.43 (d, J=8.4 Hz, 1H), 6.90 (d, J=8.2 Hz, 2H), 6.74 (s, 1H), 4.85 (dd, J=11.7, 4.1 Hz, 1H), 3.77 (s, 3H), 3.32 (dd, J=13.9, 5.7 Hz, 1H), 3.14 (dd, J=14.0, 5.4 Hz, 1H). $^{13}$C NMR (126 MHz, CDCl$_3$) δ 172.19, 166.86, 149.16, 137.88, 135.77, 134.89, 132.87, 131.60, 131.55, 130.64, 128.18, 125.28, 103.38, 92.93, 58.34, 52.76, 37.58. MS (ESI+m/z): (M+H) 532.9324 (M calc'd 532.9349).

Preparation of Triazolothiadiazine Carboxylic Acids

A convergent synthetic route for preparation of triazolothiadiazines was designed to allow for facile and systematic variation of $R_1$ and $R_2$ groups (or $R_{11}$ and $R_{12}$ groups) based on Kamel et al 2014; Kaplancikh et al. 2008 and Bolognese et al. The presence of the carboxylic acid in the present scaffold prompted some variation in choices of reaction conditions to improve functional group compatibility. The $R_1$ and $R_2$ portions were built separately and then combined in the ultimate step which formed the heterobicyclic core. The $R_1$ portion was prepared from a carboxylic acid (commerically available or readily made), which could be elaborated in a single step to a thioaminotriazole derivative (compounds 4.2.01-07) through treatment with thiocarbohydrazide. The majority of literature examples show assembly of such thioaminotriazoles beginning from an acid hydrazide and using sequential treatment with carbon disulfide and hydrazine. In our hands, the single-step condensation and cyclization route was typically more efficient and produced a more reliably clean product which did not require purification by chromatography. However, for a handful of substrates, the two-step sequence was more successful (usually due to differences in substrate solubility). The $R_2$ portion was generated from a substituted aryl ketoacid (4.3.01-10); a number of these ketoacids were commercially available, and others were readily synthesized by via Friedel-Crafts acylation of the corresponding benzene derivative with succinic anhydride in the presence of aluminum trichloride. The aryl ketoacid was subsequently subjected to a-bromination, which in most cases preferentially occurred proximally to the ketone as opposed to the carboxylic acid. The resulting bromoketoacids (4.4.01-10) were purified by recrystallization in methylene chloride. The thioaminotriazole and bromoketoacid derivatives were combined to generate the final triazolothiadiazine product (11, 14, 15-32, Table 10).

starting material had been consumed as judged by TLC (24-48 hours). The reaction mixture was diluted in dichloromethane and washed with 10% hydrochloric acid in water to remove excess thiocarbohydrazide. The organic layer was dried over sodium sulfate, then concentrated in vacuo to yield the desired triazole as a pale yellow solid.

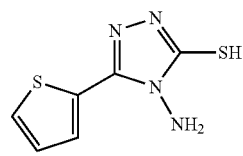

4.2.01

4-amino-5-(thiophen-2-yl)-4H-1,2,4-triazole-3-thiol (4.2.01)

Using the general procedure for thioaminotriazole synthesis, 4.2.01 was isolated in 80% yield. $^1$H NMR (500 MHz, Methanol-$d_4$) δ 8.06 (dd, J=3.8, 1.2 Hz, 1H), 7.63 (dd, J=5.1, 1.2 Hz, 1H), 7.18 (dd, J=5.1, 3.8 Hz, 1H). $^{13}$C NMR (126 MHz, MeOD) δ 167.28, 146.66, 129.04, 128.83, 127.01, 126.31. MS (ESI$^+$ m/z): (M+H) 199.0102 (M+H calc'd 199.0107).

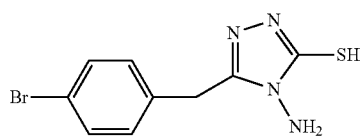

4.2.02

Scheme 3 Synthetic route to access carboxlate-bearing triazolothiadiazine analogs 11, 14, and 15-32

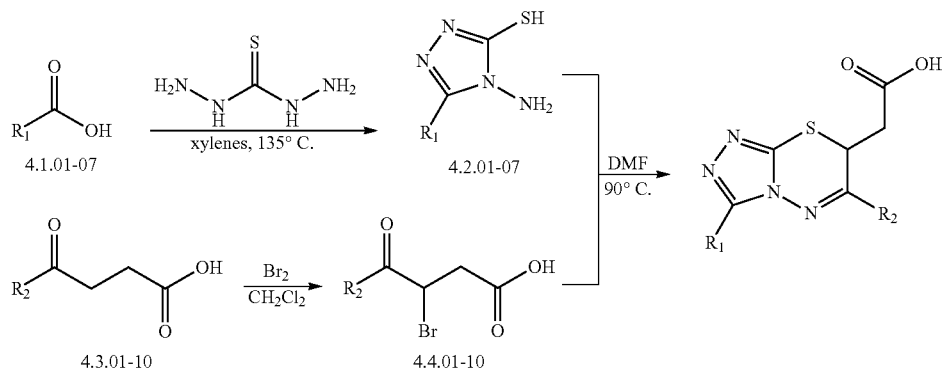

Scheme 3: Illustrates Synthesis of Triazolothiadiazine Carboxylic Acids

Scheme 3 illustrates synthesis of triazolothiadiazine carboxylic acids from $R_1$-derivatized thioaminotriazoles and $R_2$-derivatized bromoketoacids. Derivatized bromoketoacids were prepared by bromination of corresponding ketoacids. Starting ketoacids were synthesized by known methods or purchased from a commercial source. General procedure for preparation of $R_1$-derivatized thioaminotriazoles The carboxylic acid derivative (1.0 equiv) was dissolved in xylenes (2.0 M) and thiocarbohydrazide (2.0 equiv) was added. The reaction was heated at 135° C. until all acid 4-amino-5-(4-bromobenzyl)-4H-1,2,4-triazole-3-thiol (4.2.02)

Using the general procedure for thioaminotriazole synthesis, 4.2.02 was isolated in 87% yield. $^1$H NMR (500 MHz, Methanol-$d_4$) δ 7.46 (d, J=8.4 Hz, 2H), 7.23 (d, J=8.4 Hz, 2H), 4.06 (s, 2H). $^{13}$C NMR (126 MHz, MeOD) δ 168.61, 153.38, 136.08, 132.94, 132.15, 122.10, 31.33. MS (ESI$^+$ m/z): (M+H) 284.9807 (M+H calc'd 284.9805).

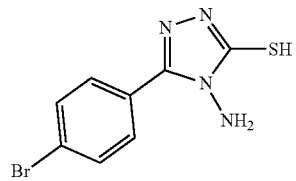

4.2.03

4-amino-5-(4-bromophenyl)-4H-1,2,4-triazole-3-thiol (4.2.03)

Using the general procedure for thioaminotriazole synthesis, 4.2.03 was isolated in 79% yield. $^1$H NMR (500 MHz, Methanol-$d_4$) δ 8.05 (d, J=8.6 Hz, 2H), 7.67 (d, J=8.6 Hz, 2H). $^{13}$C NMR (126 MHz, MeOD) δ 167.77, 149.17, 131.39, 129.53, 124.93, 124.55. MS (ESI$^+$ m/z): (M+H) 270.9651 (M+H calc'd 270.9648).

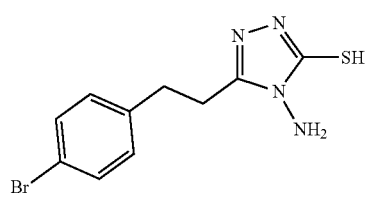

4.2.04

4-amino-5-(4-bromophenethyl)-4H-1,2,4-triazole-3-thiol (4.2.04)

Using the general procedure for thioaminotriazole synthesis, 4.2.04 was isolated in 40% yield. $^1$H NMR (500 MHz, DMSO-$d_6$) δ 13.43 (s, 1H, SH), 7.48 (d, J=8.4 Hz, 2H), 7.21 (d, J=8.3 Hz, 2H), 5.58 (s, 2H, NH$_2$), 2.99-2.89 (m, 4H). $^{13}$C NMR (126 MHz, DMSO) δ 166.31, 151.69, 140.26, 131.63, 131.14, 119.69, 30.89, 26.29. MS (ESI$^+$ m/z): (M+H) 298.9961 (M+H calc'd 298.9957).

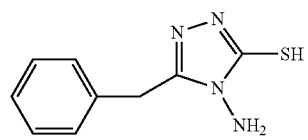

4.2.05

4-amino-5-(4-bromobenzyl)-4H-1,2,4-triazole-3-thiol (4.2.05)

Using the general procedure for thioaminotriazole synthesis, 4.2.05 was isolated in 36% yield.

$^1$H NMR (500 MHz, Methanol-$d_4$) δ 7.32-7.29 (m, 4H), 7.26-7.22 (m, 1H), 4.09 (s, 2H). $^{13}$C NMR (126 MHz, MeOD) δ 168.44, 153.85, 136.78, 130.12, 129.87, 128.28, 31.88. MS (ESI$^+$ m/z): (M+H) 207.0699 (M+H calc'd 207.0699).

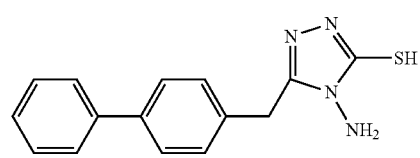

4.2.06

5-([1,1'-biphenyl]-4-ylmethyl)-4-amino-4H-1,2,4-triazole-3-thiol (4.2.06)

Using the general procedure for thioaminotriazole synthesis, 4.2.06 was isolated in 47% yield. $^1$H NMR (500 MHz, DMSO-$d_6$) δ 13.56 (s, 1H, SH), 7.64 (d, J=7.3 Hz, 2H), 7.61 (d, J=8.2 Hz, 2H), 7.46 (t, J=7.7 Hz, 2H), 7.39-7.33 (m, 3H), 5.58 (s, 2H, NH$_2$), 4.07 (s, 2H). $^{13}$C NMR (126 MHz, DMSO) δ 166.50, 151.78, 140.32, 139.20, 135.17, 129.91, 129.39, 127.84, 127.26, 127.05, 30.29. MS (ESI$^+$ m/z): (M+H) 283.1010 (M+H calc'd 283.1012).

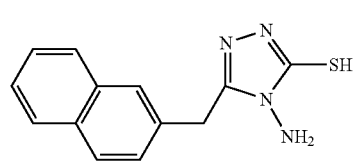

4.2.07

4-amino-5-(naphthalen-2-ylmethyl)-4H-1,2,4-triazole-3-thiol (4.2.07)

Using the general procedure for thioaminotriazole synthesis, 4.2.07 was isolated in 24% yield. $^1$H NMR (500 MHz, DMSO-$d_6$) δ 13.56 (s, 1H, SH), 7.91-7.84 (m, 3H), 7.78 (s, 1H), 7.53-7.46 (m, 2H), 7.44 (dd, J=8.5, 1.6 Hz, 1H), 5.59 (s, 2H, NH$_2$), 4.20 (s, 2H). $^{13}$C NMR (126 MHz, DMSO) δ 166.55, 151.80, 133.59, 133.45, 132.39, 128.43, 127.98, 127.95, 127.73, 127.63, 126.66, 126.24, 30.84. MS (ESI$^+$ m/z): (M+H) 257.0853 (M+H calc'd 257.0855).

General Procedure for Preparation of Ketoacids (Compounds 4.3.01-10)

Succinic anhydride (1.0 equiv) and aluminum trichloride (3.0 equiv) were suspended in an excess of the benzene derivative, then sonicated at 65° C. for approximately 6 hours or until the reaction was judged complete by TLC analysis. The reaction mixture was quenched by addition to cold 10% hydrochloric acid in water. The product was isolated by extraction with dichloromethane; combined organic layers were dried over sodium sulfate then concentrated in vacuo to obtain the desired ketoacid derivative which could be further purified if necessary by recrystallization in dichloromethane.

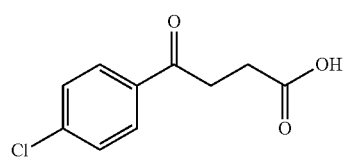

4.3.01

4-(4-chlorophenyl)-4-oxobutanoic acid (4.3.01)

Compound 4.3.01 was purchased from Sigma-Aldrich and used without further purification.

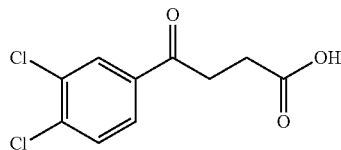

4.3.02

4-(3,4-dichlorophenyl)-4-oxobutanoic acid (4.3.02)

Using the general procedure for aryl ketoacid synthesis, 4.3.02 was isolated in 52% yield. $^1$H NMR (400 MHz, Chloroform-d) δ 8.04 (d, J=2.0 Hz, 1H), 7.79 (dd, J=8.4, 2.0 Hz, 1H), 7.54 (d, J=8.4 Hz, 1H), 3.24 (t, J=6.4 Hz, 2H), 2.81 (t, J=6.4 Hz, 2H). $^{13}$C NMR (126 MHz, CDCl$_3$) δ 195.62, 176.13, 137.99, 135.90, 133.42, 130.83, 130.10, 127.05, 33.21, 27.46. MS (ESI⁻ m/z): (M–H) 244.9774 (M–H calc'd 244.9777).

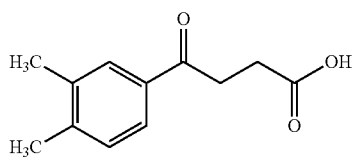

4.3.03

4-(3,4-dimethylphenyl)-4-oxobutanoic acid (4.3.03)

Using the general procedure for aryl ketoacid synthesis, 4.3.03 was isolated in 82% yield. $^1$H NMR (500 MHz, Chloroform-d) δ 7.75 (d, J=1.4 Hz, 1H), 7.71 (dd, J=7.8, 1.8 Hz, 1H), 7.21 (d, J=7.9 Hz, 1H), 3.29 (t, J=6.6 Hz, 2H), 2.80 (t, J=6.6 Hz, 2H), 2.32 (s, 6H). $^{13}$C NMR (126 MHz, CDCl$_3$) δ 197.70, 178.78, 142.88, 136.97, 134.30, 129.85, 129.18, 125.77, 33.05, 28.12, 20.05, 19.78. MS (ESI⁻ m/z): (M–H) 205.0871 (M–H calc'd 205.0870).

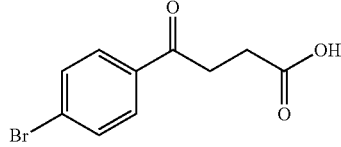

4.3.04

4-(4-bromophenyl)-4-oxobutanoic acid (4.3.04)

Compound 4.3.01 was purchased from Alfa Aesar and used without further purification.

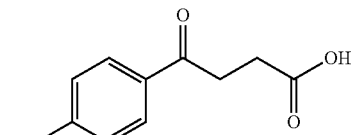

4.3.05

4-oxo-4-(4-(trifluoromethyl)phenyl)butanoic acid (4.3.05)

Compound 4.3.05 was purchased from Rieke Metals and used without further purification.

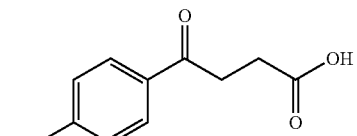

4.3.06

4-oxo-4-(p-tolyl)butanoic acid (4.3.06)

Using the general procedure for aryl ketoacid synthesis, 4.3.06 was isolated in 34% yield. $^1$H NMR (500 MHz, Methanol-d$_4$) δ 7.90 (d, J=8.2 Hz, 2H), 7.31 (d, J=8.0 Hz, 2H), 3.31-3.27 (m, 2H), 2.72-2.67 (m, 2H), 2.41 (s, 3H). $^{13}$C NMR (126 MHz, MeOD) δ 198.72, 175.24, 144.00, 134.19, 128.91, 127.81, 47.94, 32.88, 27.51, 20.20. MS (ESI⁻ m/z): (M–H) 191.0717 (M–H calc'd 191.0713).

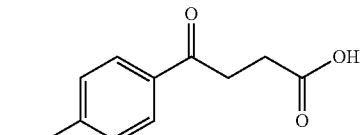

4.3.07

4-(4-methoxyphenyl)-4-oxobutanoic acid (4.3.07)

Compound 4.3.07 was purchased from Sigma-Aldrich and used without further purification.

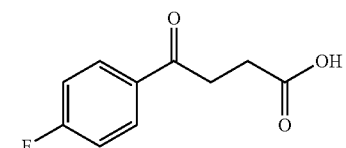

4.3.08

4-(4-fluorophenyl)-4-oxobutanoic acid (4.3.08)

Using the general procedure for aryl ketoacid synthesis, 4.3.08 was isolated in 42% yield. $^1$H NMR (400 MHz, Chloroform-d) δ 8.01 (dd, J=8.9, 5.4 Hz, 2H), 7.14 (t, J=8.6 Hz, 2H), 3.28 (t, J=6.5 Hz, 2H), 2.81 (t, J=6.5 Hz, 2H). $^{13}$C NMR (101 MHz, Chloroform-d) δ 196.23, 178.77, 165.89 (d, J=255.1 Hz), 132.82 (d, J=3.1 Hz), 130.70 (d, J=9.4 Hz), 115.78 (d, J=21.9 Hz), 33.05, 28.00. ¹⁹F NMR (377 MHz, CDCl₃) δ −104.77. MS (ESI⁺ m/z): (M+H) 197.0608 (M+H calc'd 197.0609).

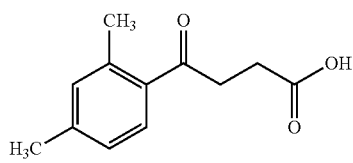

4-(2,4-dimethylphenyl)-4-oxobutanoic acid (4.3.09)

Compound 4.3.09 was purchased from Sigma-Aldrich and used without further purification.

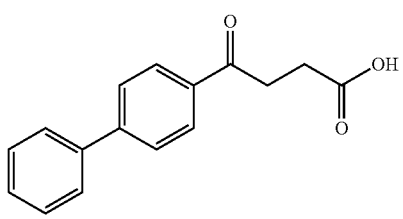

4-([1,1'-biphenyl]-4-yl)-4-oxobutanoic acid (4.3.10)

Compound 4.3.10 was purchased from Sigma-Aldrich and used without further purification.

General procedure for preparation of bromoketoacids (compounds 4.4.01-10): The aryl ketoacid (either synthesized in-house or purchased from a commercial source) was dissolved in dichloromethane (0.2 M) and cooled to 0° C. The Br₂ (1.1 equiv) was added dropwise, then the reaction was warmed to room temperature and stirred until reaction was complete as judged by TLC analysis. For some more slowly-reacting derivatives, the reaction mixture was heated to reflux at 40° C. The reaction mixture was concentrated in vacuo to yield the brominated ketoacid which could be further purified if necessary by recrystallization in dichloromethane.

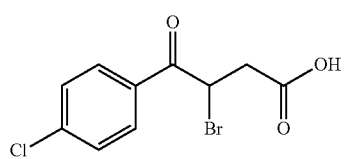

3-bromo-4-(4-chlorophenyl)-4-oxobutanoic acid (4.4.01)

Using the general procedure for bromoketoacid preparation, 4.4.01 was isolated in 84% yield. ¹H NMR (400 MHz, Chloroform-d) δ 7.95 (d, J=8.6 Hz, 2H), 7.46 (d, J=8.6 Hz, 2H), 5.35 (dd, J=8.9, 5.5 Hz, 1H), 3.51 (dd, J=17.7, 9.0 Hz, 1H), 3.12 (dd, J=17.7, 5.5 Hz, 1H). ¹³C NMR (101 MHz, MeOD) δ 193.39, 173.66, 141.28, 134.11, 131.80, 130.25, 40.88, 39.56. MS (ESI⁻ m/z): (M−H) 288.9278 (M−H calc'd 288.9272).

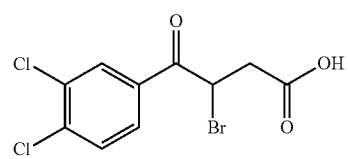

3-bromo-4-(3,4-dichlorophenyl)-4-oxobutanoic acid (4.4.02)

Using the general procedure for bromoketoacid preparation, 4.4.02 was isolated in quantitative yield. ¹H NMR (500 MHz, Chloroform-d) δ 8.10 (d, J=2.0 Hz, 1H), 7.84 (dd, J=8.4, 2.1 Hz, 1H), 7.59 (d, J=8.4 Hz, 1H), 5.32 (dd, J=9.1, 5.4 Hz, 1H), 3.54 (dd, J=17.7, 9.1 Hz, 1H), 3.14 (dd, J=17.7, 5.4 Hz, 1H). ¹³C NMR (126 MHz, CDCl₃) δ 189.90, 175.62, 138.74, 133.66, 133.20, 130.95, 130.94, 127.95, 38.17, 38.03. MS (ESI⁻ m/z): (M−H) 322.8883 (M−H calc'd 322.8882).

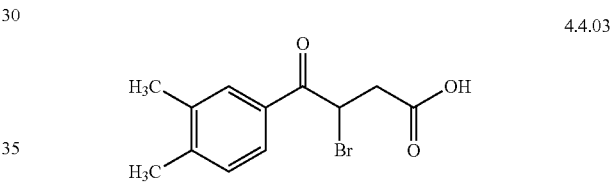

3-bromo-4-(3,4-dimethylphenyl)-4-oxobutanoic acid (4.4.03)

Using the general procedure for bromoketoacid preparation, 4.4.03 was isolated in 97% yield. ¹H NMR (400 MHz, Chloroform-d) δ 7.79 (d, J=1.5 Hz, 1H), 7.76 (dd, J=7.6, 1.5 Hz, 1H), 7.24 (d, J=8.0 Hz, 1H), 5.43 (dd, J=8.7, 5.8 Hz, 1H), 3.51 (dd, J=17.6, 8.7 Hz, 1H), 3.12 (dd, J=17.6, 5.8 Hz, 1H), 2.32 (s, 6H). ¹³C NMR (101 MHz, CDCl₃) δ 191.83, 176.43, 143.95, 137.33, 131.40, 130.14, 130.05, 126.78, 38.66, 38.34, 20.18, 19.84. MS (ESI⁺ m/z): (M+H) 285.0121 (M+H calc'd 285.0126).

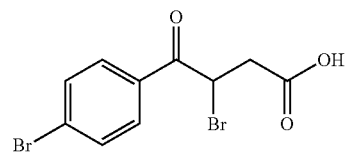

3-bromo-4-(4-bromophenyl)-4-oxobutanoic acid (4.4.04)

Using the general procedure for bromoketoacid preparation, 4.4.04 was isolated in 91% yield. ¹H NMR (400 MHz, Chloroform-d) δ 7.88 (d, J=8.5 Hz, 2H), 7.64 (d, J=8.5 Hz, 2H), 5.36 (dd, J=8.9, 5.5 Hz, 1H), 3.53 (dd, J=17.7, 8.9 Hz, 1H), 3.13 (dd, J=17.7, 5.4 Hz, 1H). $^{13}$C NMR (101 MHz, CDCl$_3$) δ 191.06, 176.17, 132.35, 132.21, 130.52, 129.40, 38.36, 38.20. MS (ESI$^+$ m/z): (M+H) 334.8913 (M+H calc'd 334.8916).

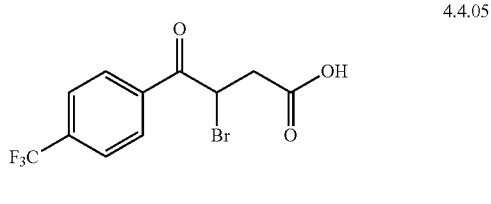

3-bromo-4-oxo-4-(4-(trifluoromethyl)phenyl)butanoic acid (4.4.05)

Using the general procedure for bromoketoacid preparation, 4.4.05 was isolated in quantitative yield. $^1$H NMR (400 MHz, Chloroform-d) δ 8.13 (d, J=8.2 Hz, 2H), 7.76 (d, J=8.3 Hz, 2H), 5.41 (dd, J=9.1, 5.4 Hz, 1H), 3.56 (dd, J=17.7, 9.1 Hz, 1H), 3.16 (dd, J=17.7, 5.4 Hz, 1H). $^{13}$C NMR (101 MHz, Chloroform-d) δ 191.29, 176.54, 136.61, 135.36 (q, J=32.9 Hz), 129.57, 126.08 (q, J=3.7 Hz), 124.95, 122.24, 38.61, 38.33. MS (ESI$^+$ m/z): (M+H) 324.9682 (M+H calc'd 324.9682).

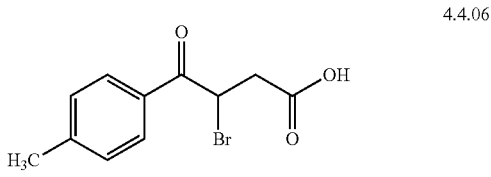

3-bromo-4-oxo-4-(p-tolyl)butanoic acid (4.4.06)

Using the general procedure for bromoketoacid preparation, 4.4.06 was isolated in 80% yield. $^1$H NMR (400 MHz, Chloroform-d) δ 8.20 (d, J=7.9 Hz, 2H), 7.93 (d, J=7.7 Hz, 2H), 7.29 (d, J=8.0 Hz, 2H), 7.26 (d, J=8.1 Hz, 2H), 5.50-5.35 (m, 1H), 3.96 (s, 2H), 3.53 (dd, J=17.4, 8.3 Hz, 1H), 3.14 (dd, J=17.4, 4.8 Hz, 1H), 2.43 (s, 3H). $^{13}$C NMR (101 MHz, CDCl$_3$) δ 191.66, 176.16, 131.18, 129.59, 129.25, 128.79, 50.91, 38.37, 21.87. MS (ESI$^-$ m/z): (M−H) 268.9823 (M−H calc'd 268.9818).

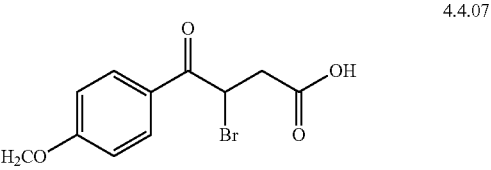

3-bromo-4-(4-methoxyphenyl)-4-oxobutanoic acid (4.4.07)

Using the general procedure for bromoketoacid preparation, 4.4.07 was isolated in quantitative yield. $^1$H NMR (400 MHz, Chloroform-d) δ 8.00 (d, J=8.8 Hz, 2H), 6.94 (d, J=8.8 Hz, 2H), 5.43 (dd, J=8.5, 5.9 Hz, 1H), 3.85 (s, 3H), 3.49 (dd, J=17.5, 8.6 Hz, 1H), 3.11 (dd, J=17.6, 5.9 Hz, 1H). $^{13}$C NMR (101 MHz, CDCl$_3$) δ 190.75, 175.89, 164.25, 131.53, 126.41, 114.12, 55.64, 38.83, 38.42. MS (ESI$^+$ m/z): (M+H) 286.9911 (M+H calc'd 286.9914).

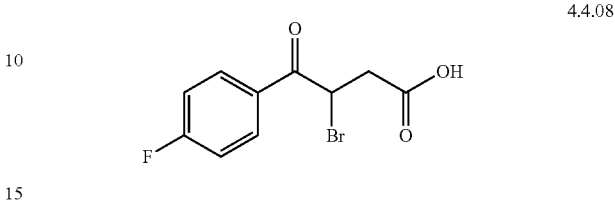

3-bromo-4-(4-fluorophenyl)-4-oxobutanoic acid (4.4.08)

Using the general procedure for bromoketoacid preparation, 4.4.08 was isolated in 96% yield. $^1$H NMR (400 MHz, Chloroform-d) δ 8.06 (d, J=8.8 Hz, 2H), 7.17 (d, J=8.8 Hz, 2H), 5.38 (dd, J=8.9, 5.6 Hz, 1H), 3.53 (dd, J=17.6, 8.9 Hz, 1H), 3.14 (dd, J=17.6, 5.5 Hz, 1H). $^{13}$C NMR (101 MHz, Chloroform-d) δ 190.46, 175.97, 166.21 (d, J=256.8 Hz), 131.84 (d, J=9.5 Hz), 129.97 (d, J=3.0 Hz), 116.09 (d, J=22.1 Hz), 38.41, 38.22. $^{19}$F NMR (377 MHz, CDCl$_3$) δ −103.09. MS (ESI$^+$ m/z): (M+H) 274.9714 (M+H calc'd 274.9714).

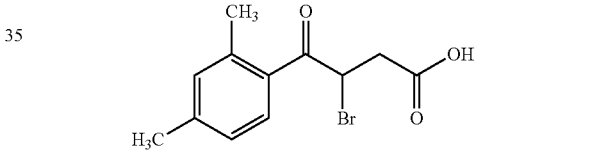

3-bromo-4-(2,4-dimethylphenyl)-4-oxobutanoic acid (4.4.09)

Using the general procedure for bromoketoacid preparation, 4.4.09 was isolated in quantitative yield. $^1$H NMR (400 MHz, Chloroform-d) δ 7.66 (d, J=8.0 Hz, 1H), 7.09 (d, J=7.7 Hz, 2H), 5.36 (dd, J=9.2, 5.4 Hz, 1H), 3.52 (dd, J=17.6, 9.2 Hz, 1H), 3.08 (dd, J=17.6, 5.4 Hz, 1H), 2.47 (s, 3H), 2.36 (s, 3H). $^{13}$C NMR (101 MHz, CDCl$_3$) δ 194.29, 176.56, 143.08, 140.38, 133.03, 131.80, 128.74, 126.43, 41.55, 38.43, 21.52, 21.25. MS (ESI$^+$ m/z): (M+H) 285.0118 (M+H calc'd 285.0126).

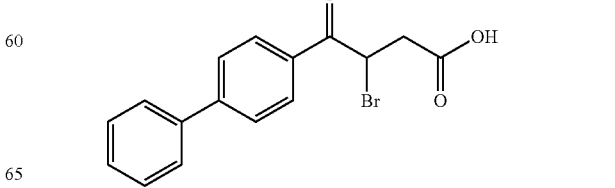

4-([1,1'-biphenyl]-4-yl)-3-bromo-4-oxobutanoic acid (4.4.10)

Using the general procedure for bromoketoacid preparation, 4.4.10 was isolated in quantitative yield. $^1$H NMR (400 MHz, Chloroform-d) δ 8.11 (d, J=8.5 Hz, 2H), 7.71 (d, J=8.5 Hz, 2H), 7.66-7.61 (m, 2H), 7.52-7.45 (m, 2H), 7.44-7.37 (m, 1H), 5.48 (dd, J=8.8, 5.7 Hz, 1H), 3.57 (dd, J=17.6, 8.8 Hz, 1H), 3.17 (dd, J=17.6, 5.6 Hz, 1H). $^{13}$C NMR (101 MHz, CDCl$_3$) δ 191.52, 175.84, 146.77, 139.63, 132.25, 129.69, 129.02, 128.48, 127.47, 127.33, 38.66, 38.25. MS (ESI$^+$ m/z): (M+H) 333.0121 (M+H calc'd 333.0121).

General Procedure for Preparation of Triazolothiadiazines (Compounds 4.5.01-18)

The triazole (1.1 equiv) and brominated ketoacid (1.0 equiv) were combined in a dry vessel and purged with N$_2$, then dissolved in DMF (0.1 M). The reaction was heated to 90° C. and stirred overnight. The crude reaction mixture was concentrated in vacuo and purified by silica chromatography to yield the triazolothiadiazine product.

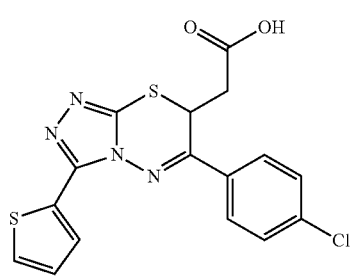

2-(6-(4-chlorophenyl)-3-(thiophen-2-yl)-7H-[1,2,4]triazolo[3,4-b][1,3,4]thiadiazin-7-yl)acetic acid (15)

Compounds 4.2.01 and 4.4.01 were combined in the general procedure for triazolothiadiazine formation, to generate 15 in 34% yield. NMR and MS characterization data were consistent with a commercially available standard (Enamine).

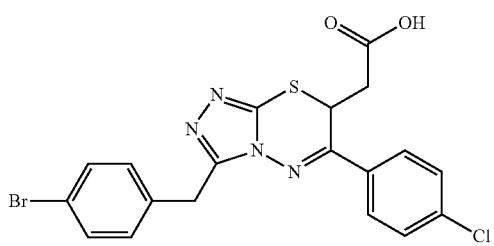

2-(3-(4-bromobenzyl)-6-(4-chlorophenyl)-7H-[1,2,4]triazolo[3,4-b][1,3,4]thiadiazin-7-yl)acetic acid (11)

Compounds 4.2.02 and 4.4.01 were combined in the general procedure for triazolothiadiazine formation, to generate 11 in 25% yield. NMR and MS characterization data were consistent with a commercially available standard (Enamine).

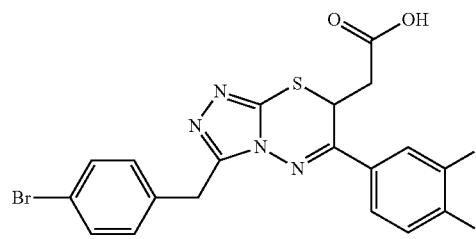

2-(3-(4-bromobenzyl)-6-(3,4-dichlorophenyl)-7H-[1,2,4]triazolo[3,4-b][1,3,4]thiadiazin-7-yl)acetic acid (16)

Compounds 4.2.02 and 4.4.02 were combined in the general procedure for triazolothiadiazine formation, to generate 16 in 79% yield. $^1$H NMR (500 MHz, Methanol-d$_4$) δ 7.98 (d, J=2.2 Hz, 1H), 7.78 (dd, J=8.5, 2.2 Hz, 1H), 7.60 (d, J=8.5 Hz, 1H), 7.39 (d, J=8.4 Hz, 2H), 7.16 (d, J=8.4 Hz, 2H), 4.96 (dd, J=9.4, 5.2 Hz, 1H), 4.27 (s, 2H), 2.56 (dd, J=16.6, 5.2 Hz, 1H), 2.46 (dd, J=16.6, 9.4 Hz, 1H). $^{13}$C NMR (126 MHz, MeOD) δ 170.61, 154.95, 152.99, 140.40, 135.97, 134.72, 133.05, 132.82, 131.56, 130.93, 130.43, 129.24, 127.00, 120.65, 36.93, 33.24, 29.66. MS (ESI$^+$ m/z): (M+H) 510.9398 (M+H calc'd 510.9393).

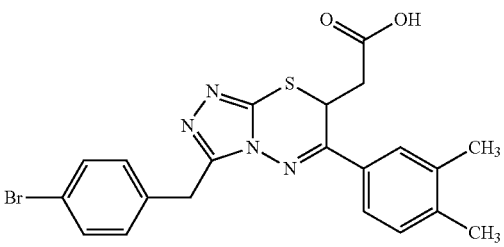

2-(3-(4-bromobenzyl)-6-(3,4-dimethylphenyl)-7H-[1,2,4]triazolo[3,4-b][1,3,4]thiadiazin-7-yl)acetic acid (17)

Compounds 4.2.02 and 4.4.03 were combined in the general procedure for triazolothiadiazine formation, to generate 17 in 24% yield. $^1$H NMR (500 MHz, Methanol-d$_4$) δ 7.71-7.65 (m, 2H), 7.48 (d, J=8.4 Hz, 2H), 7.30 (d, J=7.8 Hz, 1H), 7.27 (d, J=8.4 Hz, 2H), 5.06 (dd, J=10.2, 4.4 Hz, 1H), 4.36 (s, 2H), 2.65 (dd, J=16.6, 4.4 Hz, 1H), 2.51 (dd, J=16.6, 10.2 Hz, 1H), 2.35 (s, 6H). $^{13}$C NMR (126 MHz, MeOD) δ 170.27, 156.86, 152.87, 141.82, 140.25, 137.55, 134.87, 131.48, 130.45, 130.05, 129.73, 128.16, 124.92, 120.57, 36.43, 33.26, 29.65, 18.49. MS (ESI$^-$ m/z): (M−H) 469.0341 (M−H calc'd 469.0339).

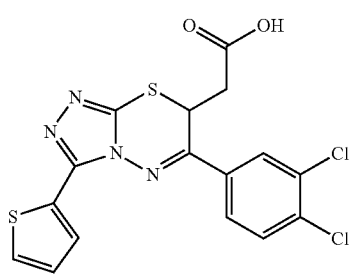

2-(6-(3,4-dichlorophenyl)-3-(thiophen-2-yl)-7H-[1,2,4]triazolo[3,4-b][1,3,4]thiadiazin-7-yl)acetic acid (18)

Compounds 4.2.01 and 4.4.02 were combined in the general procedure for triazolothiadiazine formation, to generate 18 in 67% yield. $^1$H NMR (500 MHz, Methanol-$d_4$) δ 8.30 (d, J=2.1 Hz, 1H), 8.04 (dd, J=8.5, 2.2 Hz, 1H), 8.01 (dd, J=3.7, 1.0 Hz, 1H), 7.78 (dd, J=5.0, 0.9 Hz, 1H), 7.75 (d, J=8.5 Hz, 1H), 7.28 (dd, J=5.0, 3.8 Hz, 1H), 5.18 (dd, J=9.4, 5.1 Hz, 1H), 2.86 (dd, J=16.7, 5.1 Hz, 1H), 2.77 (dd, J=16.7, 9.5 Hz, 1H). $^{13}$C NMR (126 MHz, MeOD) δ 170.47, 155.26, 148.58, 140.32, 136.15, 133.16, 132.78, 131.09, 129.74, 129.43, 129.30, 127.52, 127.20, 125.53, 36.74, 33.01. MS (ESI$^+$ m/z): (M+H) 424.9686 (M+H calc'd 424.9695).

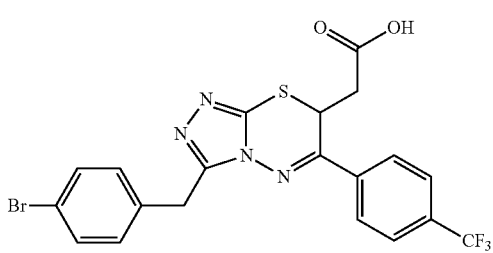

2-(3-(4-bromobenzyl)-6-(4-(trifluoromethyl)phenyl)-7H-[1,2,4]triazolo[3,4-b][1,3,4]thiadiazin-7-yl)acetic acid (20)

Compounds 4.2.02 and 4.4.05 were combined in the general procedure for triazolothiadiazine formation, to generate 20 in 13% yield. $^1$H NMR (500 MHz, Methanol-$d_4$) δ 8.16 (d, J=8.3 Hz, 2H), 7.85 (d, J=8.4 Hz, 2H), 7.49 (d, J=8.5 Hz, 2H), 7.28 (d, J=8.5 Hz, 2H), 5.13 (dd, J=9.7, 4.9 Hz, 1H), 4.38 (s, 1H), 2.68 (dd, J=16.5, 4.9 Hz, 1H), 2.56 (dd, J=16.5, 9.7 Hz, 1H). $^{13}$C NMR (126 MHz, MeOD) δ 170.76, 155.80, 153.10, 140.43, 136.26, 134.73, 131.54, 130.44, 128.10, 125.73, 120.65, 37.02, 33.58, 29.57. $^{19}$F NMR (377 MHz, MeOD) δ −64.60. MS (ESI$^-$ m/z): (M−H) 508.9903 (M−H calc'd 508.9900).

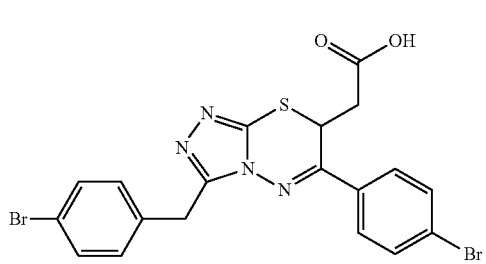

2-(3-(4-bromobenzyl)-6-(4-bromophenyl)-7H-[1,2,4]triazolo[3,4-b][1,3,4]thiadiazin-7-yl)acetic acid (19)

Compounds 4.2.02 and 4.4.04 were combined in the general procedure for triazolothiadiazine formation, to generate 19 in 14% yield. $^1$H NMR (500 MHz, Methanol-$d_4$) δ 7.89 (d, J=8.8 Hz, 2H), 7.72 (d, J=8.8 Hz, 2H), 7.48 (d, J=8.5 Hz, 2H), 7.27 (d, J=8.5 Hz, 2H), 5.08 (dd, J=9.8, 4.8 Hz, 1H), 4.36 (s, 2H), 2.69 (dd, J=16.7, 4.8 Hz, 1H), 2.56 (dd, J=16.7, 9.8 Hz, 1H). $^{13}$C NMR (126 MHz, MeOD) δ 170.15, 155.95, 153.00, 140.22, 134.75, 132.12, 131.52, 131.45, 126.64, 120.63, 36.42, 33.07, 29.57. MS (ESI$^-$ m/z): (M−H) 518.9131 (M−H calc'd 518.9131).

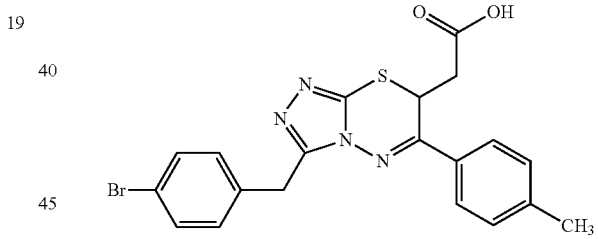

2-(3-(4-bromobenzyl)-6-(p-tolyl)-7H-[1,2,4]triazolo[3,4-b][1,3,4]thiadiazin-7-yl)acetic acid (21)

Compounds 4.2.02 and 4.4.06 were combined in the general procedure for triazolothiadiazine formation, to generate 21 in 16% yield. $^1$H NMR (500 MHz, Methanol-$d_4$) δ 7.88 (d, J=8.3 Hz, 2H), 7.48 (d, J=8.5 Hz, 2H), 7.36 (d, J=8.1 Hz, 2H), 7.27 (d, J=8.4 Hz, 2H), 5.05 (dd, J=10.4, 4.1 Hz, 1H), 4.36 (s, 2H), 2.59 (dd, J=16.5, 4.1 Hz, 1H), 2.45 (dd, J=16.5, 10.4 Hz, 1H), 2.43 (s, 3H). $^{13}$C NMR (126 MHz, MeOD) δ 171.32, 157.06, 152.85, 143.10, 140.43, 134.88, 131.49, 130.41, 129.56, 129.45, 127.28, 120.57, 37.34, 33.84, 29.57, 20.10. MS (ESI$^-$ m/z): (M−H) 455.0183 (M−H calc'd 455.0183).

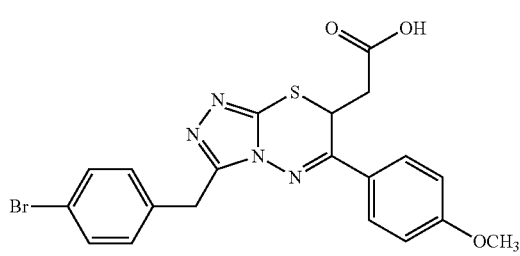

2-(3-(4-bromobenzyl)-6-(4-methoxyphenyl)-7H-[1,2,4]triazolo[3,4-b][1,3,4]thiadiazin-7-yl)acetic acid (22)

Compounds 4.2.02 and 4.4.07 were combined in the general procedure for triazolothiadiazine formation, to generate 22 in 13% yield. $^1$H NMR (500 MHz, Methanol-$d_4$) δ 7.96 (d, J=9.0 Hz, 2H), 7.48 (d, J=8.5 Hz, 2H), 7.27 (d, J=8.5 Hz, 2H), 7.08 (d, J=9.0 Hz, 2H), 5.07 (dd, J=10.3, 4.3 Hz, 1H), 4.36 (s, 2H), 3.89 (s, 3H), 2.64 (dd, J=16.6, 4.4 Hz, 1H), 2.49 (dd, J=16.6, 10.3 Hz, 1H). $^{13}$C NMR (126 MHz, MeOD) δ 167.91, 163.30, 156.62, 134.92, 131.48, 130.99, 130.41, 129.20, 128.46, 124.19, 120.57, 114.28, 54.69, 37.03, 33.42, 31.91. MS (ESI$^+$ m/z): (M+H) 473.0276 (M+H calc'd 473.0278).

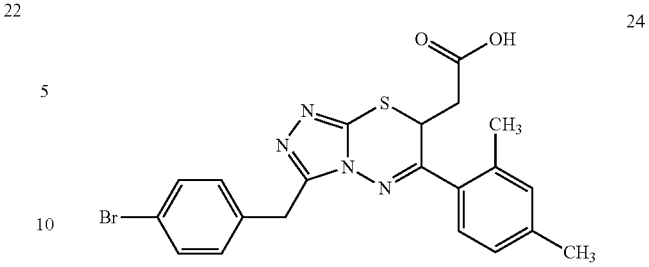

2-(3-(4-bromobenzyl)-6-(2,4-dimethylphenyl)-7H-[1,2,4]triazolo[3,4-b][1,3,4]thiadiazin-7-yl)acetic acid (4.5.11)

Compounds 4.2.02 and 4.4.09 were combined in the general procedure for triazolothiadiazine formation, to generate 24 in 47% yield. $^1$H NMR (500 MHz, Methanol-$d_4$) δ 7.37 (d, J=8.4 Hz, 2H), 7.24 (d, J=7.8 Hz, 1H), 7.09 (d, J=8.4 Hz, 2H), 7.07-7.03 (m, 2H), 4.57 (dd, J=9.3, 4.9 Hz, 1H), 4.25-4.15 (m, 2H), 2.54 (dd, J=16.6, 4.9 Hz, 1H), 2.45 (dd, J=16.6, 9.3 Hz, 1H), 2.26 (s, 3H), 2.19 (s, 3H). $^{13}$C NMR (126 MHz, MeOD) δ 170.21, 159.55, 140.99, 136.74, 134.85, 131.93, 131.51, 130.80, 130.24, 128.49, 126.68, 120.56, 36.49, 35.74, 29.45, 19.90, 19.43. MS (ESI$^+$ m/z): (M+H) 469.0338 (M+H calc'd 469.0339).

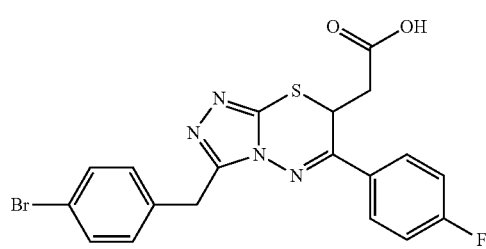

2-(3-(4-bromobenzyl)-6-(4-fluorophenyl)-7H-[1,2,4]triazolo[3,4-b][1,3,4]thiadiazin-7-yl)acetic acid (4.5.10)

Compounds 4.2.02 and 4.4.08 were combined in the general procedure for triazolothiadiazine formation, to generate 23 in 7% yield. $^1$H NMR (400 MHz, Methanol-$d_4$) δ 8.04 (d, J=9.0 Hz, 2H), 7.48 (d, J=8.4 Hz, 2H), 7.29 (d, J=8.5 Hz, 2H), 7.27 (d, J=7.5 Hz, 2H), 5.09 (dd, J=9.8, 4.7 Hz, 1H), 4.37 (s, 2H), 2.68 (dd, J=16.6, 4.7 Hz, 1H), 2.54 (dd, J=16.6, 9.8 Hz, 1H). $^{13}$C NMR (126 MHz, Methanol-$d_4$) δ 170.31, 165.26 (d, J=253.0 Hz), 154.44 (d, J=372.4 Hz), 140.21, 134.80, 130.98 (d, J=46.9 Hz), 130.96 (d, J=137.6 Hz), 129.99 (d, J=9.1 Hz), 128.67, 120.61, 115.89 (d, J=22.4 Hz), 36.50, 33.31, 29.56. $^{19}$F NMR (377 MHz, MeOD) δ −109.02. MS (ESI$^-$ m/z): (M−H) 458.9937 (M−H calc'd 458.9932).

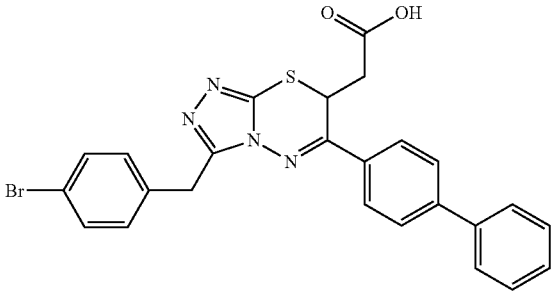

2-(6-([1,1'-biphenyl]-4-yl)-3-(4-bromobenzyl)-7H-[1,2,4]triazolo[3,4-b][1,3,4]thiadiazin-7-yl)acetic acid (4.5.12)

Compounds 4.2.02 and 4.4.10 were combined in the general procedure for triazolothiadiazine formation, to generate 25 in 60% yield. $^1$H NMR (500 MHz, Methanol-$d_4$) δ 7.98 (d, J=8.5 Hz, 2H), 7.72 (d, J=8.5 Hz, 2H), 7.61 (d, J=7.2 Hz, 2H), 7.44-7.35 (m, 4H), 7.31 (t, J=7.4 Hz, 1H), 7.19 (d, J=8.4 Hz, 2H), 5.02 (dd, J=10.3, 4.2 Hz, 1H), 4.29 (s, 2H), 2.55 (dd, J=16.4, 4.0 Hz, 1H), 2.41 (dd, J=16.4, 10.4 Hz, 1H). $^{13}$C NMR (126 MHz, MeOD) δ 156.79, 152.91, 144.91, 140.47, 139.48, 134.87, 131.52, 131.04, 130.43, 128.69, 127.96, 127.89, 127.28, 126.71, 120.61, 37.50, 33.87, 29.58. MS (ESI$^-$ m/z): (M−H) 517.0339 (M−H calc'd 517.0339).

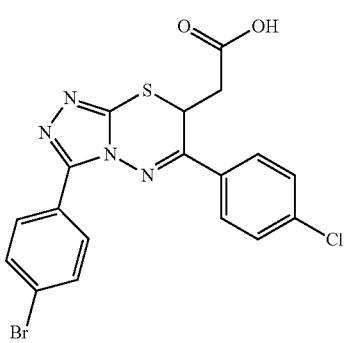

2-(3-(4-bromophenyl)-6-(4-chlorophenyl)-7H-[1,2,4]triazolo[3,4-b][1,3,4]thiadiazin-7-yl)acetic acid (4.5.13)

Compounds 4.2.03 and 4.4.01 were combined in the general procedure for triazolothiadiazine formation, to generate 26 in 39% yield. $^1$H NMR (500 MHz, Methanol-$d_4$) δ 8.05 (d, J=8.7 Hz, 1H), 7.99 (d, J=8.5 Hz, 1H), 7.76 (d, J=8.5 Hz, 1H), 7.59 (d, J=8.7 Hz, 1H), 5.16 (dd, J=9.7, 4.8 Hz, 1H), 2.83 (dd, J=16.5, 4.9 Hz, 1H), 2.75 (dd, J=16.4, 9.6 Hz, 1H). MS (ESI$^+$ m/z): (M+H) 462.9625 (M+H calc'd 462.9626).

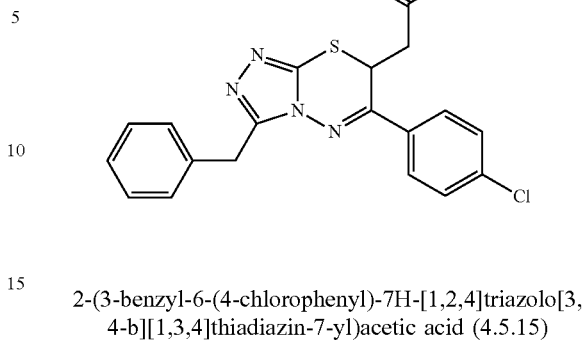

2-(3-benzyl-6-(4-chlorophenyl)-7H-[1,2,4]triazolo[3,4-b][1,3,4]thiadiazin-7-yl)acetic acid (4.5.15)

Compounds 4.2.05 and 4.4.01 were combined in the general procedure for triazolothiadiazine formation, to generate 28 in 36% yield. $^1$H NMR (500 MHz, Methanol-$d_4$) δ 7.86 (d, J=8.8 Hz, 2H), 7.45 (d, J=8.8 Hz, 2H), 7.24-7.18 (m, 4H), 7.16-7.10 (m, 1H), 4.96 (dd, J=9.9, 4.7 Hz, 1H), 4.29 (s, 2H), 2.52 (dd, J=16.6, 4.7 Hz, 1H), 2.40 (dd, J=16.6, 9.9 Hz, 1H). $^{13}$C NMR (126 MHz, MeOD) δ 170.43, 155.84, 153.48, 140.18, 138.16, 135.52, 131.06, 129.05, 128.93, 128.44, 128.38, 126.79, 36.58, 33.27, 30.16. MS (ESI$^-$ m/z): (M-H) 397.0532 (M-H calc'd 397.0532).

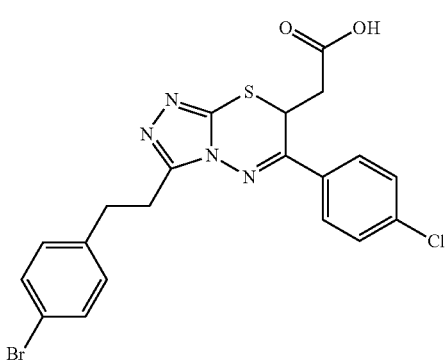

2-(3-(4-bromophenethyl)-6-(4-chlorophenyl)-7H-[1,2,4]triazolo[3,4-b][1,3,4]thiadiazin-7-yl)acetic acid (4.5.14)

Compounds 4.2.04 and 4.4.01 were combined in the general procedure for triazolothiadiazine formation, to 27 in 32% yield. $^1$H NMR (500 MHz, Methanol-$d_4$) δ 7.97 (d, J=8.7 Hz, 2H), 7.58 (d, J=8.7 Hz, 2H), 7.33 (d, J=8.4 Hz, 2H), 7.12 (d, J=8.3 Hz, 2H), 5.01 (dd, J=10.5, 4.1 Hz, 1H), 2.55 (dd, J=16.6, 4.1 Hz, 1H), 2.35 (dd, J=16.6, 10.6 Hz, 1H), 1.31 (t, J=7.3 Hz, 4H). MS (ESI$^+$ m/z): (M+H) 490.9939 (M+H calc'd 490.9939).

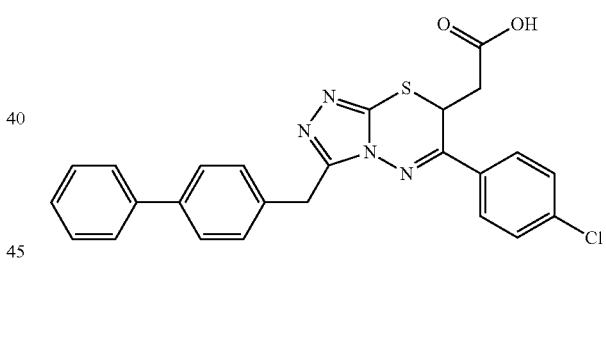

2-(3-([1,1'-biphenyl]-4-ylmethyl)-6-(4-chlorophenyl)-7H-[1,2,4]triazolo[3,4-b][1,3,4]thiadiazin-7-yl)acetic acid (4.5.16)

Compounds 4.2.06 and 4.4.01 were combined in the general procedure for triazolothiadiazine formation, to generate 29 in 60% yield. $^1$H NMR (400 MHz, Methanol-$d_4$) δ 7.97 (d, J=8.7 Hz, 2H), 7.62-7.50 (m, 6H), 7.43-7.35 (m, 4H), 7.34-7.26 (m, 1H), 5.08 (dd, J=9.7, 4.9 Hz, 1H), 4.43 (s, 2H), 2.68 (dd, J=16.7, 4.9 Hz, 1H), 2.56 (dd, J=16.7, 9.7 Hz, 1H). $^{13}$C NMR (126 MHz, MeOD) δ 172.80, 156.53, 153.33, 140.59, 140.42, 139.94, 138.07, 134.69, 131.22, 129.06, 128.93, 128.91, 128.46, 126.98, 126.49, 38.73, 34.61, 29.78. MS (ESI$^-$ m/z): (M-H) 473.0848 (M-H calc'd 473.0845).

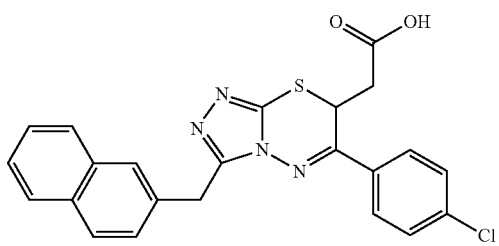

2-(6-(4-chlorophenyl)-3-(naphthalen-2-ylmethyl)-7H-[1,2,4]triazolo[3,4-b][1,3,4]thiadiazin-7-yl)acetic acid (4.5.17)

Compounds 4.2.07 and 4.4.01 were combined in the general procedure for triazolothiadiazine formation, to generate 30 in 32% yield. $^1$H NMR (400 MHz, Methanol-$d_4$) δ 7.91 (d, J=8.7 Hz, 2H), 7.87-7.78 (m, 4H), 7.53-7.43 (m, 5H), 5.04 (dd, J=9.9, 4.7 Hz, 1H), 4.56 (s, 2H), 2.60 (dd, J=16.6, 4.7 Hz, 1H), 2.49 (dd, J=16.6, 9.9 Hz, 1H). $^{13}$C NMR (126 MHz, MeOD) δ 174.52, 172.81, 156.43, 153.24, 140.64, 138.01, 133.60, 132.98, 132.55, 131.15, 128.99, 128.86, 128.18, 127.30, 127.23, 126.33, 126.00, 125.56, 38.73, 34.61, 30.40. MS (ESI$^+$ m/z): (M+H) 449.0831 (M+H calc'd 449.0834).

2-(3-([1,1'-biphenyl]-4-ylmethyl)-6-(3,4-dichlorophenyl)-7H-[1,2,4]triazolo[3,4-b][1,3,4]thiadiazin-7-yl)acetic acid (4.5.18)

Compounds 4.2.06 and 4.4.02 were combined in the general procedure for triazolothiadiazine formation, to 31 in 54% yield. $^1$H NMR (500 MHz, Methanol-$d_4$) δ 8.08 (d, J=1.9 Hz, 1H), 7.86 (dd, J=8.5, 1.9 Hz, 1H), 7.66 (d, J=8.5 Hz, 1H), 7.61-7.54 (m, 4H), 7.38 (t, J=7.4 Hz, 4H), 7.29 (t, J=7.3 Hz, 1H), 5.05 (dd, J=9.2, 5.3 Hz, 1H), 4.43 (s, 2H), 2.67 (dd, J=16.7, 5.4 Hz, 1H), 2.58 (dd, J=16.6, 9.3 Hz, 1H). $^{13}$C NMR (126 MHz, MeOD) δ 173.79, 170.28, 163.44, 154.84, 153.44, 140.44, 140.27, 140.05, 135.93, 134.51, 133.02, 132.84, 130.90, 129.26, 128.92, 128.42, 127.03, 126.97, 126.50, 36.64, 33.05, 29.94. MS (ESI$^-$ m/z): (M–H) 507.0452 (M–H calc'd 507.0455).

General procedure for preparation of esters (compounds 32 and 14): A solution of the carboxylic acid (1.0 equiv., 0.1 M) in dry methanol was prepared in a dry flask with condensing column attached. The solution was cooled to 0° C., then thionyl chloride (10 equiv.) was added dropwise. The reaction was heated at 65° C. for three hours, then cooled to room temperature and concentrated. The reaction mixture was purified by column chromatography (2:1 hexanes/ethyl acetate).

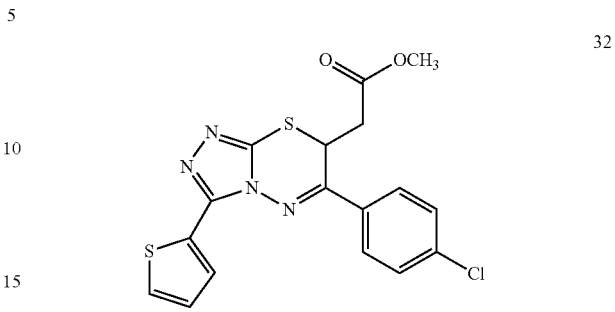

Methyl-2-(6-(4-chlorophenyl)-3-(thiophen-2-yl)-7H-[1,2,4]triazolo[3,4-b][1,3,4]thiadiazin-7-yl)acetate (32)

According to the general procedure for ester formation, compound 15 was converted to the methyl ester 32, and isolated in 89% yield. $^1$H NMR (500 MHz, Methanol-$d_4$) δ 8.13 (d, J=8.6 Hz, 2H), 8.02 (d, J=3.5 Hz, 1H), 7.76 (d, J=4.9 Hz, 1H), 7.62 (d, J=8.6 Hz, 2H), 7.30-7.24 (m, 1H), 5.23 (dd, J=9.4, 5.2 Hz, 1H), 3.63 (s, 3H), 2.90 (dd, J=16.5, 5.2 Hz, 1H), 2.83 (dd, J=16.5, 9.4 Hz, 1H). $^{13}$C NMR (126 MHz, MeOD) δ 169.20, 155.94, 148.59, 140.09, 138.42, 131.01, 129.68, 129.26, 129.23, 129.16, 127.51, 125.64, 51.40, 36.53, 32.90. MS (ESI$^+$ m/z): (M+H) 405.0247 (M+H calc'd 405.0242).

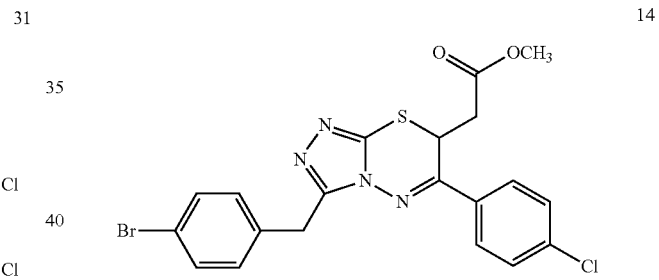

Methyl-2-(3-(4-bromobenzyl)-6-(4-chlorophenyl)-7H-[1,2,4]triazolo[3,4-b][1,3,4]thiadiazin-7-yl)acetate (14)

According to the general procedure for ester formation, compound 11 was converted to the methyl ester 14, and isolated in 31% yield. $^1$H NMR (500 MHz, Chloroform-d) δ 7.80 (d, J=8.7 Hz, 2H), 7.49 (d, J=8.7 Hz, 2H), 7.42 (d, J=8.4 Hz, 2H), 7.20 (d, J=8.3 Hz, 2H), 4.78 (dd, J=10.0, 4.5 Hz, 1H), 4.34 (s, 2H), 2.63 (dd, J=16.8, 10.0 Hz, 1H), 2.54 (dd, J=16.8, 4.5 Hz, 1H). $^{13}$C NMR (126 MHz, CDCl$_3$) δ 169.04, 154.13, 152.70, 139.25, 138.97, 134.44, 131.90, 130.61, 130.57, 129.74, 128.60, 121.21, 52.75, 36.84, 32.85, 30.49. MS (ESI$^+$ m/z): (M+H) 490.9932 (M calc'd 490.9939)

General procedure for preparation of amides (compounds 34 and 35): A solution of the carboxylic acid (1.0 equiv., 0.04 M) in dry DMF was prepared in a dry vial. The solution was cooled to 0° C., then HATU (1.5 equiv., 0.15 M) in solution in DMF was added dropwise. After stirring for 5 minutes at 0° C., the reaction was warmed to room temperature and allylamine (2.0 equiv.) was added. The reaction was stirred at room temperature overnight, then concentrated. The reaction mixture was purified by column chromatography (gradient from 4:1 hexanes/ethyl acetate 1:1 hexanes/ethyl acetate+1% acetic acid).

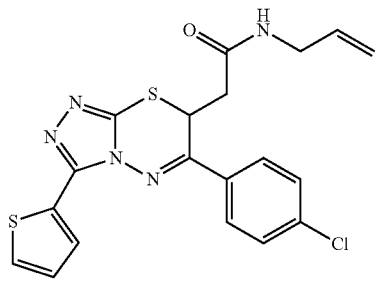

N-allyl-2-(6-(4-chlorophenyl)-3-(thiophen-2-yl)-7H-[1,2,4]triazolo[3,4-b][1,3,4]thiadiazin-7-yl)acetamide (34)

According to the general procedure for amide formation, compound 15 was converted to the allyl amide 34, and isolated in 13% yield. $^1$H NMR (500 MHz, Chloroform-d) δ 8.06 (d, J=8.6 Hz, 2H), 7.82 (d, J=3.6 Hz, 1H), 7.55 (d, J=8.6 Hz, 2H), 7.45 (d, J=5.0 Hz, 1H), 7.12-7.02 (m, 1H), 5.85 (ddt, J=16.0, 10.7, 5.6 Hz, 1H), 5.26 (d, J=17.1 Hz, 1H), 5.17 (d, J=10.3 Hz, 1H), 5.01 (dd, J=11.1, 3.3 Hz, 1H), 4.12 (q, J=7.2 Hz, 2H), 4.07-3.85 (m, 2H), 2.85 (dd, J=15.0, 11.2 Hz, 1H), 2.71 (dd, J=15.0, 3.4 Hz, 1H). $^{13}$C NMR (126 MHz, CDCl$_3$) δ 166.17, 153.99, 147.55, 138.12, 137.93, 132.35, 129.59, 128.75, 127.97, 127.79, 126.57, 125.36, 116.01, 41.39, 37.44, 32.78. MS (ESI$^+$ m/z): (M+H) 430.0558 (M+H calc'd 430.0558).

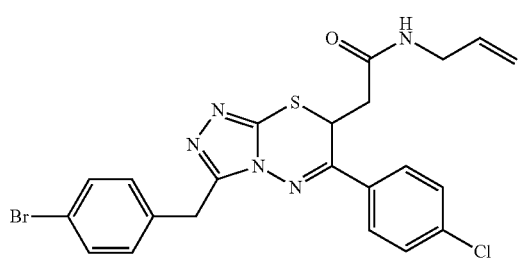

N-allyl-2-(3-(4-bromobenzyl)-6-(4-chlorophenyl)-7H-[1,2,4]triazolo[3,4-b][1,3,4]thiadiazin-7-yl)acetamide (35)

According to the general procedure for amide formation, compound 11 was converted to the allyl amide 35, and isolated in 84% yield. $^1$H NMR (500 MHz, Chloroform-d) δ 7.87 (d, J=8.7 Hz, 2H), 7.49 (d, J=8.7 Hz, 2H), 7.43 (d, J=8.4 Hz, 2H), 7.18 (d, J=8.4 Hz, 2H), 5.86-5.72 (m, 1H), 5.21 (dd, J=17.1, 1.4 Hz, 1H), 5.13 (dd, J=10.2, 1.3 Hz, 1H), 4.93 (dd, J=10.7, 3.5 Hz, 1H), 4.25 (q, J=15.6 Hz, 2H), 3.98-3.81 (m, 2H), 2.66 (dd, J=14.9, 10.8 Hz, 1H), 2.51 (dd, J=14.9, 3.5 Hz, 1H). $^{13}$C NMR (126 MHz, CDCl$_3$) δ 175.65, 167.30, 155.08, 152.38, 139.47, 138.94, 134.27, 133.40, 131.85, 130.53, 129.66, 128.62, 121.19, 116.90, 42.38, 38.52, 33.97, 30.43. MS (ESI$^+$ m/z): (M+H) 516.0259 (M+H calc'd 516.0255).

Scheme 4: Synthesis of Inhibitor compounds 12 and 13

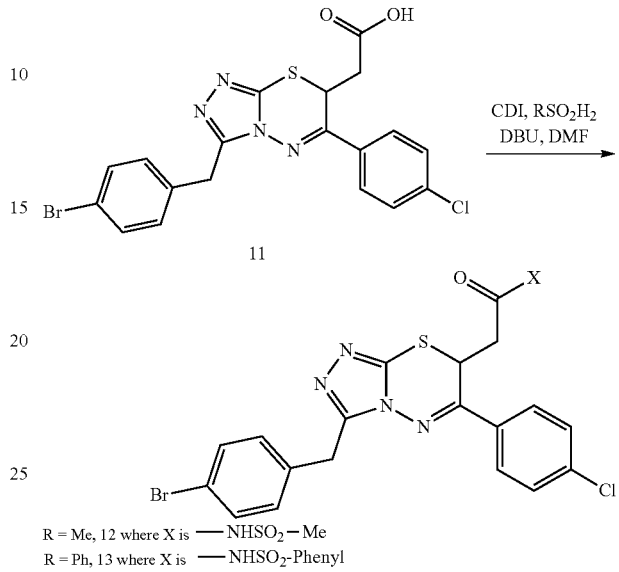

R = Me, 12 where X is —NHSO$_2$—Me
R = Ph, 13 where X is —NHSO$_2$-Phenyl

Scheme 4 illustrates exemplary synthesis of inhibitors of formula II from triazolothiadiazine carboxylic acids.

2-(3-(4-bromobenzyl)-6-(4-chlorophenyl)-7H-[1,2,4]triazolo[3,4-b][1,3,4]thiadiazin-7-yl)-N-(methylsulfonyl)acetamide (12)

Using the general procedure for sulfonamide coupling, with 11 as the carboxylic acid and where RSO$_2$NH$_2$ is methanesulfonamide, 12 was isolated in 60% yield. $^1$H NMR (500 MHz, Methanol-d4) δ 7.99 (d, J=8.7 Hz, 2H), 7.55 (d, J=8.7 Hz, 2H), 7.49 (d, J=8.4 Hz, 2H), 7.27 (d, J=8.4 Hz, 2H), 5.11 (dd, J=9.9, 4.9 Hz, 1H), 4.37 (s, 2H), 2.57 (dd, J=15.7, 4.9 Hz, 1H), 2.45 (dd, J=15.7, 9.9 Hz, 1H). $^{13}$C NMR (126 MHz, MeOD) δ 175.02, 157.91, 154.47, 142.14, 139.68, 136.38, 133.09, 132.73, 131.99, 130.59, 122.14, 41.81, 40.52, 35.49, 31.09. MS (ESI+m/z): (M+H) 553.9717 (M calc'd 553.9718).

2-(3-(4-bromobenzyl)-6-(4-chlorophenyl)-7H-[1,2,4]triazolo[3,4-b][1,3,4]thiadiazin-7-yl)-N-(phenylsulfonyl)acetamide (13)

Using the general procedure for sulfonamide coupling, with 11 as the carboxylic acid and where RSO$_2$NH$_2$ is benzenesulfonamide, 13 was isolated in 46% yield. $^1$H NMR (500 MHz, Methanol-d4) δ 7.93-7.87 (m, 4H), 7.58 (t, J=7.4 Hz, 1H), 7.53-7.46 (m, 6H), 7.25 (d, J=8.4 Hz, 2H), 5.02 (dd, J=9.9, 4.8 Hz, 1H), 4.35 (s, 2H), 2.55 (dd, J=16.0, 4.8 Hz, 1H), 2.45 (dd, J=16.0, 9.9 Hz, 1H). $^{13}$C NMR (126 MHz, MeOD) δ 175.43, 157.52, 154.47, 143.15, 141.90, 139.69, 136.34, 133.64, 133.09, 132.41, 131.96, 130.58, 130.45, 129.72, 128.79, 122.15, 40.78, 34.88, 31.08. MS (ESI+m/z): (M+H) 615.9876 (M calc'd 615.9874).

Scheme 5: Synthesis of carboxylic esters of compound 11

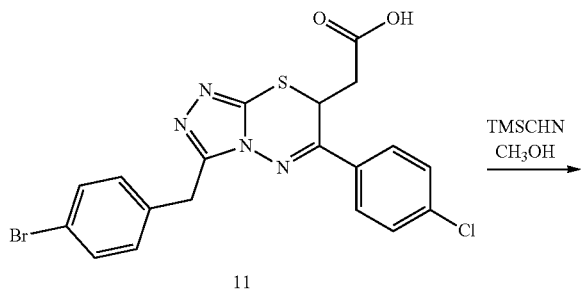

Scheme 5 illustrates exemplary synthesis of carboxylic acid esters of compound 11.

Methyl 2-(3-(4-bromobenzyl)-6-(4-chlorophenyl)-7H-[1,2,4]triazolo[3,4-b][1,3,4]thiadiazin-7-yl)acetate (14)

A solution of 11 (16.5 mg, 0.034 mmol) in MeOH (340 μL) was cooled to 0° C., and thionyl chloride (25 μL, 0.34 mmol) was added dropwise. The mixture was heated at 65° C. for 6 hours. The reaction mixture was concentrated in vacuo and purified with flash chromatography over $SiO_2$ (2:1 hexanes/EtOAc) to afford 14 in 31% yield (5.2 mg, 0.0106 mmol). $^1$H NMR (500 MHz, Chloroform-d) δ 7.80 (d, J=8.7 Hz, 2H), 7.49 (d, J=8.7 Hz, 2H), 7.42 (d, J=8.4 Hz, 2H), 7.20 (d, J=8.3 Hz, 2H), 4.78 (dd, J=10.0, 4.5 Hz, 1H), 4.34 (s, 2H), 2.63 (dd, J=16.8, 10.0 Hz, 1H), 2.54 (dd, J=16.8, 4.5 Hz, 1H). $^{13}$C NMR (126 MHz, $CDCl_3$) δ 169.04, 154.13, 152.70, 139.25, 138.97, 134.44, 131.90, 130.61, 130.57, 129.74, 128.60, 121.21, 52.75, 36.84, 32.85, 30.49. MS (ESI+m/z): (M+H) 490.9932 (M calc'd 490.9939).

Example 2: Compound Characterization by Dynamic Light Scattering

A representative subset of the compounds (1, 2, and 4) were evaluated for aggregation by Dynamic Light Scattering (DLS), see Table 1. Samples for DLS analysis were prepared in 50 mM sodium phosphate buffer from DMSO inhibitor stocks, at a final DMSO concentration of 1%, and a range of final concentrations of inhibitor. Samples that displayed a scattering of less than 5×104, which is the lower detection limit of the instrument, were considered not to aggregate.

TABLE 1

| Results of Aggregation Assays | | |
|---|---|---|
| Compound | Conc. (uM) | Aggregates observed? |
| 1 | 100 | Yes |
| | 50 | No |
| | 25 | No |
| | 10 | No |
| 2 | 100 | No |
| | 50 | No |
| | 25 | No |
| | 10 | No |
| 4 | 100 | Yes |
| | 50 | No |
| | 25 | No |
| | 10 | No |

Example 3: Assays for Inhibitory Activity

A. MtbUGM Activity Assay

Recombinant MtbUGM was produced according to published protocols, and enzyme activity was evaluated using a previously published HPLC assay. [Carlson, E. E., May, J. F., and Kiessling, L. L. (2006) Chemical probes of UDP-galactopyranose mutase, Chem. Biol. 13, 825-837]. 20 nM MtbUGM was incubated in 50 mM sodium phosphate buffer (pH 7.0) with 20 mM sodium dithionite and 20 μM UDP-Galf in the absence or presence of an inhibitor (added as a DMSO stock at a final concentration of 1% DMSO). After a 40 second incubation, the reaction was quenched with 1:1 chloroform/methanol. The aqueous portion was separated and analyzed on a Dionex Carbopac PA-100 column to quantify conversion of UDP-Galf to UDP-Galp. Relative enzyme activity was derived by normalizing activity in the presence of inhibitors against the activity of the enzyme alone.

B. Microplate Alamar Blue Assay

*M. smegmatis* was grown to saturation over 48 hours at 37° C. in Middlebrook 7H9 media with Albumin Dextrose Catalase (ADC) enrichment and 0.05% Tween80. The culture was diluted to OD600=~0.02 in LB liquid media and added to 96-well plates at a final volume of 100 μL, with added inhibitor concentrations in two-fold dilutions. Perimeter wells were filled with sterile water. After 24 hours at 37° C. in a shaking incubator, 10 μL of the Alamar Blue reagent was added to each well. The plate was incubated for an additional 4 hours at 37° C., at which point fluorescence emission at 585 nm was measured using a plate reader. The lowest inhibitor concentration at which 99% or greater growth inhibition was observed was determined to be the MIC.

C. Agar Disk Diffusion Assay

*M. smegmatis* was grown to saturation over 48 hours at 37° C. in Middlebrook 7H9 media with Albumin Dextrose Catalase (ADC) enrichment and 0.05% Tween80. The culture was diluted to OD600=~0.2 in LB liquid media and 100 μL of dilute culture was spread onto LB agar plates, then allowed to soak into the agar for 1 hour at room temperature. Sterile disks (3 mm diameter) were impregnated with a solution of inhibitor in DMSO (1.5 μL) and placed on top of the bacterial lawn. Compounds 1-10 were tested using a 10 mM inhibitor stock, and compounds 11-13 were tested using a 50 mM inhibitor stock. The plates were incubated for 72 hours at 37° C., at which point a lawn of bacteria was visible. Zones of inhibition were measured as the average diameter of the region around a cloning disk where bacterial growth was not visible. For each disk, three diameter measurements were taken and averaged.

Example 4: Evaluation of Inhibitory Activity of N-Acylsulfonamides

A key feature of the 2-aminothiazole inhibitor scaffold is a carboxylic acid moiety hypothesized to interact with the MtbUGM active site residues Arg291 and Arg180. [Chad, J. M., Sarathy, K. P., Gruber, T. D., Addala, E., Kiessling, L. L., and Sanders, D. A. (2007) Site-directed mutagenesis of UDP-galactopyranose mutase reveals a critical role for the active-site, conserved arginine residues, Biochemistry 46, 6723-6732]. These residues, conserved across UGM homologs, play a critical role in binding the pyrophosphate group of the natural substrates UDP-Galp and UDP-Galf. The carboxylate moiety of the 2-aminothiazole inhibitors is crucial for activity against UGM, suggesting that it can mimic pyrophosphate binding interactions. [Dykhuizen et al. (2008)]. Still, negatively charged functional groups such as carboxylates are known to hinder diffusion through lipid bilayer membranes. [Klemm, A. R., Pell, K. L., Anderson, L. M., Andrew, C. L., and Lloyd, J. B. (1998) Lysosome membrane permeability to anions, Biochim. Biophys. Acta 1373, 17-26; Walter, A., and Gutknecht, J. (1984) Mono-carboxylic acid permeation through lipid bilayer membranes, J. Membr. Biol. 77, 255-264.] The present work investigates the replacement of the carboxylate with an N-acylsulfonamide functionality. N-acylsulfonamides have lower $pK_a$ values to those of carboxylic acids, and are expected to be ionized under physiological conditions. Still, the N-acylsulfonamide group has an additional substituent (Scheme 2) that could alter overall lipophilicity or engage in additional binding interactions. Additionally, the charge in N-acylsulfonamides is delocalized over more atoms than in the case of a carboxylate. Through these mechanisms, substitution of a carboxylate with an N-acylsulfonamide group could improve antimycobacterial efficacy while facilitating interactions crucial for UGM active site binding.

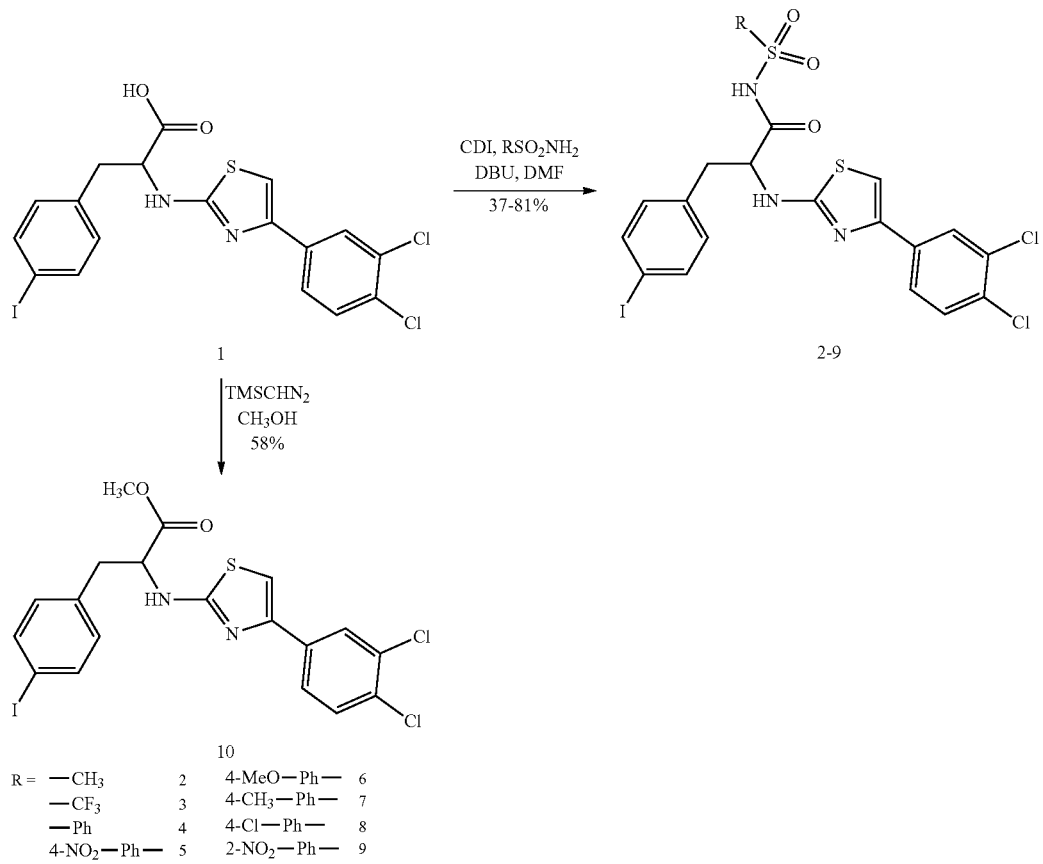

Scheme 6: Late-stage carboxylate modifications

Abbreviations: CDI≡1,1-carbonyldiimidazole, DBU≡1,8-diazabicycloundec-7-ene

The strategy used was to implement a late-stage functionalization of the most potent 2-aminothiazole derivative 1 to generate a collection of N-acylsulfonamide analogs (Scheme 6). Coupling of 1 to a range of commercially available sulfonamides yielded the desired N-acylsulfonamides 2-9 (Scheme 2). [Ronn, R., Sabnis, Y. A., Gossas, T., Akerblom, E., Danielson, U. H., Hallberg, A., and Johansson, A. (2006) Exploration of acyl sulfonamides as carboxylic acid replacements in protease inhibitors of the hepatitis C virus full-length NS3, Bioorg. Med. Chem. 14, 544-559.] For comparison, a methyl ester variant, 10, was synthesized. We hypothesized that replacing the carboxylate with a charge-neutral ester species would significantly diminish inhibitor potency. In contrast, the modification with N-acylsulfonamide groups should result in inhibitory potencies comparable or superior to that of the carboxylate.

To explore the effect of carboxylate modifications, MtbUGM activity was compared in the presence of 50 μM of compound 1, 2, or 10 (FIG. 1). The ability of recombinantly produced MtbUGM to generate UDP-Galp from UDP-Galf was evaluated in the presence of each compound using a previously reported HPLC-based assay. Under these conditions, free carboxylate 1 inhibited greater than 90% of UGM activity. In contrast, methyl ester 10 inhibits only 30% of activity, indicating that the carboxylate anion is important for inhibitor potency. The methylsulfonamide-modified 2 displayed similar levels of inhibition (>90%) as 1. To test whether this inhibition arose from compound aggregation, a non-specific mode of inhibition, [Seidler, J., McGovern, S. L., Doman, T. N., and Shoichet, B. K. (2003) Identification and prediction of promiscuous aggregating inhibitors among known drugs, J. Med. Chem. 46, 4477-4486; Feng, B. Y., Shelat, A., Doman, T. N., Guy, R. K., and Shoichet, B. K. (2005) High-throughput assays for promiscuous inhibitors, Nat. Chem. Biol. 1, 146-148] the solution properties of a representative set of compounds (1, 2, and 4) were evaluated using dynamic light scattering (DLS). No aggregation was observed for any of these compounds at concentrations up to 50 μM (see Examples). These data support our hypothesis that the negatively charged carboxylate is crucial to effectively mimic pyrophosphate binding in the active site, and that the anionic N-acylsulfonamide is capable of preserving this important interaction.

To characterize the consequence of carboxylate replacement, we generated full inhibition curves for each N-acylsulfonamide derivative and the half-maximal inhibitory concentration ($IC_{50}$) was calculated. The $IC_{50}$ values for compounds 2-9 were comparable to that of the precursor 1 ($IC_{50}$=6 μM), and they range from 1-18 μM (Table 2). These data imply that the N-acylsulfonamide modification is not only tolerated by the UGM active site, but in some cases can impart enhanced binding affinity. Though it was possible that the stronger binding could have been due to the sulfonamide moiety itself, that model suggests 2 would be a more potent inhibitor than 1. The observed inhibition data do not support this hypothesis. We postulate that the enhanced inhibition observed for compounds 5 and 7-9 arises from the interaction of the aromatic substituents with an extended binding site. Electronic differences between the aryl substituents likely also influence in vitro potency, but it is difficult to make predictions as both electronic and steric effects should contribute to overall activities.

Having identified analogs 2-9 as effective UGM inhibitors, we next evaluated their potency in cell-based assays. Growth inhibition of M. smegmatis was assessed in liquid culture using a Microplate Alamar Blue Assay, [Collins, L., and Franzblau, S. G. (1997) Microplate alamar blue assay versus BACTEC 460 system for high-throughput screening of compounds against Mycobacterium tuberculosis and Mycobacterium avium, Antimicrob. Agents Chemother. 41, 1004-1009; Magnet, S., Hartkoorn, R. C., Szekely, R., Pato, J., Triccas, J. A., Schneider, P., Szantai-Kis, C., Orfi, L., Chambon, M., Banfi, D., Bueno, M., Turcatti, G., Keri, G., and Cole, S. T. (2010) Leads for antitubercular compounds from kinase inhibitor library screens, Tuberculosis 90, 354-360] and from these data the minimum inhibitory concentration (MIC) was determined for each compound (Table 3). Variation in inhibitor efficacy was observed when using different growth media. This observation is not surprising, as previous studies have noted differences in the potency of mycobacterial growth inhibitors based on culture conditions. [Pethe, K., et al. (2010) A chemical genetic screen in Mycobacterium tuberculosis identifies carbon-source-dependent growth inhibitors devoid of in vivo efficacy, Nat. Commun. 1, 57; Miller, C. H., Nisa, S., Dempsey, S., Jack, C., and O'Toole, R. (2009) Modifying culture conditions in chemical library screening identifies alternative inhibitors of mycobacteria, Antimicrob. Agents Chemother. 53, 5279-5283] The most potent inhibitors in liquid culture conditions were 7-9, each of which displayed at least a four-fold enhancement in growth inhibition compared to the carboxylic acid precursor 1.

TABLE 2

In vitro inhibition of MtbUGM by Compounds 1-9.

| Compound | R | $IC_{50}$ (μM)[a] |
|---|---|---|
| 1 | — | 6 ± 2 |
| 2 | $CH_3$ | 12 ± 5 |
| 3 | $CF_3$ | 16 ± 10 |
| 4 | $C_6H_5$ | 7 ± 2 |
| 5 | 4-$NO_2$—$C_6H_4$ | 4 ± 1 |
| 6 | 4-$OCH_3$—$C_6H_4$ | 18 ± 9 |
| 7 | 4-$CH_3$—$C_6H_4$ | 1 ± 1 |
| 8 | 4-Cl—$C_6H_4$ | 3 ± 1 |
| 9 | 2-$NO_2$—$C_6H_4$ | 2 ± 1 |

[a]Relative activity of recombinant MtbUGM was evaluated for a range of inhibitor concentrations. Data were analyzed using non-linear regression analysis using a one-site binding model. The calculated half-maximal inhibition concentration ($IC_{50}$). Is provided with standard deviation (n = 3).

TABLE 3

M. smegmatis growth inhibition by Compounds 1-9

| Compound | R | MIC (μM) | Inhibition zone (mm) |
|---|---|---|---|
| 1 | — | 50 | 5.0 ± 0.1 |
| 2 | $CH_3$ | 25 | 7.0 ± 0.1 |
| 3 | $CF_3$ | 50 | 7.7 ± 0.6 |
| 4 | $C_6H_5$ | 25 | 7.3 ± 0.6 |
| 5 | 4-$NO_2$—$C_6H_4$ | 50 | 4.2 ± 0.3 |
| 6 | 4-$OCH_3$—$C_6H_4$ | 25 | 6.0 ± 0.1 |
| 7 | 4-$CH_3$—$C_6H_4$ | 12.5 | 6.0 ± 0.6 |
| 8 | 4-Cl—$C_6H_4$ | 12.5 | 6.3 ± 0.6 |
| 9 | 2-$NO_2$—$C_6H_4$ | 12.5 | 5.7 ± 0.1 |

Figure 2:
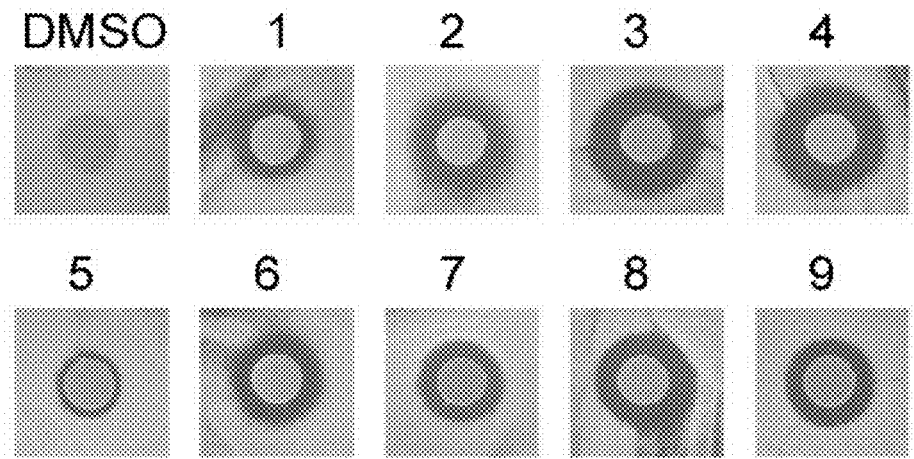
FIG. 2 illustrates Agar disk diffusion assays with *M. smegmatis* and compounds 1-9. Representative images of triplicate samples are shown. Quantification of growth inhibition zones can be found in Table 2.
Figure 3A:
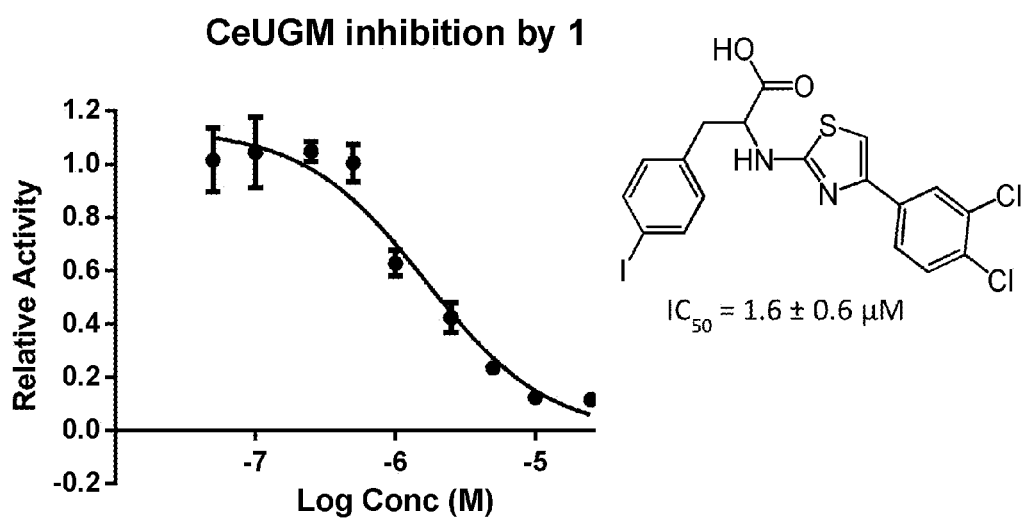
FIGS. 3A-3C are graphs of CeUGM inhibition by certain compounds of the invention (see Example 7). The inhibitors are illustrated and the $IC_{50}$s are given.
Figure 3B:
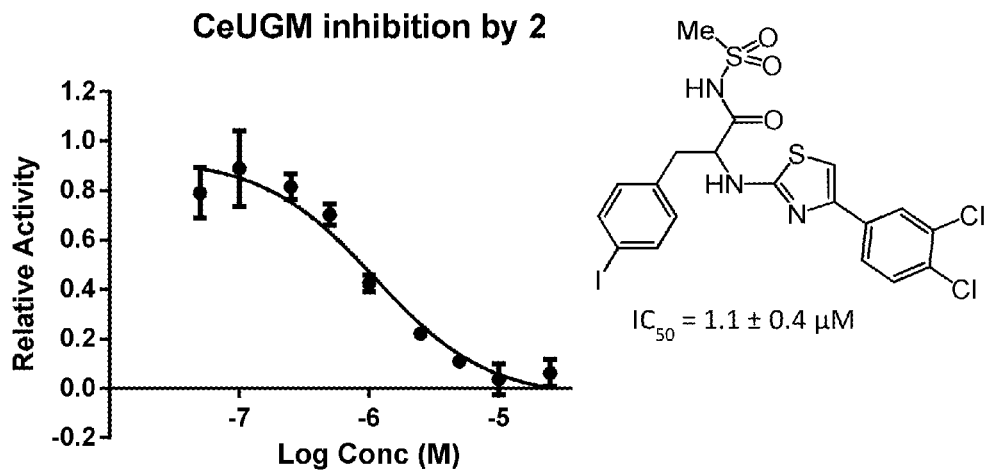
Figure 3C:
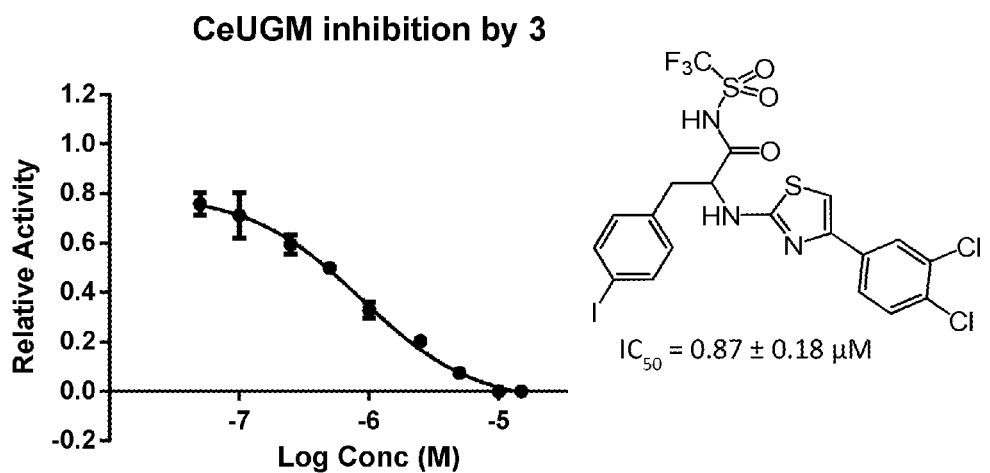

In Table 3, minimum inhibitory concentration (MIC) values are defined as the concentration at which at least 99% of growth inhibition was observed in liquid media. Inhibition values are based on two independent experiments, each including duplicate samples. The average diameter and standard deviation (mm) of an inhibition zone measured inhibition of M. smegmatis growth on solid media On solid media, growth inhibition was evaluated using an agar disk diffusion assay (FIG. 2). [Dykhuisen et al. (2008)] When the methyl ester variant 10 was tested in the disk diffusion assay, no mycobacterial growth inhibition was observed. Under these growth conditions, however, all ¬N-acylsulfonamides except 5 exhibited more potent growth inhibition than did 1, with compound 3 as the most potent. Each inhibitor was further evaluated for inhibition of Escherichia coli BL21, a bacterial strain lacking UGM, using the disk diffusion assay. No antibacterial activity was observed against E. coli by any of the compounds tested.

The generally superior growth inhibition of M. smegmatis by N-acylsulfonamide derivatives may be partially attributed to an enhanced ability to permeate the mycobacterial cell envelope. Comparison of the activity of compounds 1, 2, and 6 provides support for this hypothesis; compounds 2 and 6 each exhibit poorer in vitro inhibition compared to carboxylate 1, yet each displays more potent growth inhibition of *M. smegmatis* than 1. This outcome cannot be satisfactorily explained by affinity or solubility, and suggests that elaboration of a carboxylate to an N-acylsulfonamide moiety alleviates the propensity of the carboxylate to hinder the passage of compounds into cells.

These studies were extended to include an additional UGM lead inhibitor scaffold that was recently identified through virtual screening. —[Kincaid, V. A., et al. (2015)]. Triazolothiadiazine derivatives can also block UGM activity and, similarly to the 2-aminothiazoles, they feature a carboxylate. Lead inhibitor 11 was converted into N-acylsulfonamide derivatives 12 and 13 to afford analogs with properties that mirrored those of the 2-aminothiazole inhibitor variants (Table 4). Both enzymatic and bacterial growth experiments indicated comparable or enhanced inhibitor potency for the N-acylsulfonamide derivatives compared to the carboxylate precursor. No non-specific bacterial growth inhibition was observed against *E. coli*. These results indicate that the strategy may lead to improvements in the efficacy of other UGM inhibitors.

TABLE 4

Inhibition potency of triazolothiadiazine derivatives

| Compound | IC$_{50}$ ($\mu$M)$^a$ | MIC ($\mu$M)$^b$ | Inhibition zone (mm)$^b$ |
|---|---|---|---|
| 11 | 80 ± 29 | 500 | 6.4 ± 0.6 |
| 12 | 108 ± 42 | 500 | 4.3 ± 0.4 |
| 13 | 19 ± 6 | 125 | 8.0 ± 0.1 |

11: X = —OH
12: X = —NHSO$_2$Me
13: X = —NHSO$_2$Ph
Compounds were evaluated for inhibition of $^a$recombinant MtbUGM activity and $^b$replication of *M. smegmatis*.

The development of small molecules that are capable of permeating cell membranes poses a challenge throughout medicinal chemistry and chemical biology. One strategy commonly implemented in eukaryotic cells is to temporarily mask polar groups such as carboxylates via esterification, which promotes passage through the cell membrane. [Campbell, C. T., Sampathkumar, S. G., and Yarema, K. J. (2007) Metabolic oligosaccharide engineering: perspectives, applications, and future directions, Mol. BioSyst. 3, 187-194; Lavis, L. D. (2008) Ester bonds in prodrugs, ACS Chem. Biol. 3, 203-206.] Upon reaching the cytosol, the polar group can be unmasked through the action of cytosolic esterases, thereby regenerating the active form of the small molecule. This strategy relies on the availability of highly promiscuous esterases, and is incompatible with many prokaryotes such as mycobacteria, which often lack such enzymes. Indeed, the inactivity of our methyl ester derivative 7 in cells is consistent with an absence of promiscuous esterases in mycobacteria. Consequently, the design and implementation of alternative solutions is required in such organisms.

This example supports the utility of the N-acylsulfonamide moiety as a carboxylate surrogate to enhance the prokaryotic cell permeability of carboxylate-containing small molecules. The data indicate that the N-acylsulfonamide moiety is an able carboxylate surrogate for two unique UGM inhibitor scaffolds, a modification which also confers increased potency against enzymatic activity and against mycobacterial growth. The ability of 2-aminothiazoles to inhibit UGM homologues from other organisms has been previously established, including nematodes such as *C. elegans*, a species in which carboxylate-containing small molecules generally lack biological activity. N-Acylsulfonamide inhibitors are expected to provide further utility in studying the consequences of Galf depletion in such organisms.

Example 6

Compounds 2, 3, 4, 5, 8, 9, and 13 (in Tables 5-9) all significantly inhibit *C. elegans* proliferation at 250 $\mu$M. As concentration decreases, each of these compounds reaches a threshold where they no longer prevent worm proliferation, but rather cause retarded growth and development. The concentration that appears to be this threshold is reported above. Below this concentration, *C. elegans* growth and proliferation occur, but at a decreased rate with visible ill effects to the animal. Compounds 2 and 3 show the ability to prevent *C. elegans* maturation to adulthood and eventual proliferation when treated at 100 $\mu$M.

TABLE 5

1-10

| | $R_3$ | CeUGM % Inhibition at 2.5 $\mu$M |
|---|---|---|
| 1 | —CO$_2$H | 69.5 ± 1.2 |
| 2 | —CONHSO$_2$CH$_3$ | 80.7 ± 1.1 |
| 3 | —CONHSO$_2$CF$_3$ | 84.8 ± 2.2 |
| 4 | —CONHSO$_2$C$_6$H$_5$ | 92.2 ± 0.2 |
| 5 | —CONHSO$_2$(4-NO$_2$—C$_6$H$_4$) | 93.2 ± 0.1 |
| 6 | —CONHSO$_2$(4-OCH$_3$—C$_6$H$_4$) | 92.4 ± 1.2 |
| 7 | —CONHSO$_2$(4-CH$_3$—C$_6$H$_4$) | 90.5 ± 0.2 |
| 8 | —CONHSO$_2$(4-Cl—C$_6$H$_4$) | 100 ± 0 |
| 9 | —CONHSO$_2$(2-NO$_2$—C$_6$H$_4$) | 92.1 ± 1.0 |
| 10 | —CO$_2$Me | — |

TABLE 6

11-14

[Structure: triazolothiadiazine with 4-Br-benzyl, 4-Cl-phenyl, and R₃ substituent]

| | R₃ | CeUGM % Inhibition at 10 μM |
|---|---|---|
| 11 | —CO₂H | 53.5 ± 3.0 |
| 12 | —CONHSO₂CH₃ | 68.1 ± 2.1 |
| 13 | —CONHSO₂C₆H₅ | 91.7 ± 0.5 |
| 14 | —CO₂Me | — |

TABLE 7

1-10

[Structure: thiazole with 4-iodobenzyl-HN and 3,4-dichlorophenyl, R₃ substituent]

| | R₃ | Effective inhibitor of C. elegans growth at 250 μM |
|---|---|---|
| 1 | —CO₂H | No |
| 2 | —CONHSO₂CH₃ | Yes |
| 3 | —CONHSO₂CF₃ | Yes |
| 4 | —CONHSO₂C₆H₅ | Yes |
| 5 | —CONHSO₂(4-NO₂—C₆H₄) | Yes |
| 6 | —CONHSO₂(4-OCH₃—C₆H₄) | No |
| 7 | —CONHSO₂(4-CH₃—C₆H₄) | No |
| 8 | —CONHSO₂(4-Cl—C₆H₄) | Yes |
| 9 | —CONHSO₂(2-NO₂—C₆H₄) | Yes |
| 10 | —CO₂Me | No |

TABLE 8

11-14

[Structure: triazolothiadiazine with 4-Br-benzyl, 4-Cl-phenyl, and R₃ substituent]

| | R₃ | Effective inhibitor of C. elegans growth at 250 μM |
|---|---|---|
| 11 | —CO₂H | No |
| 12 | —CONHSO₂CH₃ | No |
| 13 | —CONHSO₂C₆H₅ | Yes |
| 14 | —CO₂Me | No |

TABLE 9

1-10

[Structure: thiazole with 4-iodobenzyl-HN and 3,4-dichlorophenyl, R₃ substituent]

| | R₃ | Apparent MIC (μM) to inhibit C. elegans propagation |
|---|---|---|
| 2 | —CONHSO₂CH₃ | 100 |
| 3 | —CONHSO₂CF₃ | 100 |
| 4 | —CONHSO₂C₆H₅ | 250 |
| 5 | —CONHSO₂(4-NO₂—C₆H₄) | 125 |
| 8 | —CONHSO₂(4-Cl—C₆H₄) | 250 |
| 9 | —CONHSO₂(2-NO₂—C₆H₄) | 125 |
| 13 | —CO₂Me | 250 |

Example 7

Figure 4:
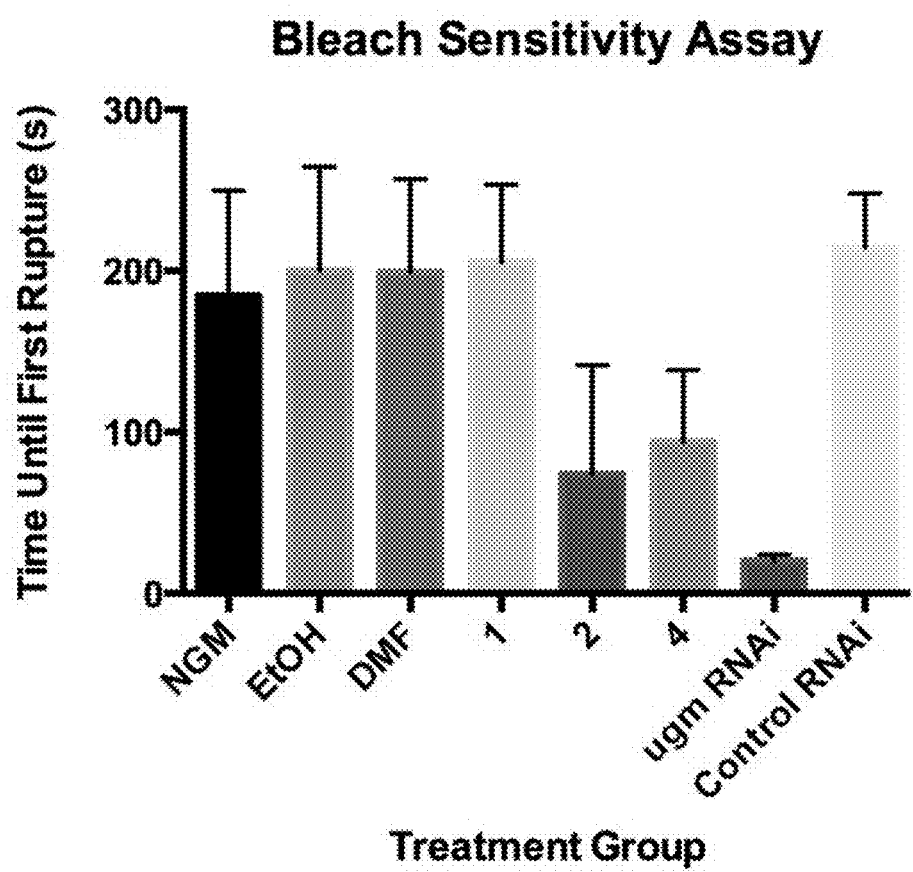
FIG. 4 is a graph of a bleach sensitivity assay using *C. elegans* plotting time of first rupture in seconds as a function of the treatment applied. Contact with compounds 2 and 4 enhances bleach sensitivity significantly.

Compounds were tested at 50 microM. Adult worms (C. elegans) were chosen for testing and time until first rupture was measured when worms were placed in a bleach, sodium hydroxide solution. The statistically significant decrease in time until first rupture for compounds 2 and 4 indicate a cuticle defect, consistent with UGM inhibition. A graph showing results is provided as FIG. 4. Each treatment group has approximately an n=20. The Thompson Tau technique was used to determine statistical outliers.

Example 8

Despite low overall sequence homology among various UGM enzymes, the broad applicability of inhibitors as discussed herein among different UGM is postulated herein to be attributable to a highly conserved active site structure. A co-crystal structure of C. diphtheriae UGM with compound 15 was obtained and used along with molecular docking studies, to guide structural modification described herein. The design, synthesis, and evaluation of novel triazolothiadiazine derivatives with enhanced potency to inhibit the activity of UGM homologs is described in this example.

The C. diphtheriae UGM crystallized in an open, oxidized conformation, bound to triazolothiadiazine 15. This inhibitor is not as potent as compound 11, but it was considered that the structural similarity between compounds 11 and 15 was significant enough that the co-crystal structure could be utilized to assist with the design of further analogs of 11. Inhibitor structure optimization based on the CdUGM homolog was also postulated to extend to other UGM homologs. The binding pose depicted by the crystal structure confirms that 15 binds in the active site to competitively block UGM catalysis of its natural substrates. The carboxylate moiety, indicated by earlier studies as an important feature of UGM inhibitor scaffolds, was observed to engage in a salt bridge interaction with the active site Arg289, one of the same residues responsible for binding the pyrophosphate in UDP-Galp. The R₁ group of 15 (see formulas I and II) extends into a hydrophobic groove, while the $R_2$ group (formulas I and II) fits into a deep pocket bordered by aromatic residues Tyr327 and Trp163. It was hypothesized that inhibitor potency might be enhanced by installing larger $R_1$ groups to extend the ligand binding surface along the hydrophobic groove and that $R_2$ substituents would regulate π-stacking interactions with nearby aromatic residues. In addition, the carboxylate group of the inhibitor 15 is a third region at which inhibitor potency may be modulated.

A convergent synthetic route for preparation of triazolothiadiazine carboxylic acids to facilitate variation of $R_1$ and $R_2$ groups (or $R_{11}$ and $R_{12}$ groups in certain formulas herein) was developed as described in Example 1 (see Scheme 3). In addition, a subset of triazolothiadiazine analogs was modified at the carboxylic acid to generate —CO—Y variants (Scheme 7, with details in Example 1). Earlier studies indicated that an anionic charge at this position is important for inhibitor potency. A panel of functional groups (esters, amides, acylsulfonamides) was screened for their ability to replace the carboxylic acid.

A subset of triazolothiadiazine analogs was modified at the carboxylic acid to generate —CO—Y variants (Scheme 7). Earlier studies indicate that an anionic charge at this position is important for inhibitor potency. A panel of functional groups (esters, amides, acylsulfonamides) was screened for their ability to replace the carboxylic acid.

Scheme 7: Modifications to the carboxylate position of triazolothiadiazine analogs

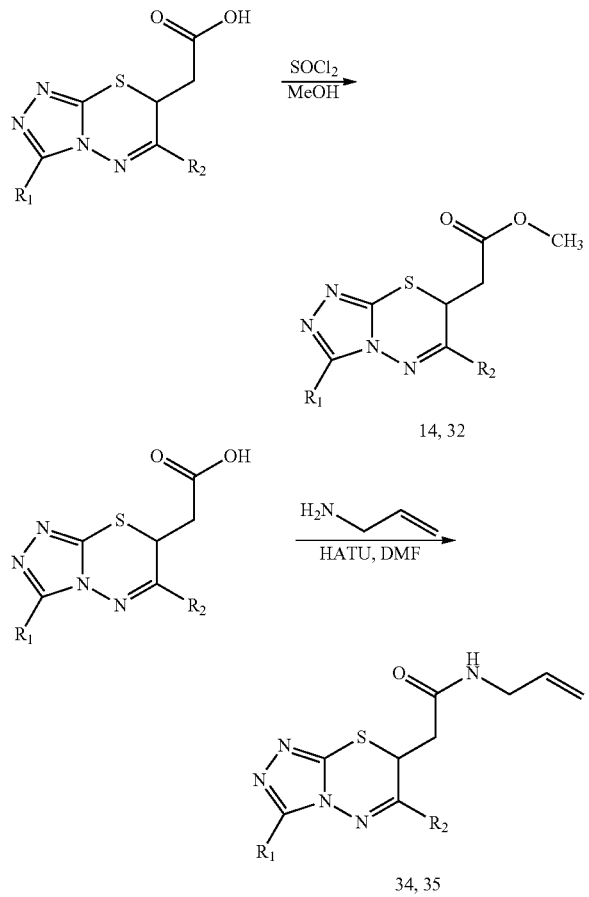

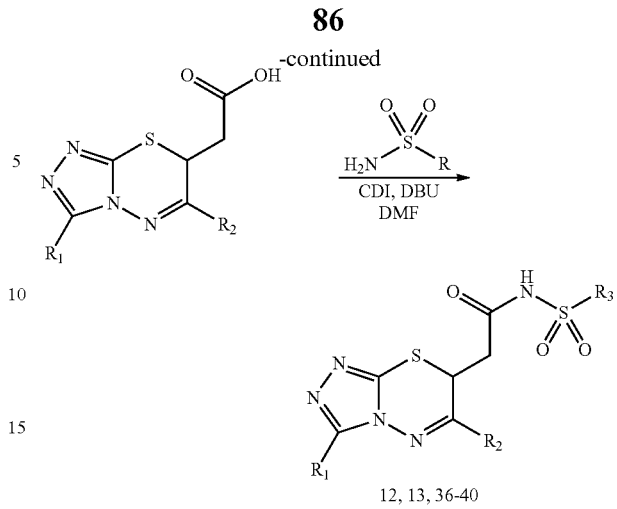

In Vitro Inhibition of MtbUGM

The commercially available lead inhibitor 11 was found to be a potent inhibitor of multiple UGM homologs. This compound was more effective against *K. pneumoniae* and *C. elegans* homologs compared to those from *M. tuberculosis* or *C. diphtheriae*; a similar trend has also been observed in previous inhibitor development. The majority of inhibitor evaluation was performed with variants of 11. Structural modifications that improved relative potency on one inhibitor were likely to transfer to other inhibitors as well. As MtbUGM has generally been found to be the most challenging to inhibit, this enzyme was selected for assessment of UGM inhibition. Furthermore, it is straightforward to compare the cellular activity of inhibitor analogs in mycobacteria, as Galf is an essential component of the mycobacterial cell wall. Thus, UGM inhibition blocks mycobacterial growth and inhibitor potency in whole cells which can readily be observed.

Inhibitor analogs were initially assessed at 100 or 50 μM concentrations for inhibition of MtbUGM, using a previously reported HPLC-based activity assay. These data provided insight into the effects of structural changes on relative potency and dose-responsiveness. A relatively broad range of inhibitor variants was accessed and evaluated (Table 10). In total, 18 carboxylate-bearing analogs were synthesized and tested. The majority of these analogs varied from the commercial lead inhibitor 11 at only a single position ($R_1$ or $R_2$) to allow for straightforward analysis of structure-activity relationships.

At the $R_1$ position, removal of the interstitial methylene present in 11 led to a significant drop in potency (compound 26). However, addition of a second methylene between the heterocyclic core and the $R_1$ arene had a negligible effect (compound 27). With the introduction of a flexible methylene linker, the $R_1$ ring is expected to rotate up along the hydrophobic groove to avoid this steric clash. Given this observation, all subsequently generated inhibitors were designed to maintain a methylene linker between the core and $R_1$. Other perturbations to $R_1$ included the removal of the bromine substituent, which slightly diminished potency (compound 28), and the installation of more bulky aryl groups (compounds 29, 30). Larger $R_1$ arenes led to a significant increase in potency, with compound 29 maintaining high inhibition well below 50 μM.

At the $R_2$ position, variants with a range of electronic and steric properties were assessed. Overall trends revealed that electron-withdrawing substituents enhanced inhibitor potency. In addition, 4-monosubstituted or 3,4-disubstituted rings were well tolerated, but the introduction of 2-substituted rings at $R_2$ led to a significant drop in potency. This ortho substitution likely perturbs the planarity of $R_2$ with the core in a manner that precludes favorable binding to the deep pocket in which $R_2$ resides. As with the $R_1$ modifications, the structure-activity relationships observed for $R_2$ modifications appeared consistent with the structural model discussed above. In particular, the apparent π-stacking between the chlorophenyl moiety of the ligand 15 and the neighboring Y327 was identified as an interaction that could be leveraged to enhance inhibitor potency. Addition of a second halogen, specifically a chlorine atom, to $R_2$ was postulated to render the arene more electron-deficient and as a consequence to strengthen its interaction with the electron-rich tyrosine residue. An increased in UGM inhibition was observed as a result of addition of a second chlorine atom to $R_2$, regardless of whether the $R_1$ position bore a thiophene (compounds 15 vs. 18) or a bromobenzyl (compounds 11 vs. 16) substituent. This effect is believed to be largely electronic in nature, but the addition of a second chorine also constitutes a steric alteration. A comparison of a similar series of compounds bearing mono- or di-methyl substitution as opposed to mono- or di-chloro substitution (compounds 11 and 16 vs. 21 and 17) was examined to dissect these possible electronic and steric effects. This analysis revealed that both the electronic and steric properties of the $R_2$ dichloro substituents were responsible for enhanced potency.

At the —CO—Y position (designated $R_3$ in Table 10), the ability of several functional groups to replace the carboxylic acid: an ester, an amide, and acylsulfonamides was assessed. It was considered that the neutral moieties at this position would be ineffective inhibitors, as their ability to engage in hydrogen bonding with the active site R289 would be diminished. Still, a caveat to this hypothesis is the ambiguity in the crystal structure of whether the ligand carboxylate acts as a hydrogen bond donor or acceptor. Although both esters and amides are poor hydrogen bond donors compared to a carboxylic acid, amides are moderate hydrogen bond acceptors and therefore may be an acceptable surrogate. Evaluation of inhibitor potency of compounds 32, 14 and 34, 35 indicates that neither the ester nor amide variants effectively inhibit MtbUGM. In contrast, the acylsulfonamides are negatively charged at neutral pH. Acylsulfonamide variants 12, 13 and 36-38 all functioned as potent inhibitors, with equal or superior potency compared to the carboxylic acid 11.

Notably, installation of sulfonamides bearing heterocycles appeared to be particularly advantageous; the thiophenesulfonamide analogs 36 and 37 are among the most potent triazolothiadizine inhibitors identified to date. These heterocyclic moieties may access a portion of the active site which is responsible for binding the uridine ring in the natural substrate.

Once each of the three moieties were independently examined, the effects of combined modifications was assessed. Incorporation of the most potent $R_1$ and $R_2$ groups into a single analog (31) revealed that these moieties could indeed be combined to yield an even more potent inhibitor. Furthermore, installation of an acylsulfonamide at —COY ($R_3$) in conjunction with $R_1$ or $R_2$ optimization continued to enhance potency. To date, the most potent triazolothiadiazine analog 40 incorporates modification at all three positions.

TABLE 10

Inhibition of MtbUGM by compounds of formula

| Compound | $R_1$ | $R_2$ | $R_3$ | % inhib Mtb-UGM (100 μM) | % inhib Mtb-UGM (50 μM) | % inhib Mtb-UGM (10 μM) |
|---|---|---|---|---|---|---|
| 15 | 2-thienyl | 4-chlorophenyl | —C(O)OH | 50 | | |
| 11 | 4-bromobenzyl | 4-chlorophenyl | —C(O)OH | 72 | 36 | |
| 16 | 4-bromobenzyl | 3,4-dichlorophenyl | —C(O)OH | 95 | 78 | |

TABLE 10-continued

Inhibition of MtbUGM by compounds of formula

| Compound | R₁ | R₂ | R₃ | % inhib Mtb-UGM (100 μM) | % inhib Mtb-UGM (50 μM) | % inhib Mtb-UGM (10 μM) |
|---|---|---|---|---|---|---|
| 17 | 4-Br-phenyl-CH₂ | 3,4-diMe-phenyl | CH₂COOH | 80 | 41 | |
| 18 | 2-thienyl | 3,4-diCl-phenyl | CH₂COOH | 80 | | |
| 19 | 4-Br-phenyl-CH₂ | 4-Br-phenyl | CH₂COOH | 90 | 67 | |
| 20 | 4-Br-phenyl-CH₂ | 4-CF₃-phenyl | CH₂COOH | 57 | 11 | |
| 21 | 4-Br-phenyl-CH₂ | 4-CH₃-phenyl | CH₂COOH | 63 | 32 | |
| 22 | 4-Br-phenyl-CH₂ | 4-OCH₃-phenyl | CH₂COOH | 44 | 35 | |
| 23 | 4-Br-phenyl-CH₂ | 4-F-phenyl | CH₂COOH | 39 | 25 | |
| 24 | 4-Br-phenyl-CH₂ | 2,4-diMe-phenyl | CH₂COOH | 0 | 1 | |

TABLE 10-continued

Inhibition of MtbUGM by compounds of formula

| Compound | R₁ | R₂ | R₃ | % inhib Mtb-UGM (100 μM) | % inhib Mtb-UGM (50 μM) | % inhib Mtb-UGM (10 μM) |
|---|---|---|---|---|---|---|
| 25 | 4-Br-benzyl | biphenyl | CH₂COOH | 100 | 100 | 100 |
| 26 | 4-Br-phenyl | 4-Cl-phenyl | CH₂COOH | 41 | 23 | |
| 27 | 4-Br-phenethyl | 4-Cl-phenyl | CH₂COOH | 69 | 48 | |
| 28 | benzyl | 4-Cl-phenyl | CH₂COOH | 43 | 30 | |
| 29 | 4-biphenylmethyl | 4-Cl-phenyl | CH₂COOH | 100 | 100 | |
| 30 | 2-naphthylmethyl | 4-Cl-phenyl | CH₂COOH | 88 | 49 | |
| 31 | 4-biphenylmethyl | 3,4-diCl-phenyl | CH₂COOH | 100 | 100 | 50 |

TABLE 10-continued

Inhibition of MtbUGM by compounds of formula

| Compound | R₁ | R₂ | R₃ | % inhib Mtb-UGM (100 μM) | % inhib Mtb-UGM (50 μM) | % inhib Mtb-UGM (10 μM) |
|---|---|---|---|---|---|---|
| 32 | 2-thienyl | 4-chlorophenyl | –C(O)OCH₃ | 20 | | |
| 14 | 4-bromobenzyl | 4-chlorophenyl | –C(O)OCH₃ | 0 | | |
| 34 | 2-thienyl | 4-chlorophenyl | –C(O)NH-allyl | 0 | | |
| 35 | 4-bromobenzyl | 4-chlorophenyl | –C(O)NH-allyl | 0 | | |
| 12 | 4-bromobenzyl | 4-chlorophenyl | –C(O)NHS(O)₂CH₃ | 58 | 50 | |
| 13 | 4-bromobenzyl | 4-chlorophenyl | –C(O)NHS(O)₂Ph | 94 | 92 | |
| 36 | 4-bromobenzyl | 4-chlorophenyl | –C(O)NHS(O)₂-(2-thienyl) | 100 | 87 | 18 |
| 37 | 4-bromobenzyl | 4-chlorophenyl | –C(O)NHS(O)₂-(5-chloro-2-thienyl) | 100 | 100 | 35 |

TABLE 10-continued

Inhibition of MtbUGM by compounds of formula

[Core scaffold: triazole-thiadiazine bicyclic structure with substituents R₁, R₂, R₃]

| Compound | $R_1$ | $R_2$ | $R_3$ | % inhib Mtb-UGM (100 µM) | % inhib Mtb-UGM (50 µM) | % inhib Mtb-UGM (10 µM) |
|---|---|---|---|---|---|---|
| 38 | 4-Br-benzyl | 4-Cl-phenyl | -C(O)NH-SO₂-(1-methylimidazol-4-yl) | 68 | 36 | |
| 39 | 4-Br-benzyl | 3,4-diCl-phenyl | -C(O)NH-SO₂-phenyl | 100 | 100 | 51 |
| 40 | biphenyl-4-ylmethyl | 3,4-diCl-phenyl | -C(O)NH-SO₂-phenyl | 100 | 100 | 85 |

Relative activity of recombinant MtbUGM was evaluated in the presence of inhibitor. The percent inhibition is the mean of two replicates.

Analysis of Inhibitor Aggregation and Alternate Binding Modes

Although the majority of inhibitor analogs fit consistent trends, there were a few outliers. In particular, one $R_2$ variant (25) was significantly more potent than was anticipated based on binding model. This inhibitor analog contains a biphenyl group at the $R_2$ position; the compound was expected to be a poor UGM inhibitor as the biphenyl substitution was expected to be too bulky to be accommodated by the $R_2$ pocket. MtbUGM activity was, however, completely ablated by the presence of 25 even at a concentration as low as 10 µM. A concern was that compound 25 may be inhibiting enzymatic activity through a non-specific mechanism, such as aggregation. To investigate this, we tested the inhibition of MtbUGM by 25 in the presence and absence of Tween80, a surfactant expected to disrupt aggregates. Although it is typical for absolute values of UGM activity to shift in the presence of Tween80, the effect of surfactant on relative inhibitor potency of 25 was insignificant. To further rule out aggregation, the solution properties of 25 were evaluated by dynamic light scattering. No aggregates were observed at either 100 or 10 µM in PBS buffer (1% final concentration of DMSO). Thus, no evidence was found supporting aggregation as a mode of non-specific inhibition by 25. The high potency of 25 and absence of non-specific inhibition indicates that this analog is indeed acting as a specific UGM inhibitor. One rationale for the high potency of 25 is that this inhibitor is binding to the active site through an alternate binding mode.

REFERENCES

1. Global tuberculosis report 2012. Geneva: World Health Organization
2. Chatterjee, D. (1997) The mycobacterial cell wall: structure, biosynthesis and sites of drug action, *Curr. Opin. Chem. Biol.* 1, 579-588.
3. Brennan, P. J. (2003) Structure, function, and biogenesis of the cell wall of *Mycobacterium tuberculosis*, *Tuberculosis* 83, 91-97.
4. Belanger, A. E., Besra, G. S., Ford, M. E., Mikusova, K., Belisle, J. T., Brennan, P. J., and Inamine, J. M. (1996) The embAB genes of *Mycobacterium avium* encode an arabinosyl transferase involved in cell wall arabinan biosynthesis that is the target for the antimycobacterial drug ethambutol, *Proc. Natl. Acad. Sci. U.S.A* 93, 11919-11924.
5. Mikusova, K., Slayden, R. A., Besra, G. S., and Brennan, P. J. (1995) Biogenesis of the mycobacterial cell wall and the site of action of ethambutol, *Antimicrob. Agents Chemother.* 39, 2484-2489.
6. Banerjee, A., Dubnau, E., Quemard, A., Balasubramanian, V., Urn, K. S., Wilson, T., Collins, D., de Lisle, G., and Jacobs, W. R., Jr. (1994) inhA, a gene encoding a target for isoniazid and ethionamide in *Mycobacterium tuberculosis*, *Science* (New York, N.Y.) 263, 227-230.
7. Bruning, J. B., Murillo, A. C., Chacon, O., Barletta, R. G., and Sacchettini, J. C. (2011) Structure of the *Mycobacterium tuberculosis* D-alanine:D-alanine ligase, a target of the antituberculosis drug D-cycloserine, *Antimicrob. Agents Chemother.* 55, 291-301.
8. Koul, A., Arnoult, E., Lounis, N., Guillemont, J., and Andries, K. (2011) The challenge of new drug discovery for tuberculosis, *Nature* 469, 483-490.
9. Zumla, A., Nahid, P., and Cole, S. T. (2013) Advances in the development of new tuberculosis drugs and treatment regimens, *Nat. Rev. Drug. Discov.* 12, 388-404.
10. Houseknecht, J. B., and Lowary, T. L. (2001) Chemistry and biology of arabinofuranosyl- and galactofuranosyl-containing polysaccharides, *Curr. Opin. Chem. Biol.* 5, 677-682.
11. Richards, M. R., and Lowary, T. L. (2009) Chemistry and biology of galactofuranose-containing polysaccharides, *Chembiochem: a European journal of chemical biology* 10, 1920-1938.
12. Pan, F., Jackson, M., Ma, Y., and McNeil, M. (2001) Cell wall core galactofuran synthesis is essential for growth of mycobacteria, *J. Bacteriol.* 183, 3991-3998.
13. Lowary, T. L. (2003) Synthesis and conformational analysis of arabinofuranosides, galactofuranosides and fructofuranosides, *Curr. Opin. Chem. Biol.* 7, 749-756.
14. Soltero-Higgin, M., Carlson, E. E., Gruber, T. D., and Kiessling, L. L. (2004) A unique catalytic mechanism for UDP-galactopyranose mutase, *Nat. Struct. Mol. Biol.* 11, 539-543.
15. Chad, J. M., Sarathy, K. P., Gruber, T. D., Addala, E., Kiessling, L. L., and Sanders, D. A. (2007) Site-directed mutagenesis of UDP-galactopyranose mutase reveals a critical role for the active-site, conserved arginine residues, *Biochemistry* 46, 6723-6732.
16. Liautard, V., Desvergnes, V., and Martin, O. R. (2006) Stereoselective synthesis of alpha-C-Substituted 1,4-dideoxy-1,4-imino-D-galactitols. Toward original UDP-Galf mimics via cross-metathesis, *Org. Lett.* 8, 1299-1302.
17. Caravan, A., Dohi, H., Sinay, P., and Vincent, S. P. (2006) A new methodology for the synthesis of fluorinated exo-glycals and their time-dependent inhibition of UDP-galactopyranose mutase, *Chem. Eur. J.* 12, 3114-3123.
18. Dykhuizen, E. C., May, J. F., Tongpenyai, A., and Kiessling, L. L. (2008) Inhibitors of UDP-galactopyranose mutase thwart mycobacterial growth, *J. Am. Chem. Soc.* 130, 6706-6707.
19. El Bkassiny, S., N'Go, I., Sevrain, C. M., Tikad, A., and Vincent, S. P. (2014) Synthesis of a novel UDP-carba-sugar as UDP-galactopyranose mutase inhibitor, *Org. Lett.* 16, 2462-2465.
20. Veerapen, N., Yuan, Y., Sanders, D. A., and Pinto, B. M. (2004) Synthesis of novel ammonium and selenonium ions and their evaluation as inhibitors of UDP-galactopyranose mutase, *Carbohydr. Res.* 339, 2205-2217.
21. Scherman, M. S., Winans, K. A., Stern, R. J., Jones, V., Bertozzi, C. R., and McNeil, M. R. (2003) Drug targeting *Mycobacterium tuberculosis* cell wall synthesis: development of a microtiter plate-based screen for UDP-galactopyranose mutase and identification of an inhibitor from a uridine-based library, *Antimicrob. Agents Chemother.* 47, 378-382.
22. Soltero-Higgin, M., Carlson, E. E., Phillips, J. H., and Kiessling, L. L. (2004) Identification of inhibitors for UDP-galactopyranose mutase, *J. Am. Chem. Soc.* 126, 10532-10533.
23. Kincaid, V. A., London, N., Wangkanont, K., Wesener, D. A., Marcus, S. A., Heroux, A., Nedyalkova, L., Talaat, A. M., Forest, K. T., Shoichet, B. K., and Kiessling, L. L. (2015) Virtual Screening for UDP-Galactopyranose Mutase Ligands Identifies a New Class of Antimycobacterial Agents, *ACS Chem. Biol.*
24. Klemm, A R, Pell, K. L., Anderson, L. M., Andrew, C. L., and Lloyd, J. B. (1998) Lysosome membrane permeability to anions, *Biochim. Biophys. Acta* 1373, 17-26.
25. Walter, A., and Gutknecht, J. (1984) Monocarboxylic acid permeation through lipid bilayer membranes, *J. Membr. Biol.* 77, 255-264.
26. Ballatore, C., Huryn, D. M., and Smith, A. B., 3rd. (2013) Carboxylic acid (bio)isosteres in drug design, *Chem Med Chem* 8, 385-395.
27. Thiyagarajan, N., Smith, B. D., Raines, R. T., and Acharya, K. R. (2011) Functional and structural analyses of N-acylsulfonamide-linked dinucleoside inhibitors of RNase A, *FEBS J.* 278, 541-549.
28. Somu, R. V., Boshoff, H., Qiao, C., Bennett, E. M., Barry, C. E., and Aldrich, C. C. (2006) Rationally Designed Nucleoside Antibiotics That Inhibit Siderophore Biosynthesis of *Mycobacterium tuberculosis, J. Med. Chem.* 49, 31-34.
29. King, J. F. (2006) Acidity, In *Sulphonic Acids, Esters and their Derivatives* (1991), pp 249-259, John Wiley & Sons, Ltd.
30. Ronn, R., Sabnis, Y. A., Gossas, T., Akerblom, E., Danielson, U. H., Hallberg, A., and Johansson, A. (2006) Exploration of acyl sulfonamides as carboxylic acid replacements in protease inhibitors of the hepatitis C virus full-length NS3, *Bioorg. Med. Chem.* 14, 544-559.
31. Carlson, E. E., May, J. F., and Kiessling, L. L. (2006) Chemical probes of UDP-galactopyranose mutase, *Chem. Biol.* 13, 825-837.
32. Seidler, J., McGovern, S. L., Doman, T. N., and Shoichet, B. K. (2003) Identification and prediction of promiscuous aggregating inhibitors among known drugs, *J. Med. Chem.* 46, 4477-4486.
33. Feng, B. Y., Shelat, A., Doman, T. N., Guy, R. K., and Shoichet, B. K. (2005) High-throughput assays for promiscuous inhibitors, *Nat. Chem. Biol.* 1, 146-148.
34. Collins, L., and Franzblau, S. G. (1997) Microplate alamar blue assay versus BACTEC 460 system for high-throughput screening of compounds against *Mycobacterium tuberculosis* and *Mycobacterium avium, Antimicrob. Agents Chemother.* 41, 1004-1009.
35. Magnet, S., Hartkoorn, R. C., Szekely, R., Pato, J., Triccas, J. A., Schneider, P., Szantai-Kis, C., Orfi, L., Chambon, M., Banfi, D., Bueno, M., Turcatti, G., Keri, G., and Cole, S. T. (2010) Leads for antitubercular compounds from kinase inhibitor library screens, *Tuberculosis* 90, 354-360.
36. Pethe, K., Sequeira, P. C., Agarwalla, S., Rhee, K., Kuhen, K., Phong, W. Y., Patel, V., Beer, D., Walker, J. R., Duraiswamy, J., Jiricek, J., Keller, T. H., Chatterjee, A., Tan, M. P., Ujjini, M., Rao, S. P. S., Camacho, L., Bifani, P., Mak, P. A., Ma, I., Barnes, S. W., Chen, Z., Plouffe, D., Thayalan, P., Ng, S. H., Au, M., Lee, B. H., Tan, B. H., Ravindran, S., Nanjundappa, M., Lin, X., Goh, A., Lakshminarayana, S. B., Shoen, C., Cynamon, M., Kreiswirth, B., Dartois, V., Peters, E. C., Glynne, R., Brenner, S., and Dick, T. (2010) A chemical genetic screen in *Mycobacterium tuberculosis* identifies carbon-source-dependent growth inhibitors devoid of in vivo efficacy, *Nat. Commun.* 1, 57.
37. Miller, C. H., Nisa, S., Dempsey, S., Jack, C., and O'Toole, R. (2009) Modifying culture conditions in chemical library screening identifies alternative inhibitors of mycobacteria, *Antimicrob. Agents Chemother.* 53, 5279-5283.

38. Nikaido, H. (2003) Molecular basis of bacterial outer membrane permeability revisited, *Microbiol. Mol. Biol. Rev.* 67, 593-656.
39. Delcour, A. H. (2009) Outer membrane permeability and antibiotic resistance, *Biochim. Biophys. Acta* 1794, 808-816.
40. Rafi, S. B., Hearn, B. R., Vedantham, P., Jacobson, M. P., and Renslo, A. R. (2012) Predicting and improving the membrane permeability of peptidic small molecules, *J. Med. Chem.* 55, 3163-3169.
41. Walter, A., and Gutknecht, J. (1986) Permeability of small nonelectrolytes through lipid bilayer membranes, *J. Membr. Biol.* 90, 207-217.
42. Orsi, M., Sanderson, W. E., and Essex, J. W. (2009) Permeability of small molecules through a lipid bilayer: a multiscale simulation study, *J. Phys. Chem. B* 113, 12019-12029.
43. Campbell, C. T., Sampathkumar, S. G., and Yarema, K. J. (2007) Metabolic oligosaccharide engineering: perspectives, applications, and future directions, *Mol. BioSyst.* 3, 187-194.
44. Lavis, L. D. (2008) Ester bonds in prodrugs, *ACS Chem. Biol.* 3, 203-206.
45. Liederer, B. M., and Borchardt, R. T. (2006) Enzymes involved in the bioconversion of ester-based prodrugs, *J. Pharm. Sci.* 95, 1177-1195.
46. Redinbo, M. R., and Potter, P. M. (2005) Keynote review: Mammalian carboxylesterases: From drug targets to protein therapeutics, *Drug Discov. Today* 10, 313-325.
47. Satoh, T., and Hosokawa, M. (2006) Structure, function and regulation of carboxylesterases, *Chem.-Biol. Interact.* 162, 195-211.
48. Burns, A. R., Wallace, I. M., Wildenhain, J., Tyers, M., Giaever, G., Bader, G. D., Nislow, C., Cutler, S. R., and Roy, P. J. (2010) A predictive model for drug bioaccumulation and bioactivity in *Caenorhabditis elegans*, *Nat. Chem. Biol.* 6, 549-557.
49. Kamel, M. M.; Megally Abdo, N. Y., Synthesis of novel 1,2,4-triazoles, *triazolothiadiazines and triazolothiadiazoles as potential anticancer agents. European Journal of Medicinal Chemistry* 2014, 86, 75-80.
50. Kaplancikh, Z. A.; Turan-Zitouni, G.; Özdemir, A.; Revial, G., New triazole and triazolothiadiazine derivatives as possible antimicrobial agents. *European Journal of Medicinal Chemistry* 2008, 43 (1), 155-159.
51. Bolognese, A.; Scherillo, G., Solvolysis in dipolar aprotic solvents. Behavior of 4-(p-substituted phenyl)-4-oxo-2-bromobutanoic acids in dimethyl sulfoxide: substituent effect. *The Journal of Organic Chemistry* 1977, 42 (24), 3867-3869.

We claim:
1. A compound of formula I:

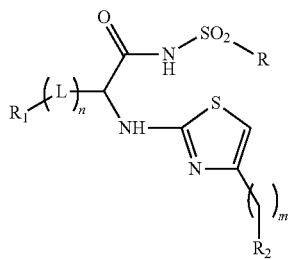

or salts thereof, wherein
n is 0 or 1 and L is —$(CH_2)_q$- or O—$(CH_2)_q$, where q is 1, 2 or 3;
m is 0, 1, 2, or 3;
R is an optionally substituted $C_1$-$C_6$ alkyl, an optionally substituted $C_1$-$C_6$ alkenyl, an optionally substituted alkoxy, an optionally substituted thioalkyl, an optionally substituted carbocyclyl, or an optionally substituted heterocyclyl;
$R_1$ and $R_2$ are independently selected from optionally substituted carbocyclyl, and optionally substituted heterocyclyl; and
wherein optional substitution is substitution by one or more non-hydrogen substituents selected from halogen, hydroxyl, mercapto, nitro, cyano, azide, isocyano, thiocyano, oxo, optionally substituted $C_1$-$C_3$ alkyl, optionally substituted $C_1$-$C_3$-alkenyl, optionally substituted $C_1$-$C_3$ alkoxy, acyl, halogenated phenyl, nitrophenyl, alkoxyphenyl, thioalkyl, optionally substituted heteroaryl, optionally substituted cycloalkyl, optionally substituted heterocyclyl, —$SO_2$—$N(R_S)_2$, —$SO_2$—$R_S$, —$COOR_S$, —$COR_S$, —$CON(R_S)_2$, —$N(R_S)_2$, where $R_S$ is hydrogen, $C_1$-$C_3$ alkyl, $C_1$-$C_3$ alkenyl, $C_1$-$C_3$ haloalkyl, $C_1$-$C_3$ haloalkoxy, phosphate, phosphonate, or carboxyl.

2. The compound of claim 1, wherein $R_1$ and $R_2$ are independently selected from phenyl, biphenyl, naphthyl or heteroaryl, wherein each of these groups are optionally substituted with one or more halogen, nitro, cyano, $C_1$-$C_3$ alkyl, $C_1$-$C_3$ alkoxy, acyl, or $C_1$-$C_3$ haloalkyl.

3. The compound of claim 1, wherein $R_1$ and $R_2$ are independently selected from phenyl, biphenyl, or heteroaryl, wherein each of these groups are optionally substituted with one or more halogen, nitro, methyl, methoxy, acetyl or trifluoromethyl.

4. The compound of claim 1, wherein $R_1$ and $R_2$ are different groups.

5. The compound of claim 1, wherein one of $R_1$ and $R_2$ is selected from optionally substituted biphenyl, or optionally substituted naphthyl and the other of $R_1$ or $R_2$ is selected from optionally substituted phenyl or optionally substituted heteroaryl, wherein optionally substituted is substitution with one or more halogen, nitro, methyl, methoxy, acetyl or trifluormethyl groups.

6. The compound of claim 1, wherein n is 0 or 1 and m is 0 or 1.

7. The compound of claim 1, wherein $R_1$ is 4-bromo phenyl, 4-iodo phenyl, naphthyl, or biphenyl and $R_2$ is 4-bromophenyl, 4-iodo phenyl, 4-chlorophenyl, 3,4-dichlorophenyl or biphenyl.

8. A method for inhibiting Uridine 5'-diphosphate (UDP)-galactopyranose mutase (UGM) which comprises contacting UGM with an amount of one or more compounds or salts of claim 1 effective for inhibiting the enzyme.

9. The method of claim 8, wherein the UGM is that of a *mycobacterium* or a nematode.

10. A method for inhibiting the growth of a microorganism which comprises contacting the microorganism or an environment containing the microorganism with an effective amount of one or more compounds or salts of claim 1, wherein the microorganism is a bacterium, a fungus, an algae or a nematode.

11. The method of claim 10, wherein the microorganism is a *mycobacterium* or a nematode.

12. A method of treating an infection by a microorganism having Uridine 5'-diphosphate (UDP)-galactopyranose mutase (UGM) in an individual in need of such treatment by administering to the individual an effective amount of one or more compounds of claim 1, wherein the microorganism is a bacterium, a fungus, an algae or a nematode.

13. The method of claim 12, wherein the infection is tuberculosis.

14. A compound of formula VA:

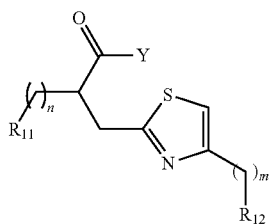

and salts thereof,
where:
Y is OH, or NHSO$_2$R;
n and m are independently 0 or 1;
R is an optionally substituted C$_1$-C$_6$ alkyl, an optionally substituted C$_1$-C$_6$ alkenyl, an optionally substituted alkoxy, an optionally substituted thioalkyl, an optionally substituted carbocyclyl, or an optionally substituted heterocyclyl; and
R$_{11}$ and R$_{12}$ are selected from an optionally substituted carbocyclyl, or an optionally substituted heterocyclyl, wherein one of R$_{11}$ or R$_{12}$ is an optionally substituted biphenyl or an optionally substituted naphthyl; and
wherein optional substitution is substitution with one or more halogen, C$_1$-C$_3$alkyl, C$_1$-C3 alkoxy, nitro, cyano, acyl, or halogenated C$_1$-C$_3$ alkyl.

15. The compound or salt of claim 14, wherein one of R$_{11}$ or R$_{12}$ is an substituted biphenyl or an unsubstituted naphthyl.

16. The compound or salt of claim 14, wherein R$_{11}$ and R$_{12}$ are selected from optionally substituted phenyl, optionally substituted biphenyl, optionally substituted naphthyl or optionally substituted heteroaryl.

17. The compound or salt of claim 15, wherein one of R$_{11}$ or R$_{12}$ is an optionally substituted biphenyl and the other of R$_{11}$ or R$_{12}$ is selected from furan-2-yl, furan-3-yl, thiophen-2-yl, thiophen-3-yl, 1-methylfuran-3-yl, 4-methylphenyl, 4-methoxyphenyl, 4-fluorophenyl, 4-bromophenyl, 4-chlorophenyl, or 4-iodophenyl.

18. The compound or salt of claim 14, where R is selected from unsubstituted C$_1$-C$_3$ alkyl, C$_1$-C$_3$ haloalkyl, unsubstituted phenyl, phenyl substituted with one or more halogen, nitro substituted phenyl, thiophen-2-yl, halogenated thiophen-2-yl, thiophen-3-yl, halogenated thiophen-3-yl, imidazol-4-yl, imidazol-3-yl, imidazol-2-yl, and 1-alkyl imidazol-4-yl.

19. A pharmaceutically acceptable composition which comprises one or more compounds or salts of claim 14 and a pharmaceutically acceptable carrier.

20. A method for inhibiting Uridine 5'-diphosphate (UDP)-galactopyranose mutase (UGM) which comprises contacting UGM with an amount of one or more compounds or salts of claim 14 effective for inhibiting the enzyme.

21. A method for inhibiting the growth of a microorganism which comprises contacting the microorganism or an environment containing the microorganism with an effective amount of one or more compounds or salts of claim 14, wherein the microorganism is a bacterium, a fungus, an algae or a nematode.

22. A method of treating an infection by a microorganism having Uridine 5'-diphosphate (UDP)-galactopyranose mutase (UGM) in an individual in need of such treatment by administering to the individual an effective amount of one or more compounds of claim 14, wherein the microorganism is a bacterium, a fungus, an algae or a nematode.

23. The method of claim 22, wherein the infection is tuberculosis.

24. The compound of claim 1, having formula:

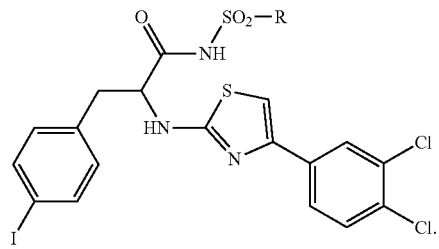

25. The compound of claim 24, wherein R is selected from methyl, trifluoromethyl, phenyl, 4 nitrophenyl, 4-chlorophenyl and 2-nitrophenyl.

26. The method of claim 21, wherein the microorganism is a bacterium.

* * * * *

UNITED STATES PATENT AND TRADEMARK OFFICE
CERTIFICATE OF CORRECTION

Page 1 of 1

PATENT NO. : 10,080,757 B2
APPLICATION NO. : 15/456828
DATED : September 25, 2018
INVENTOR(S) : Kiessling et al.

It is certified that error appears in the above-identified patent and that said Letters Patent is hereby corrected as shown below:

In the Claims

In Claim 1, Line 2, please delete "O—(CH$_2$)$_q$" and replace with -- –O–(CH$_2$)$_q$ --

In Claim 14, Line 20, please delete "NHSO$_2$R" and replace with -- –NHSO$_2$R --

In Claim 25, Line 43, please delete "4 nitrophenyl" and replace with -- 4-nitrophenyl --

Signed and Sealed this
Second Day of July, 2019

Andrei Iancu
*Director of the United States Patent and Trademark Office*